(12) United States Patent
Starrett, Jr. et al.

(10) Patent No.: US 7,169,803 B2
(45) Date of Patent: Jan. 30, 2007

(54) N-SUBSTITUTED PRODRUGS OF FLUOROOXINDOLES

(75) Inventors: John E. Starrett, Jr., Middletown, CT (US); Omar D. Lopez, Wallingford, CT (US); Piyasena Hewawasam, Middletown, CT (US); Min Ding, Glastonbury, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 127 days.

(21) Appl. No.: 11/074,288

(22) Filed: Mar. 7, 2005

(65) Prior Publication Data

US 2005/0203089 A1 Sep. 15, 2005

Related U.S. Application Data

(60) Provisional application No. 60/553,319, filed on Mar. 15, 2004.

(51) Int. Cl.
*A61K 31/405* (2006.01)
*C07D 209/34* (2006.01)

(52) U.S. Cl. .................................. 514/418; 548/486
(58) Field of Classification Search ............. 548/486; 514/418
See application file for complete search history.

(56) References Cited

U.S. PATENT DOCUMENTS 5,602,169 A 2/1997 Hewawasam et al.
6,930,100 B2 * 8/2005 Gillman et al. ............. 514/80

FOREIGN PATENT DOCUMENTS

WO WO 90/08128 7/1990

OTHER PUBLICATIONS

Ahmed, F., et al., "Some Features of the Spasmogenic Actions of Acetylcholine and Histamine in Guinea-Pig Isolated Trachealis", *Br. J. Pharmacol.*, 83: 227-233 (1984).
Baró, I. and Escande, D., "A $Ca^{2+}$-activated $K^+$ Current in Guinea-pig Atrial Myocytes", *Pflügers Archiv.*, 414 (Suppl. 1): S168 (1989).
Bungaard, et al., "A Novel Solution-Stable, Water-Soluble Prodrug Type for Drugs Containing a Hydroxyl or an NH-Acidic Group", *J. Med. Chem.*, 32(12): 2503-2507 (1989).
Cook, N.S., "The Pharmacology of Potassium Channels and Their Therapeutic Potential", *Trends in Pharmacol. Sciences*, 9: 21-28 (Jan. 1988).

Gribkoff, et al., "Targeting acute ischemic stroke with a calcium-sensitive opener of maxi-K potassium channels", *Nature Medicine*, 7(4): 471-477 (2001).
Koh, D-S., et al., "Effect of the Flavoid Phloretin on $Ca^{2+}$-activated $K^+$ Channels in Myelinated Nerve Fibres of *Xenopus laevis*", *Neuroscience Lett.*, 165: 167-170 (1994).
Quast, U. and Cook, N. S., "Moving Together: $K^+$ Channel Openers and ATP-sensitive $K^+$ Channels", *Trends in Pharmacol. Sciences*, 10: 431-435 (Nov. 1989).
Singer, J. J. and Walsh, J.V., "Characterization of Calcium-activated Potassium Channels in Single Smooth Muscle Cells Using the Patch-clamp Technique", *Pflügers Archiv.*, 408: 98-111 (1987).
Trivedi, S., et al., "Calcium Dependent K-Channels in Guinea Pig and Human Urinary Bladder", *Biochemical and Biophysical Research Communications*, 213( 2): 404-409 (Aug. 1995).
Varia, S.A., et al., Phenytoin Prodrugs III: Water-Soluble Prodrugs for Oral and/or Parenteral Use:, *J. Pharm. Sci.*, 73(8): 1068-1073 (1984).

* cited by examiner

*Primary Examiner*—Joseph K. McKane
*Assistant Examiner*—Michael P. Barker
(74) *Attorney, Agent, or Firm*—Aldo A. Algieri

(57) ABSTRACT

The present invention provides novel N-substituted fluorooxindoles having the general Formula I

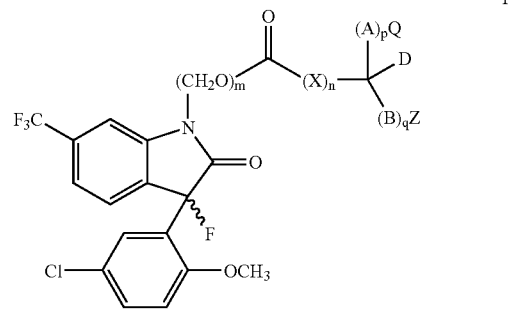

wherein the wavy bond (⌒)

represents the racemate, the (R)-enantiomer or the (S)-enantiomer and m, n, p, q, A, B, D, Q, X, and Z are as defined below, or a nontoxic pharmaceutically acceptable salt or solvate thereof and are useful in the treatment of disorders which are responsive to the opening of potassium channels.

10 Claims, No Drawings

N-SUBSTITUTED PRODRUGS OF FLUOROOXINDOLES

CROSS-REFERENCE TO RELATED APPLICATIONS

This is a non-provisional application which claims the benefit of U.S. Provisional Application No. 60/553,319 filed Mar. 15, 2004.

FIELD OF THE INVENTION

The present invention is directed to novel N-Substituted derivatives of a fluorooxindole compound which is a modulator of the large-conductance calcium-activated potassium (BK) channels and, therefore, useful in the protection of neuronal cells and diseases arising from dysfunction of cellular membrane polarization and conductance. The present invention also provides a method of treatment with the novel substituted fluorooxindole derivatives and to pharmaceutical compositions thereof.

BACKGROUND OF THE INVENTION

Stroke is presently recognized as the third leading cause of adult disability and death in the United States and Europe. In the past decade, several therapeutic approaches for the minimization of stroke-related brain damage have been pursued including inhibitors of AMPA/kainate, N-methyl-D-aspartate (NMDA) and adenosine reuptake inhibitors. It is the object of the present invention to provide novel compounds that will modulate potassium channels, in particular, large-conductance calcium-activated potassium (BK) channels which will be useful in reducing neuronal damage during ischemic conditions of a stroke episode.

Potassium channels play a key role in regulation of cell membrane potential and modulation of cell excitability. Potassium channels are themselves regulated by voltage, cell metabolism, calcium ion and receptor mediated processes. [Cook, N. S., *Trends in Pharmacol. Sciences*, 9, pp. 21–28 (1988); and Quast, U. and Cook, N. S., *Trends in Pharmacol. Sciences*, 10, pp. 431–435 (1989)]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK) >150 pS; intermediate conductance 50–150 pS; small conductance <50 pS. ("pS" stands for picosiemen, a unit of electrical conductance.) Large-conductance calcium-activated potassium (BK) channels are present in many excitable cells including neurons, cardiac cells and various types of smooth muscle cells. [Singer, J. J. and Walsh, J. V., *Pflügers Archiv.*, 408, pp. 98–111 (1987); Baró, I., and Escande, D., *Pflügers Archiv.*, 414 (Suppl. 1), pp. S 168–S 170 (1989); and Ahmed, F. et al., *Br. J. Pharmacol.*, 83, pp. 227–233 (1984)].

Potassium ions play a dominant role in controlling the resting membrane potential in most excitable cells and in maintaining the transmembrane voltage near the $K^+$ equilibrium potential ($E_k$) of about −90 mV. It has been shown that opening of potassium channels shifts the cell membrane potential towards the equilibrium potassium membrane potential ($E_k$), resulting in hyperpolarization of the cell. [Cook, N. S., *Trends in Pharmacol. Sciences*, 9, pp. 21–28 (1988)]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells under ischemic conditions.

The role of potassium channels in the operation of the smooth muscle of the human urinary bladder is discussed by S. Trivedi, et al. in *Biochemical and Biophysical Research Communications*, (1995), 213, No. 2, pp. 404–409.

A range of synthetic and naturally occurring compounds with BK opening activity have been reported. The *avena* pyrone extracted from *avena sativa*-common oats has been identified as a BK channel opener using a lipid bi-layer technique [International Patent application WO 93/08800, published May 13, 1993]. The flavanoid, Phloretin has been found to affect the opening of $Ca^{2+}$-activated potassium channels in myelinated nerve fibers of *Xenopus laevis* using outside-out patches [Koh, D-S., et al., *Neuroscience Lett.*, 165, pp. 167–170 (1994)].

Varia disclosed the use of phosphonomethoxy derivatives as prodrugs of the hydantoin Phenytoin in *J. Pharm. Sci.* 73, pp. 1068–1073 (1984). In the same publication, they have also disclosed the use of 3-(hydroxymethyl) sulfate of Phenytoin as a potential hydantoin prodrug.

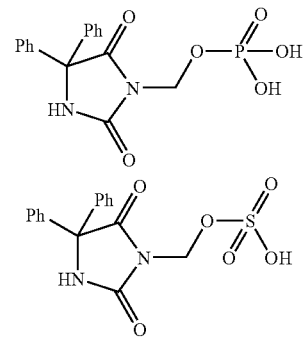

Bungaard, et al. have shown in WO 9008128 and in *J. Med. Chem.* 32, pp. 2503–2507 (1989) that drugs such as the hydantoin Phenytoin can be derivatized as N-[[[(Aminomethyl)benzoyl]oxy]methyl] derivatives and that the N-[[[(Aminomethyl)benzoyl]oxy]methyl] functionality is cleaved in human plasma to afford the parent hydantoin.

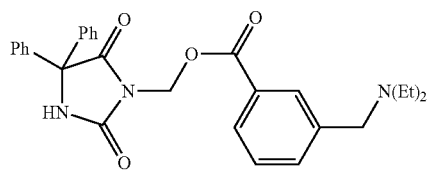

Hewawasam, et al. demonstrated in U.S. Pat. No. 5,602, 169 issued Feb. 11, 1997, that (S)-3-(5-chloro-2-methoxyphenyl)-3-fluoro-6-(trifluoromethyl)indolin-2-one is a modulator of large-conductance, calcium-activated potassium (BK) channels, and is useful for the treatment of ischemia.

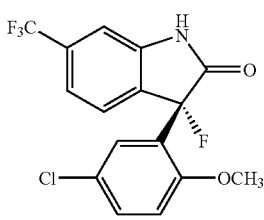

Hewawasam et. al. in U.S. Pat. No. 5,602,169 also described the synthesis of the above compound and its utility to treat disorders sensitive to potassium channel opening, including cerebral ischemia and traumatic brain injury. Due to the low aqueous solubility of the above compound, additives such as dimethylsulfoxide and propylene glycol, for example, must be employed in order to prepare solutions of the compound of Formula I suitable for intravenous injection (Gribkoff, et al., *Nature Medicine,* 2001, 7, 471–477).

SUMMARY OF THE INVENTION

The present invention provides novel N-substituted fluorooxindoles having the general Formula I

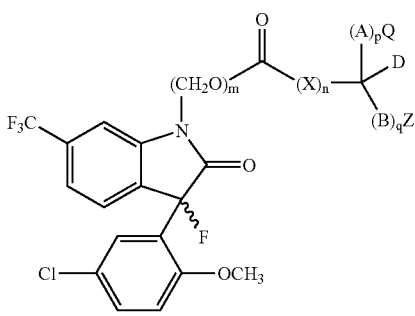

wherein the wavy bond (∿∿) represents the racemate, the (R)-enantiomer or the (S)-enantiomer and m, n, p, q, A, B, D, Q, X, and Z are as defined below, or a nontoxic pharmaceutically acceptable salt or solvate thereof The N-1 substituted fluorooxindoles of the present invention increase the water solubility of the 3-fluorooxindoles, and thereby decrease the amount of additives that need to be employed to deliver an intravenous dose of the oxindole. Upon systemic administration, the oxindole derivatives are transformed to liberate systemic levels of the fluorooxindole. The present invention also provides pharmaceutical compositions comprising said N-1 substituted fluorooxindoles and to the method of treatment of disorders sensitive to potassium channel opening activity such as ischemia, stroke, convulsions, asthma, epilepsy, irritable bowel syndrome, migraine, traumatic brain injury, spinal cord injury, sexual dysfunction, carbon monoxide poisoning and urinary incontinence.

DETAILED DESCRIPTION OF THE INVENTION

The present invention provides novel N-1 subsituted flurooxindoles of the racemate, the (R)-enantiomer and (S)-enantiomer of 3-(5-chloro-2-methoxyphenyl)-3-fluoro-6-(trifluoromethyl)indolin-2-one (compound of Formula IV)

which is a potent opener of the large conductance, calcium-activated K$^+$-channels (BK channel) and the novel derivatives of the present invention have the general Formula I

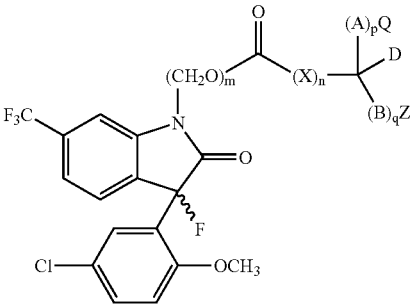

wherein the wavy bond (∿∿) represents the racemate, the (R)-enantiomer or the (S)-enantiomer;
A and B are independently $C_{1-4}$ alkyl or a direct bond;
D is H or $CH_3$;
X is O, $CH_2$, phenyl or $(NR_1)_r$;
Q and Z are each independently H, $SO_3H$, $NR_1R_2$, $NR_1$—$CH_2CH_2$—$NR_1R_2$,

—C(O)OH, OH, $OCH_2C(O)OH$, $C(O)OCH_2CO(O)H$, $C(O)NR_1CH_2CH_2SO_3H$, phenyl, piperdinyl, piperizinyl, methylpiperizinyl, morpholinyl, or tetrazol-5-yl;
m, n, p, q, r are each independently an integer of 0 or 1; and
$R_1$, $R_2$, and $R_3$ are each independently H or $C_{1-4}$ alkyl;
or a nontoxic pharmaceutically acceptable salt or solvate thereof.

The present invention also provides a method for the treatment of or protection from disorders which are mediated by opening of the large conductance calcium-activated K$^+$ channels (BK channels) in a mammal in need thereof, which comprises administering to said mammal a therapeutically effective amount of a compound of Formula I or a nontoxic pharmaceutically acceptable salt thereof. Preferably, the compounds of Formula I are useful in the treatment of ischemia, stroke, epilepsy, convulsions, asthma, irritable bowel syndrome, migraine, traumatic brain injury, spinal cord injury, sexual dysfunction, carbon monoxide poisoning and urinary incontinence and other disorders sensitive to BK channel activating activity.

The term "$C_{1-4}$ alkyl" as used herein and in the claims (unless the context indicates otherwise) means straight or branched chain alkyl groups such as methyl, ethyl, propyl, isopropyl, butyl and isobutyl. Preferably, these groups contain from 1 to 2 carbon atoms.

The term "a nontoxic pharmaceutically acceptable salt" as used herein and in the claims is intended to include nontoxic base addition salts with inorganic and organic bases. The salt of a Formula I compound which may be represented herein by M$^\oplus$ includes the monoanionic, the dianionic and trianionic salts, for example, the mono sodium, the di sodium and the tri sodium salts. Suitable inorganic bases such as alkali and alkaline earth metal bases include metallic cations such as sodium, potassium, magnesium, calcium and the like. Suitable organic bases include amines such as ammonium, alkylamine, dialkylamine, trialkylamines, tetraalkylammonnium, pyridine, dibenzylamine, ethanolamine, N-methylglucamine, N-methylpiperidine, N-methylmorpholine, lysine, arginine and other amines which have been used to form salts of carboxylic acids and sulfuric acids.

Generally, pharmaceutically acceptable salts of the invention are those in which the counter-ion does not contribute significantly to the toxicity or pharmacological activity of the salt. In some instances, they have physical properties which make them more desirable for pharmaceutical formulations, such as solubility, lack of hygroscopicity, compressibility with respect to tablet formation and compatibility with other ingredients with which the substance may be used for pharmaceutical purposes. The salts are routinely made by admixture of a Formula I compound wherein with a selected base, preferably by contact in solution employing an excess of commonly used inert solvents such as water, ether, acetonitrile, dioxane, methylene chloride, isopropanol, methanol, ethanol, ethyl acetate and acetonitrile. They may also be made by metathesis or treatment with an ion exchange resin under conditions in which the appropriate ion of a salt of the substance of the Formula I compound is replaced by another ion under conditions which allow for separation of the desired species such as by precipitation from solution or extraction into a solvent, or elution from or retention on an ion exchange resin.

Certain compounds of the present invention including the pharmaceutically acceptable salts thereof can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the composition that is sufficient to show a meaningful patient benefit, i.e., healing of acute conditions characterized by openers of large conductance calcium-activated $K^+$ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

In another aspect, this invention provides water-soluble prodrugs of the compound of the racemate, the (R)-enantiomer and the (S)-enantiomer of 3-(5-chloro-2-methoxyphenyl)-3-fluoro-6-(trifluoromethyl)indolin-2-one which is described in U.S. Pat. No. 5,602,169. As used herein, the term prodrug denotes a derivative of an active drug which is converted after administration back to the active drug. More particularly, it refers to ester, amide and carbamate derivatives of 3-fluorooxindole drugs which are capable of undergoing hydrolysis to release active free drug. For example, the N–1 substituted flurooxindoles may be hydrolyzed in the host to produce a more active form of the desired 3-fluorooxindole. The physiologically hydrolyzable groups also serve as prodrugs by being hydrolyzed in the body to yield the parent drug per se, and thus, the water-soluble prodrugs of the present invention are preferred for administration of the parent drug.

In still another aspect, this invention provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt, solvate or hydrate thereof. Preferably, the compounds of Formula I are useful in the treatment of ischemia, stroke, convulsions, epilepsy, asthma, irritable bowel syndrome, migraine, traumatic brain injury, spinal cord injury, carbon monoxide poisoning, urinary incontinence and sexual dysfunction in both men (erectile dysfunction, for example, due to diabetes mellitus, spinal cord injury, radical prostatectomy, psychogenic etiology or any other cause) and women by improving blood flow to the genitalia, especially the corpus cavernosum, and other disorders sensitive to BK channel activating activity. Most preferably, the compounds of Formula I are useful in the treatment of cerebral ischemia/stroke.

In still yet another aspect, this invention provides pharmaceutical compositions comprising at least one compound of Formula I in combination with a pharmaceutical adjuvant, carrier or diluent.

The compounds of Formula I may be prepared by various procedures such as those illustrated herein in the examples, in the Reaction Schemes and variations thereof which would be evident to those skilled in the art. The various prodrug compounds of Formula I may advantageously be prepared from the active drug substance of Formula IV which is itself prepared by the general procedure described in U.S. Pat. No. 5,602,169 and used as the starting material in the methods illustrated in Reaction Schemes 1 to 10.

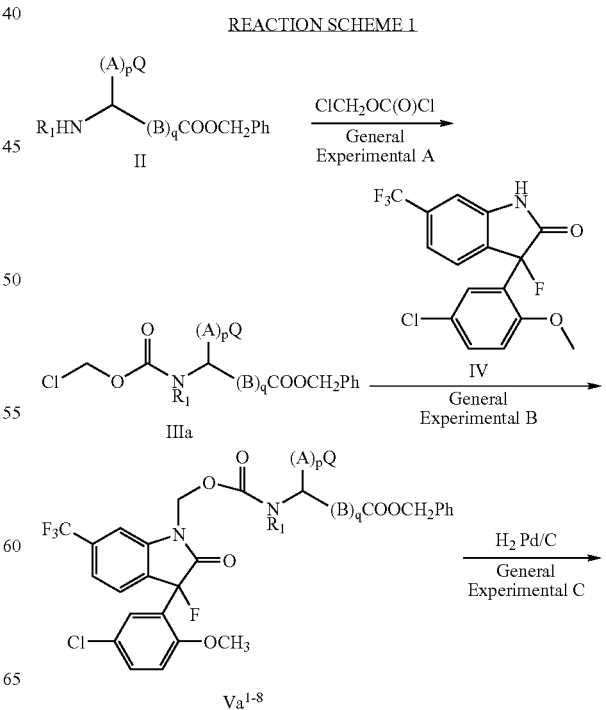

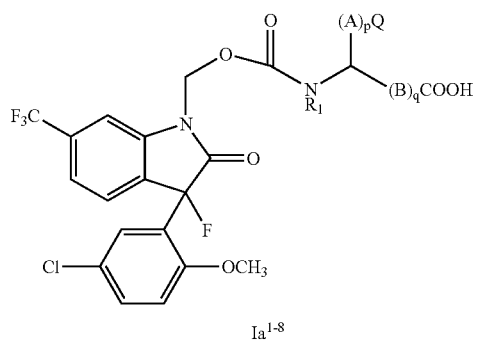

Ia[1-8]

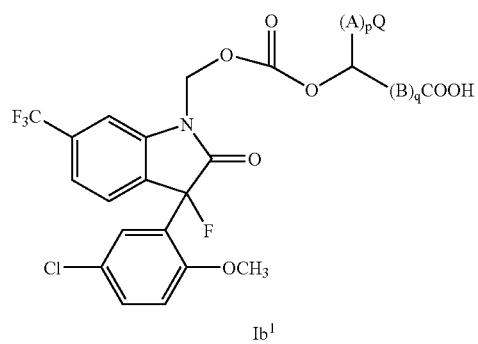

Ib[1]

The preparation of oxidoles of Formula Ia wherein $R_1$, Q, A, B, p and q are as defined herein. Using the general procedure of experimental A, treatment of an amine of Formula II with an alkylating agent such as chlormethyl chloroformate provides chloromethylcarbamate of Formula IIIa. Using general method B, the compound of Formula IV is treated with a chlormethylcarbamate of Formula IIIa to afford a carbamate of Formula Va. Removal of the benzyl groups employing general method C is advantageously effected by hydrogenation using a metal catalyst such as palladium on carbon to provide oxindole of Formula Ia.

The preparation of oxidoles of Formula Ib wherein A, B, Q, p and q are as defined herein. Treatment of an alcohol of Formula IIb with an alkylating agent such as chlormethyl chloroformate provides chloromethylcarbonate of Formula IIIb. The compound of Formula IV is treated with a chlormethyl carbonate of Formula IIIb to afford a carbonate of Formula Vb. Removal of the benzyl groups is advantageously effected by hydrogenation using a metal catalyst such as palladium on carbon to provide oxindole of Formula Ib.

REACTION SCHEME 2

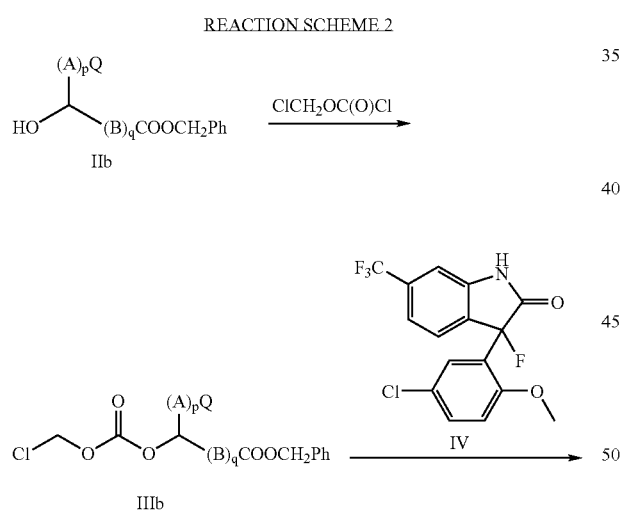

REACTION SCHEME 3

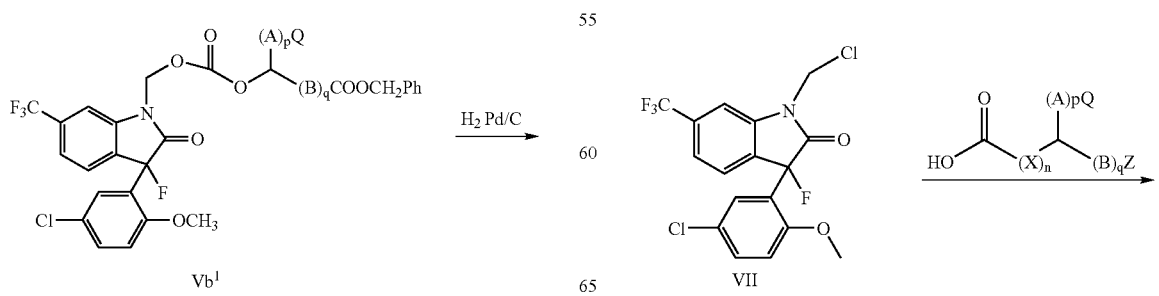

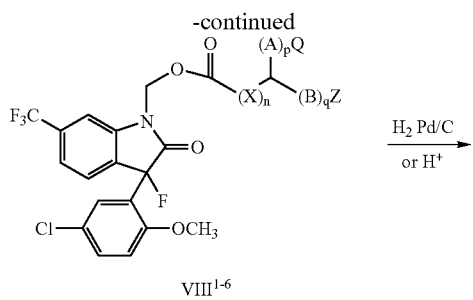

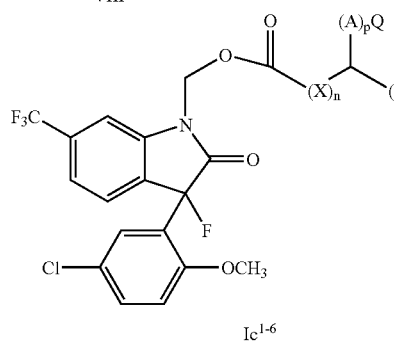

Oxindoles of Formula Ic can be prepared as outlined in Reaction Scheme 3 wherein A, B, Q, Z, n, p and q are as defined herein. Treating oxindole of Formual IV with an acylating agent such a paraformaldedhyde in the presence of base such as potassium carbonate gives hydroxymethyl indole of Formula VI. Chlorination of a compound of Formula VI with a chlorinating agent such as phosphorous trichloride affords chloromethylcarbonate of Formula VII. Displacement of chlorine with a carboxylic acid provides an ester of Formula VIII. If a benzyl group is present in a compound of Formula VIII, it may be removed by hydrogenation using a metal catalyst such as palladium on carbon to provide oxindole of Formula Ic. Alternatively, if a compound of Formula VIII contains a dioxolane, it can be hydrolytically removed in the presence of an acid such as acetic acid to afford a compound of Formula Ic.

Reaction Scheme 4 describes the preparation of Formula Id compounds, wherein A, B, Q, X, n, p, and q are as defined herein. Acylation of oxindole of Formula IV with an an acylating agent such as chlormethylchloroformate gives a chloromethylcarbamate of Formula IX. Displacement of the chlorine with a carboxylic acid yields an ester of Formula X. Removal of the benzyl groups is advantageously effected by hydrogenation using a metal catalyst such as palladium on carbon to provide oxindole of Formula Id.

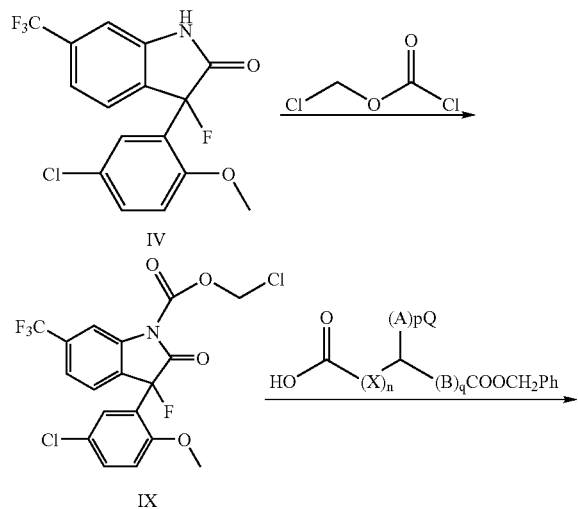

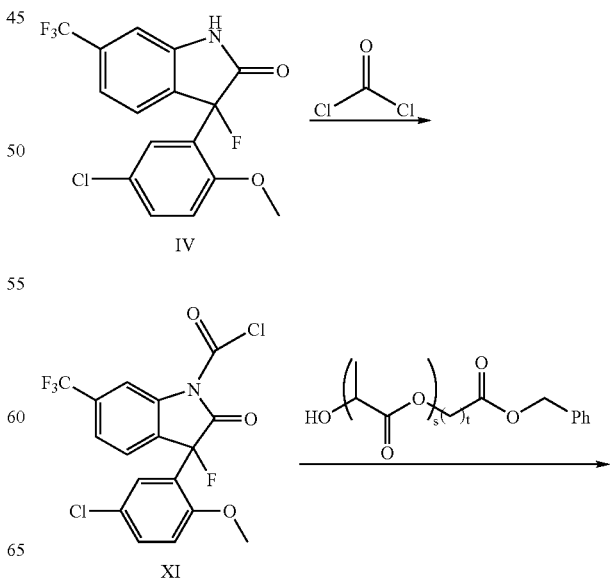

-continued

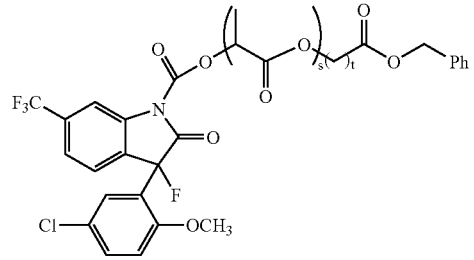

XII[1-3]

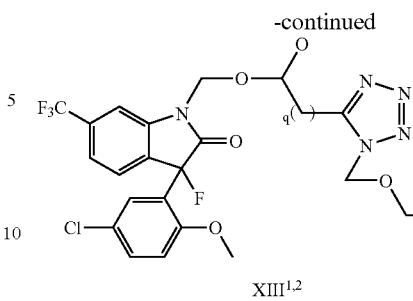

XIII[1,2]

HF →

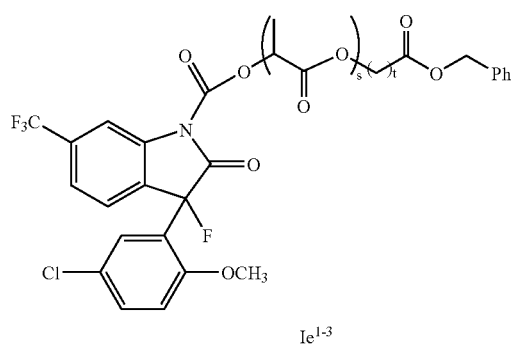

Ie[1-3]

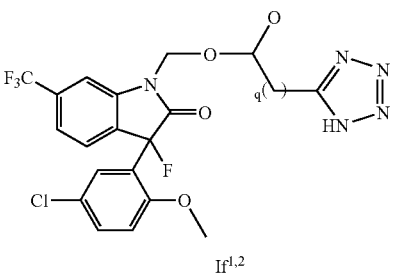

If[1,2]

Reaction Scheme 6 illustrates the synthesis of compounds of Formula If, wherein q is as defined herein. Treatment of a chloromethyl oxindole of Formula VII with a carboxylic acid provides an ester of Formula XIII. Removal of the trimethyl silyl ethoxymethyl group is advantageously effected by using an acid such as hydrogen fluoride affords an oxindole of Formula If.

The preparation of carbamates of Formula Ie are described in Reaction Scheme 5, wherein s is 0 or 1; and t is 0 to 3. Treatment of an oxindole of Formula IV with an acylating agent such as phosgene provides an acyl chloride of Formula XI. Displacement of the chlorine with an alcohol gives a carbamate of Formula XIII. Removal of the benzyl groups is advantageously effected by hydrogenation using a metal catalyst such as palladium on carbon to provide oxindole of Formula Ie.

REACTION SCHEME 7

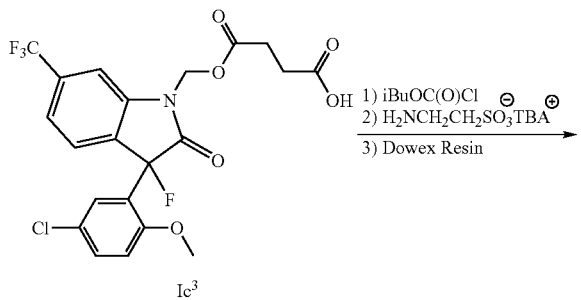

Ic[3]

1) iBuOC(O)Cl
2) H$_2$NCH$_2$CH$_2$SO$_3$TBA
3) Dowex Resin

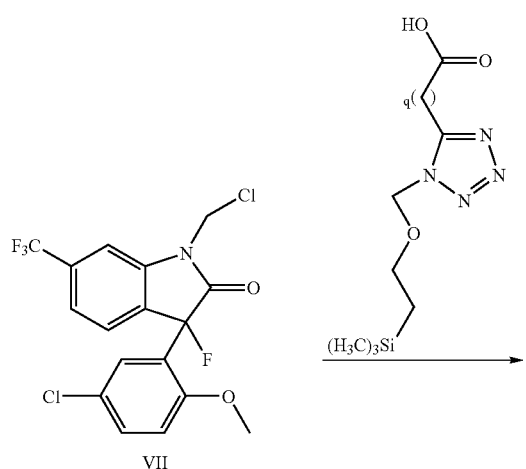

Ig

REACTION SCHEME 6

Compounds of Formula Ig may be prepared as shown in Reaction Scheme 7. Treatment of carboxylic acid of Formula Ic[3] with an acylating agent such as isobutyl chloroformate, followed by treatment with the tetrabutyl ammonium salt of taurine, and then exposure to an ion exchange resin affords sulfates of Formula Ig.

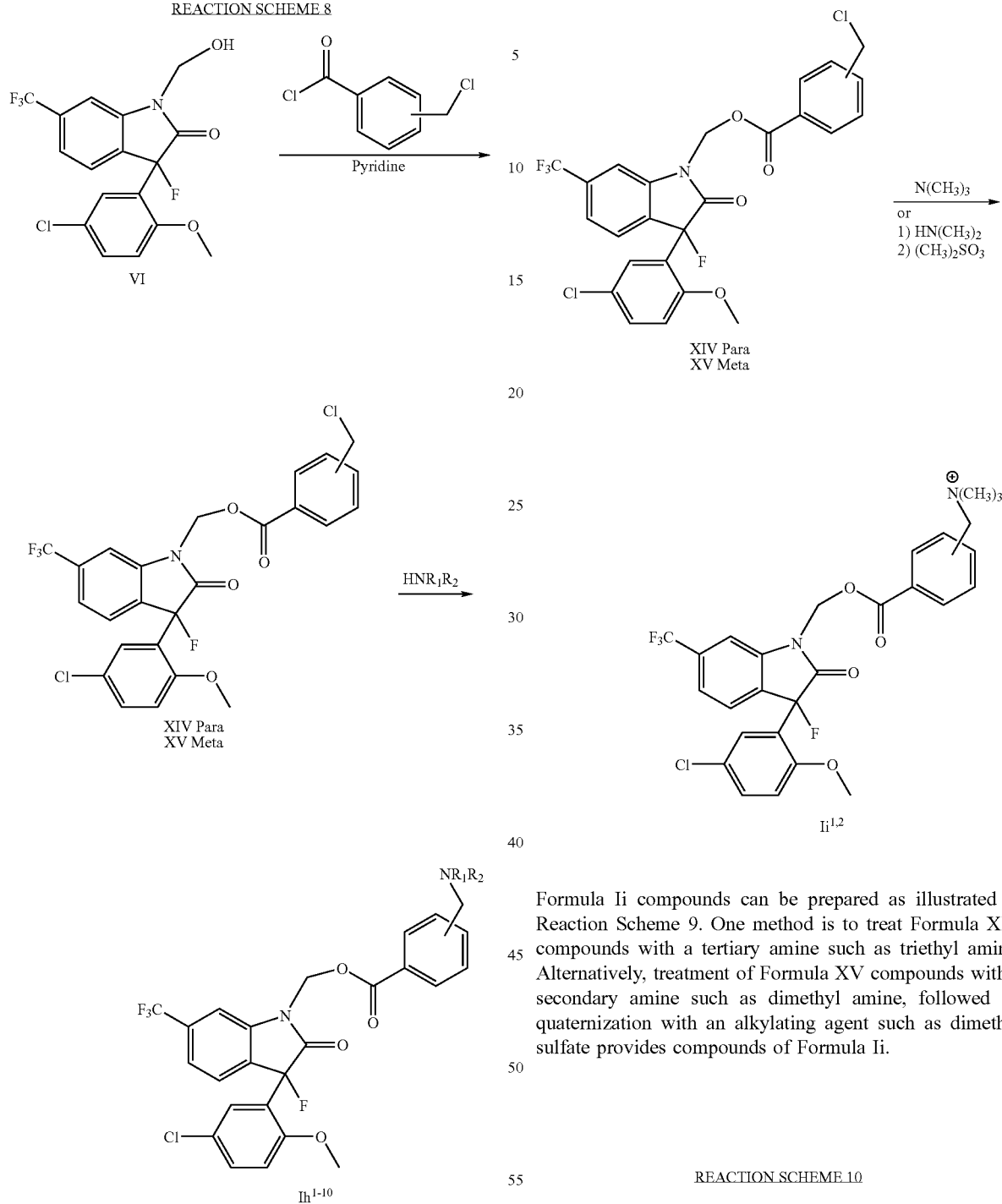

Reaction Scheme 8 depicts preparation of compounds of Formula Ih, wherein $R_1$, and $R_2$ are as defined herein. Acylation of a Formula VI compound with a chloromethyl phenyl acid halide provides chloromethyl aryl esters of Formula XIV and XV. Diplacement of the chlorine with an amine gives Formula Ih compounds.

Formula Ii compounds can be prepared as illustrated in Reaction Scheme 9. One method is to treat Formula XIV compounds with a tertiary amine such as triethyl amine. Alternatively, treatment of Formula XV compounds with a secondary amine such as dimethyl amine, followed by quaternization with an alkylating agent such as dimethyl sulfate provides compounds of Formula Ii.

REACTION SCHEME 10

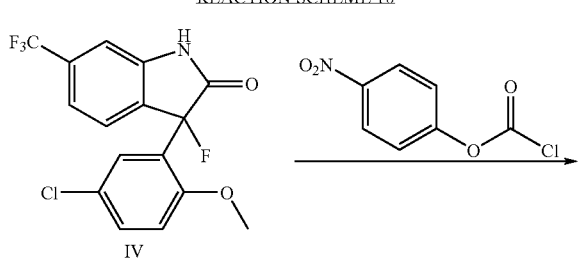

-continued

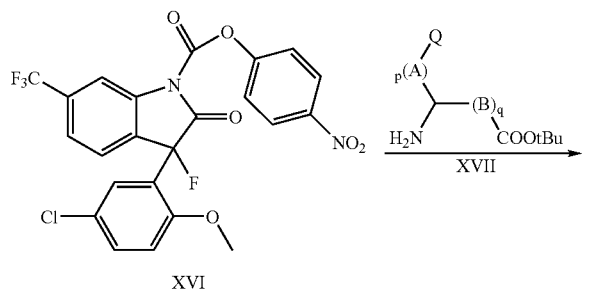

XVI

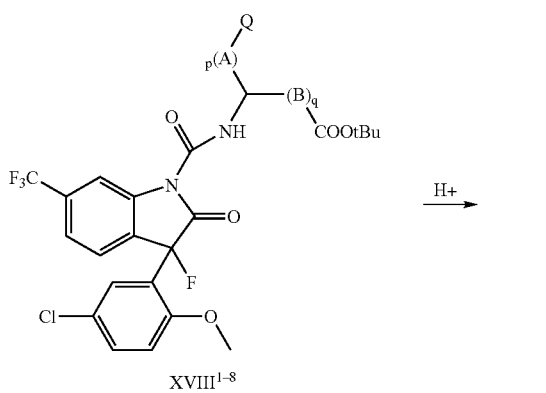

XVIII[1-8]

Reaction Scheme 10 illustrates the preparation of Formula Ij compounds, wherein A, B, Q, p, and q are as defined herein. Acylation of an oxindole of Formula IV with an agent such as p-nitrophenylchloroformate yields a carbamate of Formula XVI. Displacement of p-nitrophenyl with an amine of Formula XVII gives a urea of Formula XVIII. Removal of the t-butyl group is advantageously effected by treatment of a Formula XVIII compound with an acid such as trifluoroacetic acid.

In a preferred embodiment of the invention, the compounds have the Formula I

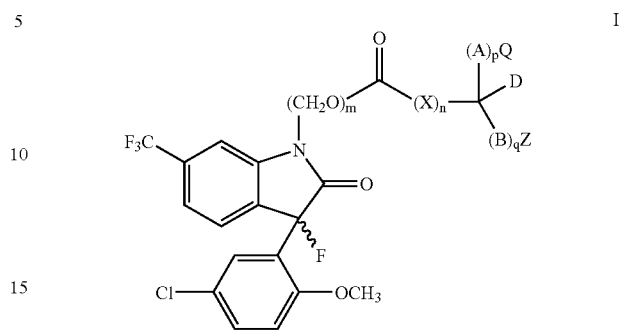

I wherein the wavy bond ($\sim\sim\sim$)

represents the racemate, the (R)-enantiomer or the (S)-enantiomer and m, n, p, q, A, B, D, Q, X, and Z are as defined below, or a nontoxic pharmaceutically acceptable salt or solvate thereof. The N-1 substituted fluorooxindoles of the present invention increase the water solubility of the 3-fluorooxindoles, and thereby decrease the amount of additives that need to be employed to deliver an intravenous dose of the oxindole. Upon systemic administration, the oxindole derivatives are transformed to liberate systemic levels of the fluorooxindole. The present invention also provides pharmaceutical compositions comprising said N-1 substituted fluorooxindoles and to the method of treatment of disorders sensitive to potassium channel opening activity such as ischemia, stroke, convulsions, asthma, epilepsy, irritable bowel syndrome, migraine, traumatic brain injury, spinal cord injury, sexual dysfunction, carbon monoxide poisoning and urinary incontinence.

In a more preferred embodiment of the invention, the compounds have the Formula I'

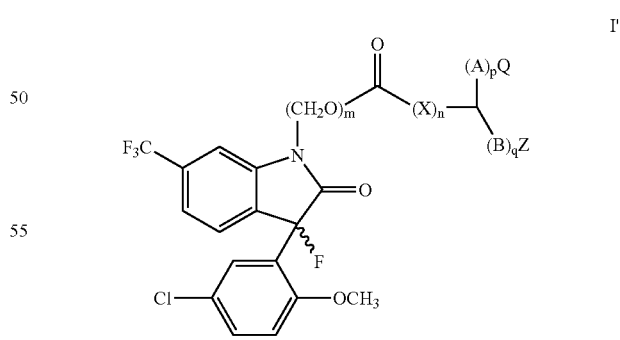

I' wherein the wavy bond ($\sim\sim\sim$)

represents the racemate, the (R)-enantiomer or the (S)-enantiomer; A and B are independently $C_{1-4}$ alkyl or a direct bond; X is O, $CH_2$, phenyl or $(NR_1)_r$; Q and Z are each independently H, $NR_1R_2$, $NR_1$—$CH_2CH_2$—$NR_1R_2$,

—C(O)OH, OH, $OCH_2C(O)OH$, $C(O)OCH_2CO(O)H$, phenyl, piperdinyl, piperizinyl, methylpiperizinyl, morpholinyl or tetrazol-5-yl; m, n, p, q, r are each independently an integer of 0 or 1; and $R_1$, $R_2$, and $R_3$ are each independently H or $C_{1-4}$ alkyl; or a nontoxic pharmaceutically acceptable salt or solvate thereof.

In still a more preferred embodiment of the invention, the wavy bond

represents the (S)-enantiomer in the compounds of Formula I'.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt, solvate or hydrate thereof.

In yet another embodiment, this invention relates to a method for treating ischemia, convulsions, epilepsy, asthma, irritable bowel syndrome, migraine, traumatic brain injury, spinal cord injury, carbon monoxide poisoning, male and female sexual dysfunction, urinary incontinence and especially stroke in a mammal in need thereof, which comprises administering to said mammal a therapeutically effective amount of a compound of Formula I or a nontoxic pharmaceutically acceptable salt, solvate or hydrate thereof.

Biological Activity

Potassium ($K^+$) channels are structurally and functionally diverse families of $K^+$-selective channel proteins which are ubiquitous in cells, indicating their central importance in regulating a number of key cell functions [Rudy, B., Neuroscience, 25, pp. 729–749 (1988)]. While widely distributed as a class, $K^+$ channels are differentially distributed as individual members of this class or as families. [Gehlert, D. R., et al., Neuroscience, 52, pp. 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the large-conductance $Ca^{2+}$-activated $K^+$ channels (BK or BK channels), is regulated by transmembrane voltage, intracellular $Ca^{2+}$, and a variety of other factors such as the phosphorylation state of the channel protein. [Latorre, R., et al., Ann. Rev. Physiol., 51, pp. 385–399 (1989)]. The large, single channel-conductance (generally >150 pS) and high degree of specificity for $K^+$ of BK channels indicates that small numbers of channels could profoundly affect membrane conductance and cell excitability. Additionally, the increase in open probability with increasing intracellular $Ca^{2+}$ indicates involvement of BK channels in the modulation of $Ca^{2+}$-dependent phenomena such as secretion and muscular contraction. [Asano, M., et al., J. Pharmacol. Exp. Ther., 267, pp. 1277–1285 (1993)].

Openers of BK channels exert their cellular effects by increasing the open probability of these channels [McKay, M. C., et al., J. Neurophysiol., 71, pp. 1873–1882 (1994); and Olesen, S.-P., Exp. Opin. Invest. Drugs, 3, pp. 1181–1188 (1994)]. This increase in the opening of individual BK channels collectively results in the hyperpolarization of cell membranes, particularly in depolarized cells, produced by significant increases in whole-cell BK-mediated conductance.

The ability of the compound of Formula IV to open BK channels and increase whole-cell outward ($K^+$) BK-mediated currents was assessed under voltage-clamp conditions by determining their ability to increase cloned mammalian (mSlo or hSlo) BK-mediated outward current heterologously expressed in Xenopus oocytes [Butler, A., et al., Science, 261, pp. 221–224 (1993); and Dworetzky, S. I., et al., Mol. Brain Res., 27, pp. 189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., J. Biol. Chem, 265, pp. 11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compound profiled did not effect non-BK native currents in the oocytes. The compound of Formula IV was shown in at least 5 oocytes at a concentration of 10 μM to increase BK current to 170% of control of IBTX-sensitive current. Recordings were accomplished using standard two-electrode voltage clamp techniques [Stuhmer, W., et al., Methods in Enzymology, 207, pp. 319–339 (1992)]; voltage-clamp protocols consisted of 500–750 ms duration step depolarizations from a holding potential of –60 mV to +140 mV in 20 mV steps. The experimental media (modified Barth's solution) consisted of (in mM): NaCl (88), $NaHCO_3$ (2.4), KCl (1.0), HEPES (10), $MgSO_4$ (0.82), $Ca(NO_3)_2$ (0.33), $CaCl_2$ (0.41); pH 7.5.

The compound of Formula (S)-IV or a prodrug of Formula I was administered intravenous bolus to male Sprague-Dawley rats (n=3 rats/timepoint) at a target dose equivalent to 1 mg/kg of the compound of Formula (S)-IV. At T=0.25, 1 and 2 hours post-dose, whole blood samples were collected and extracted with acetonitrile. Blood extracts were analyzed by LC/MS/MS for levels of the compound of Formula (S)-IV. Table 1 shows a comparison of estimates of truncated 0.25–2 hours AUC of the compound of Formula (S)-IV after administering either the compound of Formula IV or the prodrug of Formula I. For example, as shown in Table 1 following the administration of prodrugs of Formula I, the compound of Formula (S)-IV was detected in the blood of this rat model.

TABLE 1

Rat Blood Levels of Compound (S)-IV after Prodrug Administration

| Compounds of Example | Truncated Blood AUC$_{(0.25-2\ hr)}$ (ng*hr/mL) Compound of Formula (S)-IV |
|---|---|
| Compound of Formula (S)-IV | 261 |
| Example 11 | 155 |
| Example 16 | 168 |

To determine the ability of the compounds of the present invention to reduce cell loss resulting from neuronal ischemia, a standard focal cerebral ischemia is induced by permanent occlusion of the left middle cerebral artery (MCA) and common carotid artery (CCA) with one hour occlusion of the right CCA in the Wistar rat. The surgeries are $_{performed}$ using the sub-temporal approach of A. Tamura, et al., J. Cereb. Blood Flow Metab., 1, pp. 53–60, (1981) and its modifications [K. Osborne, et al., J. Neurol Neurosurg. Psychiatry, 50, pp. 402–410 (1987) and S. Menzies, et al., Neurosurgery, 31, pp. 100–107, (1992).]

The compound of Formula IV was evaluated in the focal stroke model involving permanent occlusion of the left MCA (MCAO) and CCA (CCAO) and temporary occlusion of the right CCA in the Wistar rat [Gribkoff, et al. Nature Med. 7, pp. 471–477 (2001)]. This procedure results in a reliably large neocortical infarct volume that is measured by means of vital dye exclusion in serial slices through the brain 24 hours after MCAO. In the present test, compounds were administered using an i.v. or i.p. route of administration two hours after occlusion. For example, in this model the compound of Formula IV significantly reduced the cortical infarct volume by about 28% when administered intravenously (0.3 mg//kg) as a single bolus two hours after middle cerebral artery occlusion as compared to vehicle-treated control.

To determine the ability of the compounds of the present invention to decrease the amount of neuronal damage following head injury, a standard model of traumatic brain injury is employed. The rat traumatic brain injury (TBI) model is used to evaluate compounds for effectiveness in reversing or preventing the deleterious effects of a concussion-like injury. In general, rats in this model are anesthetized, a craniotomy is performed (surgical opening of the skull), and then saline is injected into the opening to produce a precise pulse of increased intracranial pressure (commonly called a fluid percussion injury). Animals are administered compound at the specified doses at 15 min following trauma. Animals are euthanized 48 hours post TBI.

Moderate diffuse brain injury (defined by McIntosh, et al. Neuroscience, 28:233–44 (1989)) is induced by a fluid-percussion device. The apparatus produces contusion via the rapid injection of a saline pulse [~2.1 to 2.7 atmospheres of pressure (atm)] at a constant duration (21–23 millisecond) into a closed cranial cavity. The saline pulse results in the brief displacement and deformation of the underlying cortex. This model is thought to mimic the clinical situation where a patient experiences a concussion-like injury characterized by brief neurological and systemic physiological alterations without severe structural damage. The fluid percussion device produces brain injury without directly impacting the brain. Diffuse brain injury is achieved by the release of a weighted (4.8 kg) metal pendulum from a predetermined height (McIntosh, et al 1989) that strikes a cork-covered piston at the end of a Plexiglass cylindrical reservoir filled with isotonic saline. Varying volumes of saline is injected into the closed cranial cavity producing a pulse of increased intracranial pressure (ICP). Varying the height of the pendulum controls the magnitude of the injury.

In this experiment the pressure pulses is measured extracranially by a transducer located in the injury device. Following the induction of anesthesia, the trauma screw is tightly connected to the fluid percussion device, and an injury of moderate severity [~2.1 to 2.7 atm], is induced based on a scale established by McIntosh, et al 1989. The pulses are recorded on a storage oscilloscope triggered photoelectrically by descent of the pendulum. Following fluid percussion, the cap created by the trauma screw, the stainless steel screw, and the cranioplastic cement are all removed and the wound closed by non-absorbable suture (3-0). Animals remaining apneic for more than 60 seconds post-injury were immediately euthanatized. Rats are maintained on a water recirculating heating pad until respiration normalized and they are ambulatory. Animals are euthanized and brains removed for assessment of edema at 48 hours by measurement of water content as described previously (McIntosh, et al 1989).

The compound of Formula (S)-IV has previously been shown to produce significant reductions in edema in several regions adjacent to the impact zone [Cheney, et al. J. Cer. Blood Flow & Metab. 21:396–403(2001)].

The results of the above tests demonstrate that the novel oxindoole compounds of the present invention are useful for the treatment of human disorders arising from dysfunction of cellular membrane polarization and conductance and, preferably, are indicated for the treatment of ischemia, stroke, convulsions, epilepsy, asthma, irritable bowel syndrome, migraine, traumatic brain injury, spinal cord injury, carbon monoxide poisoning, sexual dysfunction, and urinary incontinence and other disorders sensitive to BK channel activating activity. Most preferably, the compounds of Formula I are useful in the treatment of cerebral ischemia/stroke.

The compounds of Formula I or pharmaceutical compositions thereof are useful in the treatment, alleviation or elimination of disorders or other disorders associated with the BK channels. Such disorders include ischemia, stroke, convulsions, epilepsy, asthma, irritable bowel syndrome, migraine, traumatic brain injury, spinal cord injury, carbon monoxide poisoning, sexual dysfunction and urinary incontinence and other disorders sensitive to potassium channel openers.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge.

The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 ng/kg to 10 mg/kg body weight. For parenteral administration, the dose may be in the range of 0.1 ng/kg to 10 mg/kg body weight for intravenous administration. The active ingredient will preferably be administered either with a bolus injection or bolus injection followed by continuous infusion; continuously; or in equal doses from one to four times a day.

However, it will be understood that the amount of the compound actually administered will be determined by a physician, in the light of the relevant circumstances, including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the meaning of the invention.

DESCRIPTION OF SPECIFIC EMBODIMENTS

In the following examples, all temperatures are given in degrees Centigrade. Melting points were recorded on a Gallenkamp capillary melting point apparatus temperatures are uncorrected. Proton magnetic resonance ($^1$H NMR), fluorine magnetic resonance ($^{19}$F NMR) and phosphorous magnetic resonance ($^{31}$P NMR) was recorded on a Bruker Advance 400. All spectra were determined in the solvents indicated and chemical shifts are reported in δ units downfield from an internal standard. Interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular (MH$^+$) or (M–H)$^-$ was determined on a Finnigen TSQ 7000. High resolution mass spectra was determined on a Kratos MS50 in FAB mode using cesium iodide/glycerol as internal reference. The element analysis are reported as percent by weight.

The following preparations illustrate procedures for the preparation of intermediates and methods for the preparation of products according to this invention. It should also be evident to those skilled in the art that appropriate substitution of both the materials and methods disclosed herein will produce the examples illustrated below and those encompassed by the scope of this invention.

General Procedure (A) for the Preparation of Chloromethylcarbamates of Amino Acid Benzyl Esters (IIIa)

A solution of the corresponding amino acid hydrochloric or tosylate salt (1 eq) and Et$_3$N (2 eq) in CH$_2$Cl$_2$ was added to a cooled (0° C.) solution of chloromethyl chloroformate (1 eq) in CH$_2$Cl$_2$. The yellowish solution was stirred for 0.5 at rt. and then it was washed with water, brine, dried over MgSO$_4$, filtered and concentrated under reduced pressure. The resulting clear oils were used without further purification.

General Procedure (B) for the Alkylation of (S)-IV with Chloromethylcarbamates of Amino Acid Benzyl Esters Fluorooxindole (S)-IV (1 eq) and the corresponding chloromethylcarbamate (1 eq) were added to a suspension of Cs$_2$CO$_3$ (2 eq) in acetone. The mixture was stirred for 15 h at rt. and concentrated. The remaining residue was redissolved in CH$_2$Cl$_2$, washed with 1N aq. HCl and brine, dried over MgSO$_4$, filtered and concentrated. The remaining yellowish solids were purified by flash chromatography, eluting with EtOAc/Hexanes (1:9)

General Procedure (C) for the Hydrogenation of the Benzyl Esters

The corresponding benzyl ester (1 mmol) was added to a suspension of PtO$_2$ or Pd/C (0.1 mmol) in EtOH/EtOAc (1:1, 40 mL). The flask was flushed with N$_2$ (3×) and a H$_2$ balloon was attached. The black suspension was stirred at rt. for 3 h (or until complete as monitored by thin layer chromatography), filtered through a pad of Celite and concentrated under reduced pressure. The residue was then recrystallyzed from CH$_2$Cl$_2$/Hexanes.

EXAMPLE 1

(S)-2-((((S)-3-(5-chloro-2-methoxyphenyl)-3-fluoro-2-oxo-6-(trifluoromethyl)indolin-1-yl)methoxy)carbonyl)-3-methylbutanoic acid (Ia$^1$)

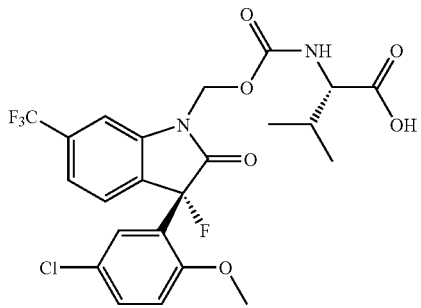

Step A. (S)-2-Chloromethoxycarbonylamino-3-methylbutyric acid benzyl ester.

Prepared by general procecure (A). A solution of chloromethyl chloroformate (0.18 mL, 2.05 mmol) in CH$_2$Cl$_2$ (10 mL) and a solution of valine benzyl ester hydrochloride (0.5 g, 2.05 mmol) and Et$_3$N (0.57 mL, 4.1 mmol) in CH$_2$Cl$_2$ (15 mL) were combined according to general procedure (A). After work-up a clear oil was obtained (0.58 g, 95% yield). $^1$H NMR (500 MHz, CDCl$_3$): δ 0.85 (d, J=6.72 Hz, 3 H), 0.85 (d, J=6.72 Hz, 3 H), 2.21 (m, 1 H), 4.36 (dd, J=9.15, 4.58 Hz, 1 H), 5.16 (d, J=12.2 Hz, 1H), 5.20 (d, J=12.2 Hz, 1 H) 5.49 (bd, J=8.55 Hz, 1 H), 5.71 (d, J=6.10 Hz, 1 H), 5.77 (d, J=6.10 Hz, 1 H), 7.32–7.87 (m, 5H). $^{13}$C NMR (125 MHz, CDCl$_3$): δ 171.3, 153.6, 135.13, 128.7, 128.6, 128.4, 70.6, 67.3, 59.1, 31.4, 18.9, 17.3.

Step B. (S)-2-((((S)-3-(5-chloro-2-methoxyphenyl)-3-fluoro-2-oxo-6-(trifluoromethyl)indolin-1-yl)methoxy)carbonyl)-3-methylbutanoic acid benzyl ester (V$^1$).

Fluorooxindole (S)-IV (0.70 g, 1.95 mmol) and the chloromethylcarbamate of valine benzyl ester (0.58 g, 1.95 mmol) were added to a suspension of Cs$_2$CO$_3$ (1.40 g, 3.90 mmol) in acetone (30 ml) according to general procedure (B). After work-up and purification, the title compound was isolated as a white solid (0.71 g, 58% yield). $^1$H NMR (500 MHz, CDCl$_3$): δ 0.82 (d, J=7.01 Hz, 3 H), 0.93 (d, J=7.01 Hz, 3 H), 2.20 (m, 1H), 3.47 (s, 3H), 4.39 (dd, J=9.16, 4.58 Hz, 1 H), 5.16 (d, J=12.1 Hz, 1 H), 5.19 (d, J=12.2 Hz, 1 H), 5.35 (d, J=9.15 Hz, 1 H), 5.84 (d, J=11.3 Hz, 1 H), 5.91 (d, J=11.3 Hz, 1 H), 6.73 (d, J=8.85 Hz, 1 H), 7.24 (d, J=7.93 Hz, 1 H), 7.30–7.38 (m, 7 H), 7.50 (s, 1 H), 7.79 (d, J=2.14 Hz, 1 H). LRMS: 645 (M+Na), 640 (M+NH$_4$). HRMS Calculated 645.1391 (M+Na). found 645.1403. mp=64–65° C. (decomposed).

Step C. (S)-2-((((S)-3-(5-chloro-2-methoxyphenyl)-3-fluoro-2-oxo-6-(trifluoromethyl)indolin-1-yl)methoxy)carbonyl)-3-methylbutanoic acid (Ia$^1$).

The valine benzyl ester derivative (0.20 g, 0.32 mmol) was hydrogenated according to the general procedure (C). After work-up and purification, the title compound was isolated as a white solid (0.15 g, 88% yield). $^1$H NMR (500 MHz, DMSO): δ 0.84 (d, J=6.72 Hz, 3 H), 0.86 (d, J=6.72 Hz, 3 H), 2.05 (m, 1H), 3.51 (s, 3H), 3.92 (dd, J=8.55, 5.08 Hz, 1 H), 5.85 (d, J=11.6 Hz, 1 H), 5.89 (d, J=11.6 Hz, 1 H), 7.07 (d, J=8.85 Hz, 1 H), 7.46 (s, 2 H), 7.52 (dd, J=8.85, 2.44 Hz, 1 H), 7.71 (d, J=2.14 Hz, 1 H), 7.74 (s, 1 H), 7.87 (d, J=8.58 Hz, 1 H), 12.63 (bs, 1 H). LRMS: 555 (M+Na), 550 (M+NH$_2$). HRMS Calculated 555.0922 (M+Na). found 555.0929. mp=150–151° C. (decomposed).

EXAMPLE 2

(S)-2-((((S)-3-(5-chloro-2-methoxyphenyl)-3-fluoro-2-oxo-6-(trifluoromethyl)indolin-1-yl)methoxy)carbonyl)succinic acid (Ia$^2$)

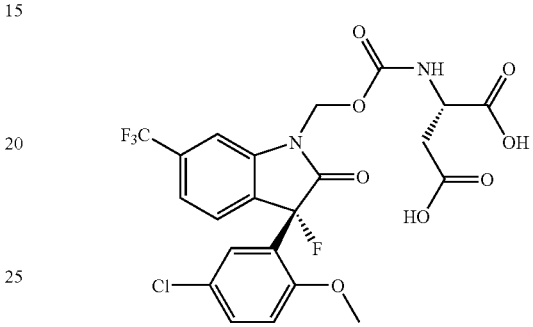

Step A. (S)-2-Chloromethoxycarbonylamino-succinic acid dibenzyl ester.

A solution of chloromethyl chloroformate (0.14 mL, 1.54 mmol) in CH$_2$Cl$_2$ (10 mL) and a solution of aspartic acid dibenzyl ester tosylate (0.75 g, 1.54 mmol) and Et$_3$N (0.43 mL, 3.08 mmol) in CH$_2$Cl$_2$ (15 mL) were combined according to general procedure (A). After work-up a clear oil was obtained (0.59 g, 94% yield). $^1$H NMR (500 MHz, CDCl$_3$): δ 2.93 (dd, J=17.10, 4.57 Hz, 1 H), 3.11 (dd, J=17.10, 4.57 Hz, 1 H), 4.70 (m, 1 H), 5.08 (s, 2 H), 5.16 (s, 2 H), 5.70 (d, J=6.10 Hz, 1 H), 5.77 (d, J=6.10 Hz, 1 H), 6.04 (d, J=8.45 Hz, 1 H), 7.29–7.38 (m, 10 H).

Step B. (S)-2-((((S)-3-(5-chloro-2-methoxyphenyl)-3-fluoro-2-oxo-6-(trifluoromethyl)indolin-1-yl)methoxy)carbonyl)succinic acid dibenzyl ester (Va$^2$).

Fluorooxindole (S)-IV (0.67 g, 1.88 mmol) and the chloromethylcarbamate of glutamic acid dibenzyl ester (0.80 g, 1.91 mmol) were added to a suspension of Cs$_2$CO$_3$ (1.35 g, 3.82 mmol) in acetone (30 ml) according to general procedure (B). After work-up and purification, the title compound was isolated as a clear oil (0.51 g, 37% yield). $^1$H NMR (500 MHz, CDCl$_3$): δ 2.06 (m, 1 H), 2.26 (m, 1 H), 2.40 (m, 2 H), 3.44 (s, 3 H), 4.48 (m, 1 H), 5.07 (s, 2 H), 5.16 (s, 2 H), 5.58 (d, J=7.94 Hz, 1 H), 5.77 (d, J=10.99 Hz, 1 H), 5.90 (d, J=10.99 Hz, 1 H), 6.70 (d, J=8.85 Hz, 1 H), 7.23 (d, J=7.23 Hz, 1 H), 7.28–7.38 (m, 11 H), 7.47 (s, 1 H), 7.79 (d, J=1.83 Hz, 1 H). LRMS: 741 (M–H), 760 (M+NH$_4$), 765 (M+Na). HRMS Calculated 765.1603 (M+Na). found 765.1578.

Step C. (S)-2-((((S)-3-(5-chloro-2-methoxyphenyl)-3-fluoro-2-oxo-6-(trifluoromethyl)indolin-1-yl)methoxy)carbonyl)succinic acid (Ia$^2$).

The aspartic acid dibenzyl ester derivative (0.12 g, 0.16 mmol) was hydrogenated according to general procdure (C). After work-up and purification, the title compound was isolated as a white solid (85 mg, 97% yield). $^1$H NMR (500 MHz, DMSO): δ 2.56 (dd, J=16.12, 6.71 Hz, 1 H), 2.72 (m, J=16.12, 4.91 Hz, 3 H), 3.48 (s, 3H), 4.35 (m, 1 H), 5.83 (d, J=11.6 Hz, 1 H), 5.87 (d, J=11.6 Hz, 1 H), 7.07 (d, J=8.85 Hz, 1 H), 7.46 (s, 2 H), 7.52 (dd, J=8.85, 2.44 Hz, 1 H), 7.71

EXAMPLE 3

(S)-2-((((S)-3-(5-chloro-2-methoxyphenyl)-3-fluoro-2-oxo-6-(trifluoromethyl)indolin-1-yl)methoxy)carbonyl)propanoic acid (Ia$^3$)

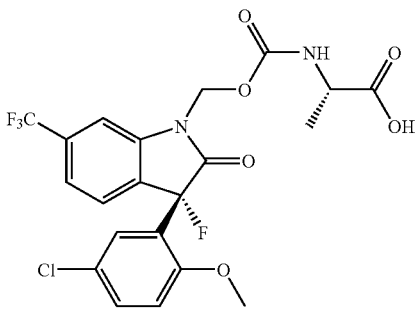

Step A. (S)-2-Chloromethoxycarbonylamino-propionic acid benzyl ester.

A solution of chloromethyl chloroformate (0.20 mL, 2.30 mmol) in CH$_2$Cl$_2$ (10 mL) and a solution of alanine benzyl ester hydrochloride (0.50 g, 2.30 mmol) and Et$_3$N (0.64 mL, 4.60 mmol) in CH$_2$Cl$_2$ (15 mL) were combined according to general procedure (A). After work-up a clear oil was obtained (0.57 g, 91% yield). $^1$H NMR (500 MHz, CDCl$_3$): δ 1.56 (d, J=7.56 Hz, 3 H), 4.45 (m, 1 H), 5.17 (d, J=12.14 Hz, 1 H), 5.21 (s, J=12.14 Hz, 1 H), 5.68 (bs, 1 H), 5.71 (d, J=6.11 Hz, 1 H), 5.76 (d, J=6.11 Hz, 1 H), 7.32–7.39 (m, 5 H).

Step B. (S)-2-((((S)-3-(5-chloro-2-methoxyphenyl)-3-fluoro-2-oxo-6-(trifluoromethyl)indolin-1-yl)methoxy)carbonyl)propanoic acid benzyl ester (Va$^3$).

Fluorooxindole (S)-IV (0.74 g, 2.06 mmol) and the chloromethyl-carbamate of valine benzyl ester (0.56 g, 2.06 mmol) were added to a suspension of Cs$_2$CO$_3$ (1.47 g, 4.16 mmol) in acetone (30 ml) according to general procedure (B). After work-up and purification, the title compound was isolated as a white solid (0.53 g, 43% yield). $^1$H NMR (500 MHz, CDCl$_3$): δ 1.44 (d, J=7.02 Hz, 3 H), 3.45 (s, 3 H), 4.45 (m, 1 H), 5.16 (d, J=12.20 Hz, 1 H), 5.19(s, J=12.20 Hz, 1 H), 5.71 (bs, 1 H), 5.81 (d, J=10.90 Hz, 1 H), 5.88 (d, J=10.9 Hz, 1 H), 6.72 (d, J=8.55 Hz, 1 H), 7.23 (d, J=7.63 Hz, 1 H), 7.30–7.86 (m, 7 H), 7.55 (s, 1 H), 7.78 (d, J=1.83 Hz, 1 H). LRMS: 617 (M+Na), 612 (M+NH$_4$) 5.95. (M+H), 593 (M–H). HRMS Calculated 617.1078 (M+Na). found 617.1086. mp=75–78° C. (decomposed).

Step C. (S)-2-((((S)-3-(5-chloro-2-methoxyphenyl)-3-fluoro-2-oxo-6-(trifluoromethyl)indolin-1-yl)methoxy)carbonyl)propanoic acid (Ia$^3$).

The alanine benzyl ester derivative (0.20 g, 0.34 mmol) was hydrogenated according to the general procedure (C). After work-up and purification, the title compound was isolated as a white solid (0.13 g, 76% yield). $^1$H NMR (500 MHz, DMSO): δ 1.26 (d, J=7.33 Hz, 3 H), 3.51 (s, 3 H), 4.04 (m, 1 H), 5.85 (s, 2 H), 7.08 (d, J=9.15 Hz, 1 H), 7.46 (s, 2 H), 7.52 (dd, J=2.75, 8.85 Hz, 1 H), 7.71 (d, J=2.45 Hz, 1 H), 7.73 (s, 1 H), 7.92 (d, J=7.63 Hz, 1 H), 12.57 (s, 1 H). LRMS: 527 (M+Na). HRMS Calculated 503.0633 (M–H). found 503.0642.

EXAMPLE 4

(S)-3-(((3-(5-chloro-2-methoxyphenyl)-3-fluoro-2-oxo-6-(trifluoromethyl)-indolin-1-yl)methoxy)carbonyl)propanoic acid (Ia$^4$)

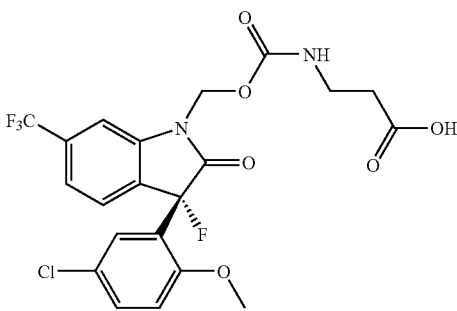

Step A. 3-Chloromethoxycarbonylamino-propionic acid benzyl ester.

A solution of chloromethyl chloroformate (0.27 mL, 3.1 mmol) in CH$_2$Cl$_2$ (20 mL) and a solution of beta alanine benzyl ester tosylate (1.00 g, 2.84 mmol) and Et$_3$N (0.83 mL, 5.94 mmol) in CH$_2$Cl$_2$ (20 mL) were combined according to general procedure (A). After work-up a clear oil was obtained (0.73 g, 95% yield). $^1$H NMR (500 MHz, CDCl$_3$): δ 2.62 (t, J=6.10 Hz, 2 H), 3.51 (q, J=6.10 Hz, 2 H), 5.14 (s, 2 H), 5.56 (bs, 1 H), 5.73 (s, 2 H), 7.32–7.39 (m, 5 H).

Step B. (S)-3-(((3-(5-chloro-2-methoxyphenyl)-3-fluoro-2-oxo-6-(trifluoromethyl)-indolin-1-yl)methoxy)carbonyl) propanoic acid benzyl ester (Va$^4$).

Fluorooxindole (S)-IV (0.97 g, 2.69 mmol) and the chloromethylcarbamate of beta alanine benzyl ester (0.73 g, 2.69 mmol) were added to a suspension of Cs$_2$CO$_3$ (1.89 g, 5.38 mmol) in acetone (35 ml) according to general procedure (B). After work-up and purification, a clear oil was isolated (0.69 g, 43% yield). $^1$H NMR (500 MHz, CDCl$_3$): δ 2.73 (m, 4 H), 3.50 (s, 3 H), 5.12 (s, 2 H), 5.84 (d, J=10.99 Hz, 1 H), 5.90 (d, J=10.99 Hz, 1 H), 6.75 (d, J=8.55 Hz, 1 H), 7.25 (d, J=7.63 Hz, 1 H), 7.32–7.39 (m, 7 H), 7.80 (d, J=2.44 Hz, 1 H), LRMS: 597 (M+NH$_4$). HRMS Calculated 602.0969 (M+Na). found 602.0972

STEP C. (S)-3-(((3-(5-chloro-2-methoxyphenyl)-3-fluoro-2-oxo-6-(trifluoromethyl)indolin-1-yl)methoxy)carbonyl)propanoic acid (Ia$^4$).

The beta alanine benzyl ester derivative (0.43 g, 0.72 mmol) was hydrogenated according to the general procedure (C). After work-up and purification, the title compound was isolated as a white solid (0.35 g, 96% yield). $^1$H NMR (500 MHz, DMSO): δ 2.39 (t, J=7.01 Hz, 2 H), 3.22 (apq, J=6.71 Hz, 2 H), 3.48 (s, 3 H), 5.81 (d, J=11.59 Hz, 1 H), 5.84 (d, J=11.59 Hz, 1 H), 7.07 (dd, J=1.22, 9.16 Hz, 1 H), 7.45 (s, 2 H), 7.52 (dd, J=2.44, 8.85 Hz, 1 H), 7.61 (t, J=5.56 Hz, 1 H), 7.71 (d, J=2.44 Hz, 1 H), 7.74 (s, 1 H), 12.14 (bs, 1 H). LRMS: 503 (M–H), 522 (M+NH$_4$). HRMS Calculated 503.0633 (M–H). found 503.0631.

EXAMPLE 5

(S)-2-(((3-(5-chloro-2-methoxyphenyl)-3-fluoro-2-oxo-6-(trifluoromethyl)-indolin-1-yl)methoxy)carbonyl)acetic acid (Ia$^5$)

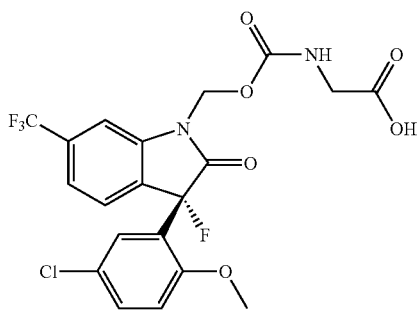

Step A. Chloromethoxycarbonylamino-acetic acid benzyl ester.

A solution of chloromethyl chloroformate (0.20 mL, 2.30 mmol) in CH$_2$Cl$_2$ (10 mL) and a solution of glycine benzyl ester hydrochloride (0.48 g, 2.30 mmol) and Et$_3$N (0.64 mL, 4.60 mmol) in CH$_2$Cl$_2$ (15 mL) were combined according to general procedure (A). After work-up a clear oil was obtained (0.55 g, 93% yield). $^1$H NMR (500 MHz, CDCl$_3$): δ 4.05 (d, J=5.49 Hz, 2 H), 5.19 (s, 2 H), 5.56 (bs, 1 H), 5.74 (s, 2 H), 7.34–7.39 (m, 5 H).

Step B. (S)-2-(((3-(5-chloro-2-methoxyphenyl)-3-fluoro-2-oxo-6-(trifluoromethyl)-indolin-1-yl)methoxy)carbonyl) acetic acid benzyl ester (Va$^5$).

Fluorooxindole (S)-IV (0.75 g, 2.08 mmol) and the chloromethylcarbamate of glycine benzyl ester (0.55 g, 2.13 mmol) were added to a suspension of Cs$_2$CO$_3$ (1.50 g, 4.26 mmol) in acetone (30 ml) according to general procedure (B). After work-up and purification, the title compound was isolated as a white solid (0.47 g, 38% yield). $^1$H NMR (500 MHz, CDCl$_3$): δ 3.44 (s, 3 H), 4.03 (dd, J=3.06, 5.56 Hz, 1 H), 5.16 (s, 2 H), 5.74 (t, J=5.56, 1 H), 5.81 (d, J=11.29 Hz, 1 H), 5.87 (d, J=11.29 Hz, 1 H), 6.71 (d, J=8.55 Hz, 1 H), 7.22 (d, J=7.63 Hz, 1 H), 7.30–7.36 (m, 8 H), 7.59 (s, 1 H), 7.78 (d, J=1.83 Hz, 1 H). LRMS: 603 (M+Na), 598 (M+NH$_4$) 581 (M+H), 579 (M−H). HRMS Calculated 603.0922 (M+Na). found 603.0928. mp=70–75° C. (decomposed).

Step C. (S)-2-(((3-(5-chloro-2-methoxyphenyl)-3-fluoro-2-oxo-6-(trifluoromethyl)indolin-1-yl)methoxy)carbonyl) acetic acid (Ia$^5$).

The glycine benzyl ester derivative (0.22 g, 0.38 mmol) was hydrogenated according to the general procedure (C). After work-up and purification, the title compound was isolated as a white solid (0.15 g, 80% yield). $^1$H NMR (500 MHz, DMSO): δ 3.51 (s, 3 H), 3.69 (d, J=6.11 Hz, 2 H), 5.85 (s, 2 H), 7.08 (d, J=8.54 Hz, 1 H), 7.46 (s, 2 H), 7.52 (dd, J=2.45, 8.85 Hz, 1 H), 7.71 (d, J=2.45 Hz, 1 H), 7.73 (s, 1 H), 7.87 (t, J=6.10 Hz, 1 H), 12.58 (s, 1 H). LRMS: 513 (M+Na). HRMS Calculated 489.0476 (M−H). found 489.0482.

EXAMPLE 6

(S)-1-((((S)-3-(5-chloro-2-methoxyphenyl)-3-fluoro-2-oxo-6-(trifluoromethyl)-indolin-1-yl)methoxy) carbonyl)pyrrolidine-2-carboxylic acid (Ia$^6$)

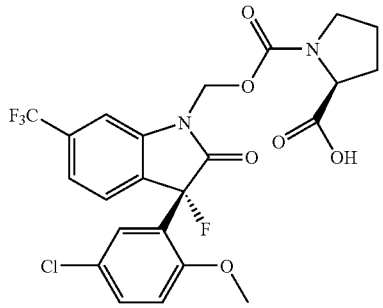

Step A. (S)-2-benzyl 1-chloromethyl pyrrolidine-1,2-dicarboxylate.

A solution of chloromethyl chloroformate (0.184 mL, 2.10 mmol) in CH$_2$Cl$_2$ (10 mL) and a solution of proline benzyl ester hydrochloride (0.5 g, 2.10 mmol) and Et$_3$N (0.57 mL, 4.2 mmol) in CH$_2$Cl$_2$ (15 mL) were combined according to general procedure (A). After work-up a clear oil was obtained (0.58 g, 93% yield) and it was used without futher purification. $^1$H NMR (500 MHz, CDCl$_3$): δ 1.91 (m, 2 H), 2.03 (m, 1 H), 2.23 (m, 1 H), 3.53 (m, 1 H), 3.63 (m, 1 H), 4.40 and 4.46 (dd, J=3.6, 8.6 Hz, 1 H), 5.14 (dd, J=4.71, 12.2 Hz, 1 H), 5.20 (d, J=12.11, 1 H), 5.21 and 5.71 (d, J=6.03 Hz, 1 H), 5.68 and 5.87 (d, J=5.98 Hz, 1 H), 7.26–7.38 (m, 5H).

Step B. (S)-1-((((S)-3-(5-chloro-2-methoxyphenyl)-3-fluoro-2-oxo-6-(trifluoromethyl)-indolin-1-yl)methoxy)carbonyl)pyrrolidine-2-carboxylic acid methyl] ester (Va$^6$).

Fluorooxindole (S)-IV (0.60 g, 1.68 mmol) and the chloromethylcarbamate of proline benzyl ester (0.50 g, 1.68 mmol) were added to a suspension of Cs$_2$CO$_3$ (1.18 g, 3.36 mmol) in acetone (30 ml) according to general procedure (B). After work-up and purification, the title compound was isolated as a clear oil (0.74 g, 71% yield). $^1$H NMR (500 MHz, CHCl$_3$, obtained as a 1:1 mixture of rotomers): δ 1.93 (m, 3 H), 2.03 (m, 3 H), 2.21 (m, 2 H), 3.40 (s, 3 H), 3.48 (s, 3 H), 3.59 (m, 2 H), 3.68 (m, 1 H), 4.32 (dd, J=3.66, 8.54 Hz, 1 H), 4.48 (dd, J=3.66, 8.54 Hz, 1 H), 4.93 (d, J=12.20, 1 H), 5.02 (d, J=12.20, 1 H), 5.18 (m, 2 H), 5.64 (d, J=10.64 Hz, 1 H), 5.88 (d, J=10.64 Hz, 1 H), 5.97 (dd, J=2.45, 10.99 Hz, 2 H), 6.69 (d, J=8.85 Hz, 1 H), 6.74 (d, J =8.85 Hz, 1 H), 7.17 (m, 2 H), 7.24 (m, 2 H), 7.31–7.39 (m, 10 H), 7.45 (s, 1 H), 7.53 (s, 1 H). LRMS: 644 (M+Na).

Step C. (S)-1-((((S)-3-(5-chloro-2-methoxyphenyl)-3-fluoro-2-oxo-6-(trifluoromethyl)-indolin-1-yl)methoxy)carbonyl)pyrrolidine-2-carboxylic acid (Ia$^6$).

The proline benzyl ester derivative (0.70 g, 1.12 mmol) was hydrogenated according to the general procedure (C). After work-up and purification, the title compound was isolated as a white solid (0.52 g, 87% yield). $^1$H NMR (500 MHz, DMSO): δ 1.66 (m, 3 H), 2.21 (m, 1 H), 3.40 (m, 3 H), 3.47 (s, 3 H), 4.21 (m, 1 H), 5.85 (m, 2 H), 7.07 (m, 1 H), 7.45 (d, J=6.11 Hz, 2 H), 7.53 (m, 1 H), 7.71 (d, J=2.45 Hz, 1 H), 7.75 (s, 1 H), 12.68 (s, 1 H). LRMS: 548 (M+NH$_4$), 553 (M+Na), 531 (M+H), 529 (M−H). HRMS Calculated 553.0765 (M+Na). found 553.0778.

EXAMPLE 7

(2S,3S)-2-((((S)-3-(5-chloro-2-methoxyphenyl)-3-fluoro-2-oxo-6-(trifluoromethyl)indolin-1-yl)methoxy)carbonyl)-3-methylpentanoic acid (Ia⁷)

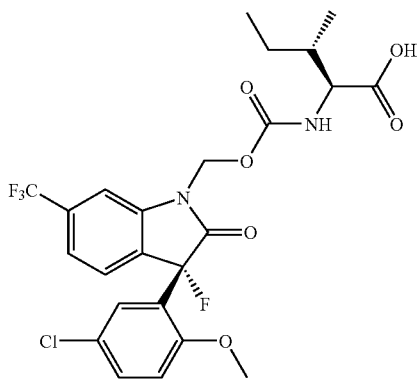

Step A. (S)-2-Chloromethoxycarbonylamino-3-methylpentanoic acid benzyl ester.

A solution of chloromethyl chloroformate (0.23 mL, 2.49 mmol) in CH$_2$Cl$_2$ (20 mL) and a solution of isolucine benzyl ester tosylate (0.98 g, 2.49 mmol) and Et$_3$N (0.76 mL, 5.08 mmol) in CH$_2$Cl$_2$ (20 mL) were combined according to general procedure (A). After work-up a clear oil was obtained (0.78 g, 99% yield). $^1$H NMR (500 MHz, CDCl$_3$): δ 0.84 (t, J=7.32 Hz, 3 H), 0.91 (d, J=7.02 Hz, 3 H), 1.16 (m, 1 H), 1.36 (m, 1 H), 1.93 (m, 1 H), 4.40 (dd, J=4.58, 9.16 Hz, 1 H), 5.15 (d, J=12.20 Hz, 1 H), 5.21 (d, J=12.20 Hz, 1 H), 5.51 (d, J=8.85 Hz, 1 H), 5.71 (d, J=8.85 Hz, 1 H), 5.76 (d, J=8.85 Hz, 1 H), 7.34–7.39 (m, 5 H).

STEP B. (2S,3S)-2-((((S)-3-(5-chloro-2-methoxyphenyl)-3-fluoro-2-oxo-6-(trifluoromethyl)indolin-1-yl)methoxy)carbonyl)-3-methylpentanoic acid benzyl ester (Va⁷).

Fluorooxindole (S)-IV (0.86 g, 2.40 mmol) and the chloromethylcarbamate of beta alanine benzyl ester (0.78 g, 2.45 mmol) were added to a suspension of Cs$_2$CO$_3$ (1.73 g, 4.90 mmol) in acetone (35 ml) according to general procedure (B). After work-up and purification, the title compound was isolated as a clear oil (0.55 g, 36% yield). $^1$H NMR (500 MHz, CDCl$_3$): δ 0.84 (t, J=7.32 Hz, 3 H), 0.90 (d, J=6.71 Hz, 3 H), 1.16 (m, 1 H), 1.36 (m, 1 H), 1.93 (m, 1 H), 3.46 (s, 3 H), 4.42 (dd, J=4.58, 8.85 Hz, 1 H), 5.15 (d, J=12.20 Hz, 1 H), 5.20 (d, J=12.20 Hz, 1 H), 5.35 (d, J=8.85 Hz, 1 H), 5.83 (d, J=11.95 Hz, 1 H), 5.91 (d, J=11.95 Hz, 1 H), 6.73 (d, J=8.85 Hz, 1 H), 7.23 (dd, J=2.45, 7.63, Hz, 1 H), 7.34–7.39 (m, 7 H), 7.50 (s, 1 H), 7.79 (d, J=2.45 Hz, 1 H). LRMS: 659 (M+Na). HRMS Calculated 659.1548 (M+Na). found 659.1548.

STEP C. (2S,3S)-2-((((S)-3-(5-chloro-2-methoxyphenyl)-3-fluoro-2-oxo-6-(trifluoromethyl)indolin-1-yl)methoxy)carbonyl)-3-methylpentanoic acid (Ia⁷).

The isolucine benzyl ester derivative (0.32 g, 0.59 mmol) was hydrogenated according to the general procedure (C). After work-up and purification, the title compound was isolated as a white solid (0.28 g, 86% yield). $^1$H NMR (500 MHz, DMSO): δ 0.80 (t, J=7.32 Hz, 3 H), 0.84 (d, J=7.04 Hz, 3 H), 1.16 (m, 1 H), 1.36 (m, 1 H), 1.78 (m, 1 H), 3.50 (s, 3 H), 3.95 (dd, J=6.10, 6.55 Hz, 1 H), 5.85 (d, J=11.60 Hz, 1 H), 5.88 (d, J=11.60 Hz, 1 H), 7.08 (d, J=8.85 Hz, 1 H), 7.46 (s, 2 H), 7.62 (dd, J=2.74, 5.85 Hz, 1 H), 7.70 (d, J=2.74 Hz, 2 H), 7.74 (s, 1 H), 7.87 (d, J=8.24 Hz, 1 H), 12.58 (bs, 1 H). LRMS: 569 (M+Na), 564 (M+NH$_4$), 545 (M−H). HRMS Calculated 545.1102 (M−H). found 545.1086. mp=93–94° C. (decomposed).

EXAMPLE 8

(S)-2-((((S)-3-(5-chloro-2-methoxyphenyl)-3-fluoro-2-oxo-6-(trifluoromethyl)indolin-1-yl)methoxy)carbonyl)pentanedioic acid (Ia⁸)

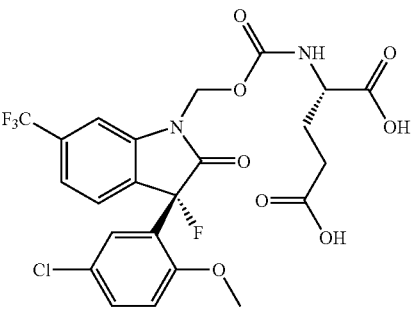

Step A. (S)-Chloromethoxycarbonylamino-pentanedioic acid dibenzyl ester.

A solution of chloromethyl chloroformate (0.17 mL, 2.00 mmol) in CH$_2$Cl$_2$ (20 mL) and a solution of glutamic acid dibenzyl ester tosylate (1.00 g, 2.00 mmol) and Et$_3$N (0.56 mL, 4.00 mmol) in CH$_2$Cl$_2$ (20 mL) were combined according to general procedure (A). After work-up a clear oil was obtained (0.80 g, 98% yield). $^1$H NMR (500 MHz, CDCl$_3$): δ 2.06 (m, 1 H), 2.26 (m, 1 H), 2.44 (m, 2 H), 4.48 (bq, J=7.93 Hz, 1 H), 5.11 (s, 2 H), 5.18 (s, 2 H), 5.69 (d, J=6.10 Hz, 1 H), 5.73 (d, J=6.10 Hz, 1 H), 5.76 (m 1 H), 7.30–7.38 (m, 10 H).

Step B. (S)-2-((((S)-3-(5-chloro-2-methoxyphenyl)-3-fluoro-2-oxo-6-(trifluoromethyl)indolin-1-yl)methoxy)carbonyl)pentanedioic acid dibenzyl ester (Va⁸).

Fluorooxindole (S)-IV (0.51 g, 1.43 mmol) and the chloromethylcarbamate of aspartic benzyl ester (0.58 g, 1.43 mmol) were added to a suspension of Cs$_2$CO$_3$ (1.00 g, 2.90 mmol) in acetone (35 ml) according to general procedure (B). After work-up and purification, the title compound was isolated as a clear oil (0.41 g, 39% yield). $^1$H NMR (500 MHz, CDCl$_3$): δ 2.92 (dd, J=17.40, 4.57 Hz, 1 H), 3.12 (dd, J=17.40, 4.57 Hz, 1 H), 3.40 (s, 3 H), 4.71 (m, 1 H), 5.05 (s, 2 H), 5.14 (s, 2 H), 5.79 (d, J=10.90 Hz, 1 H), 5.92 (d, J=10.90 Hz, 1 H), 5.95 (d, J=8.24 Hz, 1 H), 6.69 (d, J=8.55 Hz, 1 H), 7.23–7.35(m, 13 H), 7.50 (s, 1 H), 7.79 (d, J=2.13 Hz, 1 H). LRMS: 729 (M+).

Step C. (S)-2-((((S)-3-(5-chloro-2-methoxyphenyl)-3-fluoro-2-oxo-6-(trifluoromethyl)indolin-1-yl)methoxy)carbonyl)pentanedioic acid (Ia⁸).

The glutamic acid dibenzyl ester derivative (0.43 g, 0.58 mmol) was hydrogenated according to the general procedure (C). After work-up and purification, the title compound was isolated as a white solid (0.20 g, 61% yield). $^1$H NMR (500 MHz, DMSO): δ 1.76 (m, 1 H), 1.97 (m, 1 H), 2.28 (m, 2 H), 3.50 (s, 3 H), 4.02 (m, 1 H), 5.85 (apq, J=11.29 Hz, 1 H), 7.08 (d, J=9.77 Hz, 1 H), 7.46 (s, 2 H), 7.62 (dd, J=2.75, 8.85 Hz, 1 H), 7.72 (d, J=2.14 Hz, 1 H), 7.47 (s, 1 H), 7.90 (d, J=8.24 Hz, 1 H), 12.17 (bs, 1 H), 12.64 (bs, 1 H). LRMS: 561 (M−H), 580 (M+NH$_4$). HRMS Calculated 561.0688 (M−H). found 561.0678.

EXAMPLE 9

(S)-2-((((S)-3-(5-chloro-2-methoxyphenyl)-3-fluoro-2-oxo-6-(trifluoromethyl)indolin-1-yl)methoxy)carbonyloxy)propanoic acid (Ib¹)

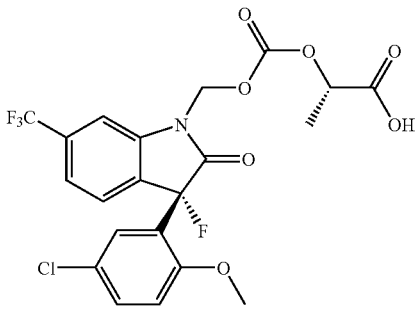

Step A. (S)-2-Chloromethoxycarbonyloxy-propionic acid benzyl ester.

A solution of chloromethyl chloroformate (0.33 mL, 3.73 mmol) in CH$_2$Cl$_2$ (15 mL) and a solution of lactic acid benzyl ester (0.50 g, 3.12 mmol) and Et$_3$N (0.52 mL, 3.73 mmol) in CH$_2$Cl$_2$ (20 mL) were combined according to general procedure (A). After work-up the title compound was isolated as a clear oil (0.13 g, 15% yield). $^1$H NMR (500 MHz, CDCl$_3$): δ 1.57 (d, J=7.02 Hz, 3 H), 5.13 (q, J=7.02 Hz, 1 H), 5.19 (d, J=12.21 Hz, 1 H), 5.24 (d, J=12.21 Hz, 1 H), 5.68 (d, J=6.41 Hz, 1 H), 5.76 (d, J=6.41 Hz, 1 H), 7.32–7.39 (m, 5 H).

Step B. 2-(S)-[3-(S)-(5-Chloro-2-methoxy-phenyl)-3-fluoro-2-oxo-6-trifluoromethyl-2,3-dihydro-indol-1-yl-methoxycarbonyloxy]propionic acid benzyl ester (Vb¹).

Fluorooxindole (S)-IV (0.16 g, 0.44 mmol) and the chloromethylcarbonate of lactic acid benzyl ester (0.12 g, 0.49 mmol) were added to a suspension of Cs$_2$CO$_3$ (0.34 g, 0.98 mmol) in acetone (15 ml) according to general procedure (B). After work-up and purification, the title compound was isolated as a clear oil (0.65 g, 25% yield). $^1$H NMR (500 MHz, CDCl$_3$): δ 1.56 (d, J=7.02 Hz, 3 H), 3.50 (s, 3 H), 5.13 (q, J=7.02 Hz, 1 H), 5.18 (d, J=12.21 Hz, 1 H), 5.22 (d, J=12.21 Hz, 1 H), 5,82 (d, J=10.99 Hz, 1 H), 6.01 (d, J=10.99 Hz, 1 H), 6.72 (d, J=7.62 Hz, 1 H), 7.27 (m, 1 H), 7.32–7.39 (m, 8 H), 7.78 (d, J=3.35 Hz, 1 H). LRMS: 613 (M+NH$_4$), 618 (M+Na). HRMS Calculated 618.0919 (M+Na). found 618.0912.

Step C. (S)-2-((((S)-3-(5-chloro-2-methoxyphenyl)-3-fluoro-2-oxo-6-(trifluoromethyl)indolin-1-yl)methoxy)carbonyloxy)propanoic acid (Ib¹).

The lactic acid benzyl ester derivative (0.23 g, 0.38 mmol) was hydrogenated according to the general procedure (C). After work-up and purification, the title compound was isolated as a white solid (0.15 g, 78% yield). $^1$H NMR (500 MHz, DMSO): δ 1.42 (d, J=7.02 Hz, 3 H), 3.51 (s, 3 H), 4.97 (q, J=7.02 Hz, 1 H), 5.99 (s, 2 H), 7.08 (d, J=8.85 Hz, 1 H), 7.49 (s, 2 H), 7.53 (dd, J=8.85, 2.75 Hz, 1 H), 7.73 (d, J=2.75 Hz, 1 H), 7.78 (s, 1 H), 13.27 (bs, 1 H). LRMS: 527 (M+Na). HRMS Calculated 504.0473 (M−H). found 504.0467.

Preparation of Intermediate (S)-VII (S)-3-(5-chloro-2-methoxyphenyl)-1-(chloromethyl)-3-fluoro-6-(trifluoromethyl)indolin-2-one; (S)-VII Step A. (S)-3-(5-chloro-2-methoxyphenyl)-1-(hydroxymethyl)-3-fluoro-6-(trifluoromethyl)indolin-2-one ((S)-VI).

To a mixture of (S)-3-(5-chloro-2-methoxyphenyl)-3-fluoro-6-(trifluoromethyl)-indolin-2-one ((S)-IV) (60.0 g, 0.167 mol) and K$_2$CO$_3$ (27.7 g, 0.20 mol) in THF (600 mL) was added formaldehyde (37% solution in H$_2$O, 240 mL, 3.2 mol) followed by H$_2$O (300 mL). The lightly turbid mixture was stirred at rt. for 3 h., and diluted with diethyl ether (1000 mL). The organic layer was separated. The aqueous layer was washed with ether (200 mL×2). The combined organic layer was washed with brine, dried over Na$_2$SO$_4$. Evaporation of solvents provided the title compound as a white dry foam (64.5 g, 99% yield). LC/MS m/e: 390 (MH$^+$), 1.60 min. 96% purity. $^1$H NMR (CDCl$_3$): δ 3.50 (s, 3H), 5.28 (m, 1H), 5.45 (m, 1H), 6.75 (dd, J=1.5, 6.5 Hz, 1H), 7.24 (m, 1H), 7.34 (m, (m, 3H), 7.79 (dd, J=1.0, 3.0 Hz, 1H).

Step B. (S)-3-(5-chloro-2-methoxyphenyl)-1-(chloromethyl)-3-fluoro-6-(trifluoromethyl)indolin-2-one; (S)-VII.

To a solution of (S)-3-(5-chloro-2-methoxyphenyl)-1-(hydroxymethyl)-3-fluoro-6-(trifluoromethyl)indolin-2-one ((S)-VI) (64.5 g, 0.166 mol) in CH$_2$Cl$_2$ (700 mL) was added PCl$_3$ (2.0 M in CH$_2$Cl$_2$, 255.0 mL, 0.510 mol) dropwise at 0° C. under N$_2$ over a period of 50 min. The resultant mixture was warmed to rt. and the stirring continued overnight (16 h). The mixture was quenched with ice at 0° C. and the resultant mixture was stirred vigorously for 30 min. The organic layer was separated and the aqueous layer was washed with CH$_2$Cl$_2$. The combined organic layer was washed with brine and dried over Na$_2$SO$_4$. Chromatography (silica gel, EtOAc/Hexanes) provided the title compound as a white dry foam (42.0 g, 62% yield). LC/MS m/e: (no molecular ion), 97% purity. $^1$H NMR (CDCl$_3$): δ 3.55 (s, 3H), 5.39 (d, J=10.5 Hz, 1H), 5.95 (d, J=11.0 Hz, 1H), 6.76 (dd, J=1.5, 9.0 Hz, 1H), 7.28 (m, 2H), 7.35 (dd, J=1.5, 9.0 Hz, 1H), 7.40 (d, J=8.0 Hz, 1H), 7.78 (dd, J=1.0, 2.5 Hz, 1H).

General Procedure (D) for the Acylation of VII

Chloromethyloxindole (S)-VII (1 eq) and the corresponding carboxylic acid (1.1 eq) were added to a suspension of Cs$_2$CO$_3$ (1.5 eq) in acetone. The mixture was stirred for 3 to 24 h at rt. and concentrated. The remaining residue was redissolved in EtOAc, washed with sat. aq. NaHCO$_3$ and brine, dried over MgS$_4$, filtered and concentrated. The remaining yellowish solids were purified by flash chromatography, eluting with EtOAc/Hexanes (2:8)

EXAMPLE 10

(S)-3-((3-(5-chloro-2-methoxyphenyl)-3-fluoro-2-oxo-6-(trifluoromethyl)-indolin-1-yl)methoxy)-3-oxopropanoic acid (Ic¹)

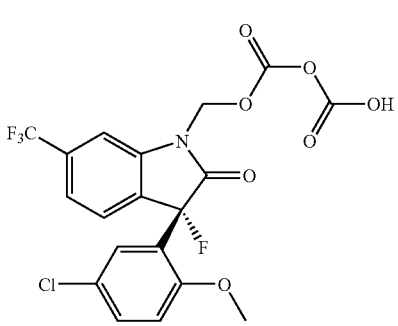

Step A. (S)-3-((3-(5-chloro-2-methoxyphenyl)-3-fluoro-2-oxo-6-(trifluoromethyl)indolin-1-yl)methoxy)-3-oxopropanoic acid benzyl ester (VIII¹).

Chloromethyloxindole (S)-VII (0.20 g, 0.51 mmol) and malonic acid benzyl ester (0.11 g, 0.56 mmol) were added to a suspension of $Cs_2CO_3$ (0.27 g, 0.76 mmol) in $CH_3CN$ (20 ml) according to general procedure (D). After work-up and purification, the title compound was isolated as a clear yellowish oil (0.20 g, 67% yield). ¹H NMR (500 MHz, CDCl₃): δ 3.41 (s, 3 H), 3.51 (s, 2 H), 5.15 (s, 2 H), 5.84 (d, J=10.98 Hz, 1 H), 5.97 (d, J=10.98 Hz, 1 H), 6.72 (dd, J=1.22, 8.85 Hz, 1 H), 7.25 (dd, J=2.75, 7.01 Hz, 1 H), 7.28–7.31 (m, 5 H), 7.83 (dd, J=2.75, 8.85 Hz, 1 H), 7.36 (d, J=7.01 Hz, 1 H), 7.40 (s, 1 H), 7.79 (d, J=2.44 Hz, 1 H). LRMS: 588 (M+Na).

Step B. (S)-3-((3-(5-chloro-2-methoxyphenyl)-3-fluoro-2-oxo-6-(trifluoromethyl)-indolin-1-yl)methoxy)-3-oxopropanoic acid (Ic¹).

The malonic acid benzyl ester derivative (VIII¹; 0.20 g, 0.34 mmol) was hydrogenated according to the general procedure (C). After work-up and purification, the title compound was isolated as a white solid (0.11 g, 65% yield). ¹H NMR (500 MHz, DMSO): δ 3.50 (s, 3 H), 3.52 (s, 2 H), 5.94 (s, 2 H), 7.09 (d, J=8.85 Hz, 1 H), 7.48 (s, 2 H), 7.52 (dd, J=2.44, 8.85 Hz, 1 H), 7.69 (s, 1 H), 7.71 (d, J=2.44 Hz, 1 H), 12.86 (bs, 1 H). LRMS: 474 (M−H). HRMS Calculated 474.0367 (M−H). found 474.0364.

EXAMPLE 11

(S)-4-(((S)-3-(5-chloro-2-methoxyphenyl)-3-fluoro-2-oxo-6-(trifluoromethyl)indolin-1-yl)methoxy)-2-hydroxy-4-oxobutanoic acid (Ic²)

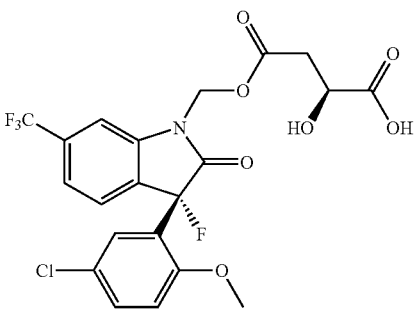

Step A. ((S)-3-(5-chloro-2-methoxyphenyl)-3-fluoro-2-oxo-6-(trifluoromethyl)indolin-1-yl)methyl 2-((S)-2,2-dimethyl-5-oxo-1,3-dioxolan-4-yl)acetate (VIII²).

Chloromethyloxindole (S)-VII (0.25 g, 0.64 mmol) and maleic acid 5-oxo-[1,3]dioxolane (0.14 g, 0.71 mmol) were added to a suspension of $Cs_2CO_3$ (0.34 g, 0.96 mmol) in $CH_3CN$ (20 ml) according to general procedure (D). After work-up and purification, a glassy solid was isolated as the title compound (0.2 g, 55% yield). ¹H NMR (500 MHz, CDCl₃): δ 1.54 (s, 3 H), 1.58 (s, 3 H), 2.86 (dd, J=6.71, 17.09 Hz, 1 H), 3.01 (dd, J=3.97, 17.09 Hz, 1 H), 3.49 (s, 3 H), 4.73 (dd, J=3.97, 6.71 Hz, 1 H), 5.81 (d, J=10.98 Hz, 1 H), 5.97 (d, J=10.98 Hz, 1 H), 6.75 (d, J=8.55 Hz, 1 H), 7.25 (dd, J=2.44, 7.63 Hz, 1 H), 7.32 (dd, J=2.75, 8.55 Hz, 1 H), 7.35 (m, 2 H), 7.76 (dd, J=0.61, 2.44 Hz, 1 H). LRMS: 568 (M+Na).

Step B. (S)-4-(((S)-3-(5-chloro-2-methoxyphenyl)-3-fluoro-2-oxo-6-(trifluoromethyl)indolin-1-yl)methoxy)-2-hydroxy-4-oxobutanoic acid (Ic²).

The maleic acid 5-oxo-[1,3]dioxolane derivative (VIII² 0.32 g, 0.59 mmol) was dissolved in a 4:2:1 mixture of AcOH/THF/H₂O (35 mL) and heated to 60° C. for 5 h. The clear solution was neutralized with saturated aq. NaHCO₃ and extracted with EtOAc (3×). The organic layer was then washed with brine, dried (MgSO₄), filtered and concentrated. The residue was purified by flash chromatography, eluting with $CH_3OH/CH_2Cl_2$ (2:8) to afford the title compound as a white solid. (0.20 g, 67% yield). ¹H NMR (500 MHz, DMSO): δ 2.60 (m, 1 H), 2.80 (bd, J=15.06 Hz, 1 H), 3.50 (s, 3 H), 4.13 (bs, 1 H), 5.88 (s, 2 H), 7.07 (d, J=8.85 Hz, 1 H), 7.47 (s, 2 H), 7.52 (dd, J=2.45, 8.85 Hz, 1 H), 7.35 (m, 2 H), 7.71 (m, 2 H). LRMS: 504 (M−H), 523 (M+NH₄). HRMS Calculated 504.0473 (M−H). found 504.0475.

EXAMPLE 12

(S)-4-((3-(5-chloro-2-methoxyphenyl)-3-fluoro-2-oxo-6-(trifluoromethyl)-indolin-1-yl)methoxy)-4-oxobutanoic acid (Ic³)

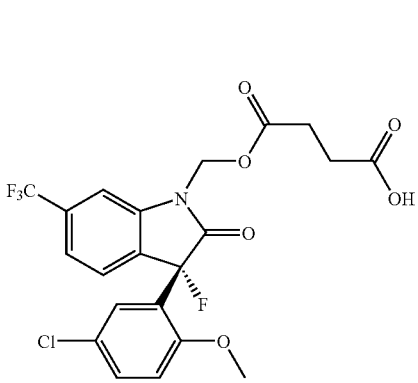

Step A. (S)-4-((3-(5-chloro-2-methoxyphenyl)-3-fluoro-2-oxo-6-(trifluoromethyl)indolin-1-yl)methoxy)-4-oxobutanoic acid benzyl ester (VIII³).

Chloromethyloxindole (S)-VII (0.20 g, 0.50 mmol) and succinic acid benzyl ester (0.11 g, 0.55 mmol) were added to a suspension of $Cs_2CO_3$ (0.26 g, 0.75 mmol) in $CH_3CN$ (20 ml) according to general procedure (D). After work-up and purification, the title compound was isolated as a glassy solid (0.2 g, 66% yield). H NMR (500 MHz, CDCl₃): δ 2.73 (m, 4 H), 3.50 (s, 3 H), 5.12 (s, 2 H), 5.82 (d, J=10.99 Hz, 1 H), 5.90 (d, J=10.99 Hz, 1 H), 6.75 (d, J=8.55 Hz, 1 H), 7.25 (d, J=7.63 Hz, 1 H), 7.30–7.37 (m, 7 H), 7.39 (s, 1 H), 7.78 (d, J=2.44 Hz, 1 H). LRMS: 597 (M+NH₄). HRMS Calculated 602.0969 (M+Na). found 602.0971.

Step B. (S)-4-((3-(5-chloro-2-methoxyphenyl)-3-fluoro-2-oxo-6-(trifluoromethyl)indolin-1-yl)methoxy)-4-oxobutanoic acid (Ic³).

The succinic acid benzyl ester derivative (VIII³; 0.49 g, 1.26 mmol) was hydrogenated according to the general procedure (C). After work-up and purification, the title compound was isolated as a white solid (0.59 g, 82% yield). ¹H NMR (500 MHz, DMSO): δ 2.61 (m, 4 H), 3.51 (s, 3 H), 5.89 (s, 2 H), 7.08 (d, J=8.55 Hz, 1 H), 7.47 (s, 2 H), 7.53 (dd, J=2.74, 8.85 Hz, 1 H), 7.69 (s, 1 H), 7.71 (d, J=2.44 Hz, 1 H), 12.23 (bs, 1 H). LRMS: 507 (M+NH₄), 512 (M+Na). HRMS Calculated 512.0500 (M+Na). found 512.0510.

EXAMPLE 13

2-((S)-4-(((S)-3-(5-chloro-2-methoxyphenyl)-3-fluoro-2-oxo-6-(trifluoromethyl)indolin-1-yl)methoxy)-2-hydroxy-4-oxobutanoyloxy)-acetic acid (Ic⁴)

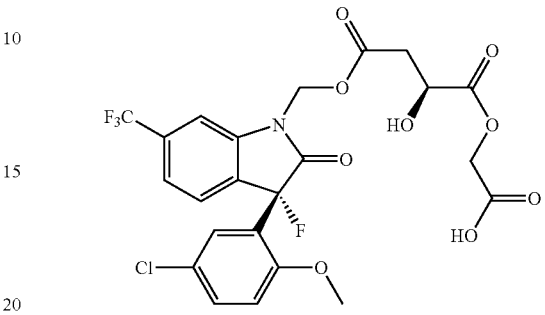

Step A. (S)-2-Hydroxy-succinic acid 1-benzyloxycarbonylmethyl ester.

(S)—O-trifluoroacetyl malic anhydride (4.73 g, 22.3 mmol) and benzyl glycolate (6.32 mL, 44.6 mmol) were stirred at rt. for 24 h. The resulting yellowish oil was taken up in EtOAc and extracted with sat. aqueous $NaHCO_3$. The aqueous layer was then acidified to pH 2 with 1N HCl and extracted with EtOAc (3×). The organic layers were combined, dried over $MgSO_4$, filtered and concentrated. The title compound (3.65 g, 58%) was purified by flash chromatography, eluting with EtOAc/hexanes (4:1). ¹H NMR (500 MHz, CDCl₃): δ 2.85 (dd, J=7.02, 17.09 Hz, 1 H), 2.96 (dd, J=3.97, 17.09 Hz, 1 H), 4.66 (dd, J=3.97, 7.02 Hz, 1 H), 4.72 (d, J=15.87 Hz, 1 H), 4.78 (d, J=15.87 Hz, 1 H), 5.17 (s, 2 H), 7.31–7.39 (m, 6 H).

Step B. 2-((S)-4-(((S)-3-(5-chloro-2-methoxyphenyl)-3-fluoro-2-oxo-6-(trifluoromethyl)indolin-1-yl)methoxy)-2-hydroxy-4-oxobutanoyloxy)acetic acid benzyl ester (VIII⁴).

(S)-VII (0.25 g, 0.64 mmol) and (S)-2-Hydroxy-succinic acid 1-benzyloxycarbonylmethyl ester (0.20 g, 0.71 mmol) were added to a suspension of $Cs_2CO_3$ (0.31 g, 0.96 mmol) in $CH_3CN$ (20 ml) according to general procedure (D). After work-up and purification, the title compound was isolated as a glassy solid (0.2 g, 47% yield). ¹H NMR (500 MHz, CDCl₃): δ 2.91 (dd, J=6.41, 16.79 Hz, 1 H), 2.99 (dd, J=4.58, 16.79 Hz, 1 H), 3.27 (bd, J=5.19 Hz, 1 H), 3.50 (s, 3 H), 4.66 (m, 1 H), 4.72 (d, J=15.87 Hz, 1 H), 4.80 (d, J=15.87 Hz, 1 H), 5.18 (s, 2 H), 5.85 (d, J=10.99 Hz, 1 H), 5.93 (d, J=10.99 Hz, 1 H), 7.25 (d, J=8.24 Hz, 1 H), 7.31–7.39 (m, 8 H), 7.78 (d, J=3.36 Hz, 1 H). LRMS: 676 (M+Na).

Step C. 2-((S)-4-(((S)-3-(5-chloro-2-methoxyphenyl)-3-fluoro-2-oxo-6-(trifluoromethyl)indolin-1-yl)methoxy)-2-hydroxy-4-oxobutanoyloxy)acetic acid (Ic⁴).

2-((S)-4-(((S)-3-(5-chloro-2-methoxyphenyl)-3-fluoro-2-oxo-6-(trifluoromethyl)-indolin-1-yl)methoxy)-2-hydroxy-4-oxobutanoyloxy)acetic acid benzyl ester (0.1 g, 0.15 mmol) was hydrogenated according to the general procedure (C). After work-up and purification, the title compound was isolated as a white solid (40 mg, 47% yield). ¹H NMR (500 MHz, DMSO): δ 2.69 (dd, J=8.24, 16.18 Hz, 1 H), 2.89 (dd, J=4.28, 16.18 Hz, 1 H), 3.50 (s, 3 H), 4.50 (dd, J=4.28, 8.24 Hz, 1 H), 4.55 (s, 2 H), 5.88 (d, J=11.29 Hz, 1 H), 5.93 (d, J=11.29 Hz, 1 H ), 5.97 (bs, 1 H), 7.08 (dd, J=1.22, 8.85 Hz, 1 H), 7.48 (s, 2 H), 7.52 (dd, J=2.44, 8.85 Hz, 1 H), 7.71 (s, 1 H), 7.72 (d, J=1.22 Hz, 1 H), 13.02 (bs, 1 H). LRMS: 564 (M). HRMS Calculated 562.8322 (M–H). found 562.8326.

EXAMPLE 14

(S)-(3-(5-chloro-2-methoxyphenyl)-3-fluoro-2-oxo-6-(trifluoromethyl)indolin-1-yl)methyl 2-(dimethylamino)acetate, hydrochloride) (Ic$^5$)

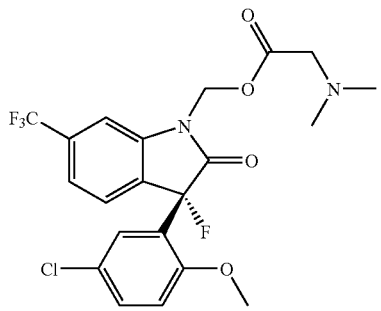

A mixture of (S)-VII, (0.5 g, 1.225 mmol), $Cs_2CO_3$ (0.438 g, 1.35 mmol) and N,N-dimethylglycine (0.138 g, 1.35 mmol) in acetone (20 mL) was stirred at rt. for 3 hr. TLC indicated no starting material remained. The acetone was evaporated and the residue was extracted with ethyl acetate. The filtrate was the washed with sat'd $NaHCO_3$, water, brine and dried with $MgSO_4$. Evaporation of solvent gave 0.32 g of a yellowish oil as crude product (55% yield). Part of the crude product (0.18 g, 0.38 mmol) was then dissolved in acetonitrile and 1.2 eq of 1N HCl (0.46 mL) in anhydrous ether was added. The reaction mixture was stirred at rt. for 3 hr. The title compound was collected as a white precipitate (0.138 g, 70% yield). mp: 157–160° C. MS: 475 (MH$^+$). Anal. Calcd. for $C_{21}H_{19}ClF_4N_2O_4$.HCl.0.67 $H_2O$: C, 48.19; H, 4.11; N, 5.35. Found: C, 48.12; H, 3.79; N, 5.21. $^1H$ NMR (DMSO-d$^6$): δ 3.31 (s, 3H), 3.34 (s, 3H), 3.54 (s, 3H), 4.40–4.55 (m, 2H), 5.61 (m, 2H), 7.12 (d, J=9.0 Hz, 1H), 7.53–7.57 (m, 3H), 7.75 (m, 1H), 8.0 (s, 1H).

EXAMPLE 15

(R)-4-(((S)-3-(5-chloro-2-methoxyphenyl)-3-fluoro-2-oxo-6-(trifluoromethyl)indolin-1-yl)methoxy)-2-hydroxy-N,N,N-trimethyl-4-oxobutan-1-aminium, methyl sulfonate (Ic$^6$)

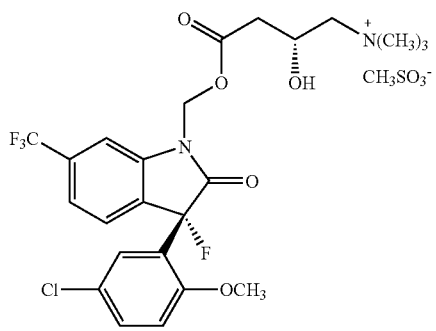

Following the alkylation procedure described for the preparation of Ic$^5$, alkylation of (S)-VII (0.4 g, 0.98 mmol) with $Cs_2CO_3$ (0.352 g, 1.08 mmol) and (L)-Norcamitine (0.159 g, 1.08 mmol) provided the crude product which was then dissolved in ether, and methyl methanesulfonate (0.1 mL) was added. The reaction mixture was stirred at rt. overnight. A white precipitate was collected and purified by trituration with ethyl acetate to afford the title compound (0.13 g, 21% yield 2 steps). mp: 204–207° C. (dec.). MS: 533 (M$^+$). Anal. Calcd. for $C_{24}H_{26}ClF_4N_2O_5.CH_3SO_3.0.5$ $H_2O$: C, 47.06; H, 4.74; N, 4.39. Found: C, 47.17; H, 4.81; N, 4.33. $^1H$ NMR (DMSO-d$^6$): δ 2.29 (s, 3H), 2.57–2.62 (m, 2H), 3.13 (s, 9H), 3.38 (m, 2H), 3.51 (s, 3H), 4.46 (m, 1H), 5.77 (d, J=6.2 Hz, 1H), 5.93 (s, 2H), 7.09 (dd, J=8.9 Hz,1.3 Hz, 1H), 7.50 (m, 2H), 7.53 (dd, J=8.9 Hz, 2.6 Hz, 1H), 7.71–7.74 (m, 2H). IR (KBr, cm$^{-1}$): 3430, 3286, 1763, 1632, 1490, 1456, 1319, 1268, 1207, 1172, 1130.

EXAMPLE 16

(S)-4-((3-(5-chloro-2-methoxyphenyl)-3-fluoro-2-oxo-6-(trifluoromethyl)indoline-1-carbonyloxy)methoxy)-4-oxobutanoic acid (Id)

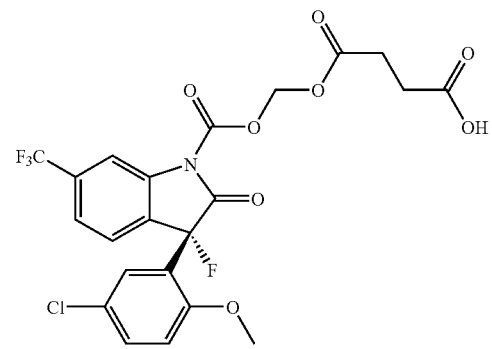

Step A. (S)-(4-(benzyloxy)-4-oxobutanoyloxy)methyl 3-(5-chloro-2-methoxyphenyl)-3-fluoro-2-oxo-6-(trifluoromethyl)indoline-1-carboxylate (X$^1$).

Chloromethylchloroformate (0.16 mL, 1.85 mmol) was added to a solution of (S)-IV (0.55 g, 1.54 mmol) and triethylamine (0.32 mL, 2.31 mmol) in dimethylformamide (30 mL). The solution was stirred at rt. overnight and the solvent was removed under reduced pressure. The remaining residue was taken up in $Et_2O$ and the solid ammonium salts were filtered off. The solvent was removed under reduced pressure and a clear yellow oil was recovered which was then mixed with NaI (0.28 g, 1.84 mmol) in acetone (30 mL) and heated to reflux for 6 h. The solvent was removed under reduced pressure and the residue was taken up in EtOAc. The organic layer was washed with a 1% $Na_2SO_3$ aqueous solution, dried over $MgSO_4$, filtered and concentrated. The residue was dissolved in $CH_3CN$ (30 mL), followed by the addition of $Cs_2CO_3$ (0.52 g, 1.60 mmol) and monobenzyl succinate (0.332 g, 1.54 mmol). The mixture was stirred at rt. for 3 h. and the solvent removed under reduced pressure. After workup and purification as in the general procedure (D), the title compound was obtained as a yellowish oil (0.30 g, 30% yield). $^1H$ NMR (500 MHz, CDCl$_3$): δ 2.73 (m, 4 H), 3.50 (s, 3 H), 5.12 (s, 2 H), 5.84 (d, J=10.99 Hz, 1 H), 5.90 (d, J=10.99 Hz, 1 H), 6.75 (d, J=8.55 Hz, 1 H), 7.25 (d, J=7.63 Hz, 1 H), 7.30–7.37 (m, 7 H), 7.39 (s, 1 H), 7.78 (d, J=2.44 Hz, 1 H). LRMS: 646 (M+Na).

Step B. (S)-4-((3-(5-chloro-2-methoxyphenyl)-3-fluoro-2-oxo-6-(trifluoromethyl)-indoline-1-carbonyloxy)methoxy)-4-oxobutanoic acid (Id).

(S)-4-((3-(5-chloro-2-methoxyphenyl)-3-fluoro-2-oxo-6-(trifluoromethyl)indoline-1-carbonyloxy)methoxy)-4-oxobutanoic acid ($X^1$; 0.20 g, 0.31 mmol) was hydrogenated according to the general procedure (C). After work-up and purification, the title compound was isolated as a white solid (0.13 g, 82% yield). $^1$H NMR (500 MHz, DMSO): δ 2.50 (m, 2 H), 2.60 (m, 2 H), 3.50 (s, 3 H), 5.88 (s, 2 H), 7.07 (d, J=8.85 Hz, 1 H), 7.46 (s, 2 H), 7.51 (dd, J=2.44, 8.85 Hz, 1 H), 7.68 (s, 1 H), 7.70 (d, J=2.44 Hz, 1 H), 12.22 (bs, 1 H). LRMS: 556 (M+Na). HRMS Calculated 556.8038 (M+Na). found 556.8041. mp: 68–71 (decomp).

Preparation of Intermediate of (S)-XI (S)-3-(5-chloro-2-methoxyphenyl)-3-fluoro-2-oxo-6-(trifluoromethyl)-indoline-1-carbonyl chloride ((S)-XI)

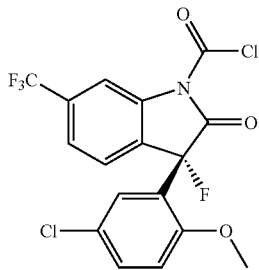

(S)-IV (72 mg, 0.2 mmol) and pyridine (77.5 μL, 0.9 mmol) were dissolved in $CH_2Cl_2$, stirred at rt for 5 min. A 20% solution of phosgene in toluene (0.42 mL, 0.8 mmol) was added dropwise, and the resulting solution was stirred at rt overnight, affording acylchloride (S)-XI.

EXAMPLE 17

2-((S)-2-((S)-3-(5-chloro-2-methoxyphenyl)-3-fluoro-2-oxo-6-(trifluoromethyl)indoline-1-carbonyloxy)propanoyloxy)acetic acid ($Ie^1$)

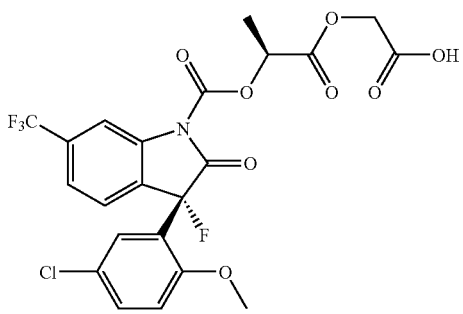

Step A. (S)-2-(tert-Butyl-dimethyl-silanyloxy)-propionic acid benzyloxy-carbonylmethyl ester (S)-2-(t-Butyl-dimethyl-silanyloxy)-propionic acid (0.93 g, 4.6 mmol) and benzyl bromoacetate (0.66 mL, 4.16 mmol) were added to a suspension of $Cs_2CO_3$ (2.20 g, 6.60 mmol) in $CH_3CN$ (100 μL) and stirred at rt. for 24 h. The solvent was removed under reduced pressure and the residue was taken up in EtOAc and $H_2O$ (1:1, 150 mL). The organic layer was separated, washed with brine, dried over $MgSO_4$, filtered and concentrated. The remaining residue was purified by flash chromatography, eluting with EtOAc/hexanes (1:9). The product was obtained as a clear oil (0.71 g, 48%). $^1$H NMR (500 MHz, $CDCl_3$): δ 0.08 (s, 3 H), 0.10 (s, 1 H), 0.91 (s, 9 H), 1.44 (d, J=6.72 Hz, 3 H), 4.44 (t, J=6.72 Hz, 1 H), 4.67 (d, J=15.87 Hz, 1 H), 4.72 (d, J=15.87 Hz, 1 H), 5.19 (s, 2 H), 7.31–7.39 (m, 5 H). $^{13}$C NMR (125 MHz, $CDCl_3$): δ 18.29, 21.35, 25.71, 60.77, 67.14, 68.13, 128.45, 128.57, 128.65, 135.03, 167.40, 173.51. LRMS: 353 (M+H). HRMS Calculated 375.1604 (M+Na). found 375.1611.

Step B. (S)-2-Hydroxy-propionic acid benzyloxycarbonylmethyl ester.

(S)-2-(tert-Butyl-dimethyl-silanyloxy)-propionic acid benzyloxycarbonylmethyl ester (0.25, 0.71 mmol) was dissolved in $CH_3CN$ and treated with aqueous HF (0.5 mL, 48%). The solution was stirred at rt. for 3 h and evaporated under reduced pressure. The residue was redissolved in EtOAc and washed with $H_2O$ and brine, dried over $MgSO_4$, filtered and concentrated. The title compound was obtained as a clear oil (0.15 g, 86%) after purification by flash chromatography, eluting with EtOAc/hexanes (15:85) $^1$H NMR (500 MHz, $CDCl_3$): δ 1.46 (d, J=7.02 Hz, 3 H), 4.41 (t, J=7.02 Hz, 1 H), 4.69 (d, J=15.87 Hz, 1 H), 4.79 (d, J=15.87 Hz, 1 H), 5.20 (s, 2 H), 7.33–7.39 (m, 5 H). $^{13}$C NMR (125 MHz, $CDCl_3$): δ 20.28, 61.19, 66.78, 67.35, 128.47, 128.70, 134.87, 167.23, 175.00. LRMS: 261 (M+Na).

Step C. (S)-((S)-1-(2-(benzyloxy)-2-oxoethoxy)-1-oxopropan-2-yl) 3-(5-chloro-2-methoxyphenyl)-3-fluoro-2-oxo-6-(trifluoromethyl)indoline-1-carboxylate ($XII^1$).

A solution of (S)-2-hydroxy-propionic acid benzyloxycarbonylmethyl ester (50 mg, 0.21 mmol) in $CH_2Cl_2$ was added dropwise to a solution of (S)-XI in toluene and methylene chloride and the resulting solution was stirred at rt for 24 h. The solvent was removed under reduced pressure and the crude material was purified by flash chromatography, eluting with EtOAc/hexanes (30:70), yielding 65 mg (52% yield) of the title compound, as a clear oil. $^1$H NMR (500 MHz, $CDCl_3$): δ 1.74 (d, J=7.02 Hz, 3 H), 3.52 (s, 3 H), 4.70 (d, J=15.87 Hz, 1 H), 4.89 (d, J=15.87 Hz, 1 H), 5.20 (s, 2 H), 5.76 (q, J=7.02 Hz, 1 H), 6.75 (d, J=8.85 Hz, 1 H), 7.29 (m, 1 H), 7.34 (m, 6 H), 7.44 (d, J=7.63 Hz, 1 H), 7.78 (m, 1 H), 8.28 (s, 1 H). LRMS: 524 (M+H).

Step D. 2-((S)-2-((S)-3-(5-chloro-2-methoxyphenyl)-3-fluoro-2-oxo-6-(trifluoromethyl)indoline-1-carbonyloxy)propanoyloxy)acetic acid ($Ie^1$).

(S)-((S)-1-(2-(benzyloxy)-2-oxoethoxy)-1-oxopropan-2-yl) 3-(5-chloro-2-methoxyphenyl)-3-fluoro-2-oxo-6-(trifluoromethyl)indoline-1-carboxylate ($XII^1$) (50 mg, 0.08 mmol) was hydrogenated according to the general procedure (C). After work-up and purification, the title compound was isolated as a white solid (040 mg, 94% yield). $^1$H NMR (500 MHz, $CDCl_3$): δ 1.65 (d, J=7.02 Hz, 3 H), 3.55 (s, 3 H), 4.66 (d, J=15.56 Hz, 1 H), 4.74 (d, J=15.56 Hz, 1 H), 5.52 (q, J=7.01 Hz, 1 H), 7.11 (d, J=8.85 Hz, 1 H), 7.56 (dd, J=2.44, 8.85 Hz), 7.65 (m, 2 H), 7.77 (m, 1 H), 8.18 (s, 1 H), 13.25 (bs, 1 H). LRMS: 532 (M−H), 533 (M), 551 (M+$NH_4$). HRMS Calculated 532.0422 (M−H). found 532.0403.

EXAMPLE 18

(S)-2-(3-(5-chloro-2-methoxyphenyl)-3-fluoro-2-oxo-6-(trifluoromethyl)indoline-1-carbonyloxy)acetic acid (Ie²)

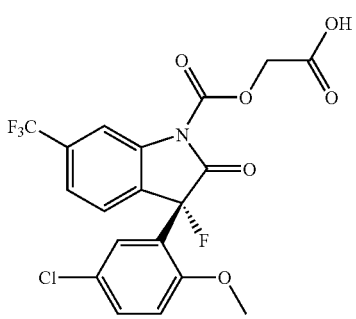

Step A. (S)-2-(3-(5-chloro-2-methoxyphenyl)-3-fluoro-2-oxo-6-(trifluoromethyl)indoline-1-carbonyloxy)acetic acid, benzyloxycarbonylmethyl ester (XII²).

To a solution of (S)-XI in toluene and methylene chloride was added 0.6 mL of pyridine followed by the addition of benzyl glycolate (0.878 mL). The resulting mixture was stirred at room temperature for an hour. This reaction mixture was diluted with dichloromethane and washed with water. The organic layer was dried over $Na_2SO_4$ and condensed by rotary evaporation. The residue was chromatographed on a silica gel flash column packed with ethyl acetate: hexane (v/v, 10:1) and washed with dichloromethane to afford 1.32 g of the title compound.

Step B. (S)-2-(3-(5-chloro-2-methoxyphenyl)-3-fluoro-2-oxo-6-(trifluoromethyl)indoline-1-carbonyloxy)acetic acid (Ie²).

A solution of (S)-2-(3-(5-chloro-2-methoxyphenyl)-3-fluoro-2-oxo-6-(trifluoromethyl)indoline-1-carbonyloxy) acetic acid, benzyloxycarbonylmethyl ester (XII²) (95 mg, 0.17 mmol) in methanol (50 mL) was hydrogenated with Pd—C(10%) as catalyst at room temperature. Prep. HPLC purification afforded the title compound (42.4 mg) with 98% HPLC purity (yield 53.3%). $^1$H NMR (CDCl$_3$, 500 MHz) δ 8.34 (s, 1H), 7.79 (d, 1H), 7.47 (d, 1H), 7.36 (dd, 1H), 7.31 (dd, 1H), 6.76 (dd, 1H), 5.08 (d, 1H), 4.96 (d, 1H), 3.57 (s, 3H); LC-MS, 462.88 (MH⁺, 99%); MS (m/e) 462 (M+1).

EXAMPLE 19

(S)-4-(3-(5-chloro-2-methoxyphenyl)-3-fluoro-2-oxo-6-(trifluoromethyl)indoline-1-carbonyloxy)butanoic acid (Ie³)

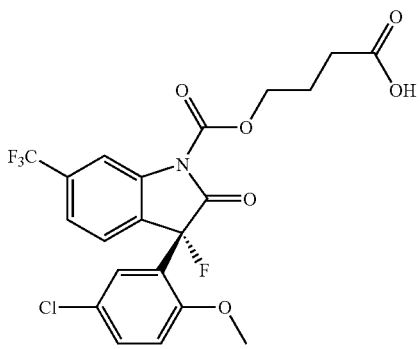

Step A. 4-Hydroxy-butyric acid benzyl ester.

Sodium bead (440 mg) was added with stirring to benzyl alcohol (50 mL) at room temperature. When the sodium was completely dissolved, γ-butyrolactone was dropped in and the resultant mixture was stirred at room temperature for overnight. Amberlite IR-120(H⁺) cation-exchange resin was added into the reaction mixture to neutralize the reaction mixture to pH~7. Filtration, followed by distillation of the filtrate in vacuo to remove excess amount of benzyl alcohol at ca. 85° C. afforded a residue which was chromatographed with ethyl acetate: hexane (20%–33%) to afford 451 mg of the title compound.

Step B. (S)-3-(5-Chloro-2-methoxy-phenyl)-3-fluoro-2-oxo-6-trifluoromethyl-2,3-dihydro-indole-1-carboxylic acid 3-benzyloxycarbonyl-propyl ester (XII³).

To a stirred solution of 1 mmol of (S)-XI in dichloromethane and toluene was added 4-hydroxy-butyric acid benzyl ester (432 mg) in dichloromethane (5 mL) and the resulting mixture was stirred rapidly at 45° C. overnight. After removal of the excess solvent by rotary evaporation, the residue was chromatographed on a flash silica gel column packed and washed with ethyl acetate: hexane (5:1, v/v) to afford the title compound (306 m). $^1$H NMR (CDCl$_3$, 500 MHz) δ 8.31 (s, 1H), 7.78 (dd, 1H), 7.44 (d, 1H), 7.34 (m, 6H), 7.28 (dd, 1H), 6.74 (dd, 1H), 5.11 (s, 2H), 4.52 (t, 2H), 3.49 (s, 3H), 2.62 (t, 2H), 2.17 (m, 2H); LC-MS, 582.13 (MH⁺); Anal. Calcd. for $C_{28}H_{22}ClF_4NO_6$: C=57.99%, H=3.82%, N=2.41. found: C=58.15%, H=3.80%, N=2.32%.

Step C. (S)-4-(3-(5-chloro-2-methoxyphenyl)-3-fluoro-2-oxo-6-(trifluoromethyl)indoline-1-carbonyloxy)butanoic acid (Ie³).

Hydrogenation of (S)-3-(5-Chloro-2-methoxy-phenyl)-3-fluoro-2-oxo-6-trifluoromethyl-2,3-dihydro-indole-1-carboxylic acid 3-benzyloxycarbonyl-propyl ester (XII³) (100 mg, 0.172 mmol) in methanol (80 mL) with Pd—C (10%) as catalyst at room temperature under one atmosphere pressure provided the title compound 27 mg (yield 32%) after prep. HPLC purification. $^1$H NMR (CDCl$_3$, 500 MHz) δ 8.31 (s, 1H), 7.78 (dd, 1H), 7.44 (d, 1H), 7.35 (dd, 1H), 7.28 (dd, 1H), 6.76 (dd, 1H), 4.53 (m, 2H), 3.52 (s, 3H), 2.60 (m, 2H), 2.15 (m, 2H); LC-MS, 512.06 (MHNa+); Anal. Calcd. for $C_{21}H_{16}ClF_4NO_6$: C=51.49%, H=3.29%, N=2.86. found: C=51.75%, H=3.48%, N=2.67%.

EXAMPLE 20

(S)-(3-(5-chloro-2-methoxyphenyl)-3-fluoro-2-oxo-6-(trifluoromethyl)indolin-1-yl)methyl 2-(1H-tetrazol-5-yl)acetate (If$^1$)

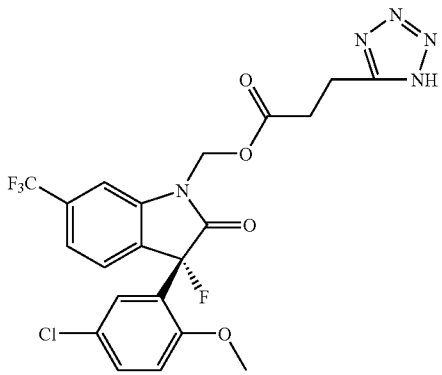

Step A. Ethyl 2-(1-((2-(trimethylsilyl)ethoxy)methyl)-1H-tetrazol-5-yl)acetate.

A 60% suspension of NaH in mineral oil (0.24 g, 5.84 mmol) was stirred with 5 mL of dry hexanes, decanted, the solvent was removed by syringe and the remaining residue was dried under vacuum. The solid was suspended in dry DMF (30 mL) and a solution of (1H-tetrazol-5-yl)-acetic acid ethyl ester (0.84 g, 5.4 mmol) in DMF (10 mL) was added at 0° C. The mixture was stirred for 30 min at 0° C. followed by slow addition of (2-chloromethoxy-ethyl)-trimethylsilane (SEM-Cl) (1 mL, 5.65 mmol). The resulting mixture was stirred at rt overnight, diluted with Et$_2$O, washed with H$_2$O and brine, dried (MgSO$_4$), filtered and concentrated under reduced pressure. Purification was done by flash chromatography, eluting with EtOAc/hexanes (20:80). Two regioisomers were isolated and their structures were assigned by comparison to similar known compounds and predictive software. The title compound eluted more slowly than the 2-substitued tetrazole (ethyl 2-(2-((2-(trimethylsilyl)ethoxy)methyl)-2H-tetrazol-5-yl)acetate) affording 0.72 g (47%) of the title compound. $^1$H NMR (500 MHz, CDCl$_3$): δ –0.05 (s, 9 H), 0.86 (dd, J=8.24, 8.56 Hz, 2 H), 1.25 (t, J=7.17 Hz, 3 H), 3.53 (dd, J=8.24, 8.56 Hz, 2 H), 4.08 (s, 2 H), 4.18 (q, J=7.17 Hz, 2 H), 5.75 (s, 2 H). $^{13}$C NMR (125 MHz, DMSO): δ –1.53, 14.02, 17.63, 29.69, 62.23, 68.02, 76.49, 149.55, 166.57. LRMS: 287 (M–H).

Step B. 2-(1-((2-(trimethylsilyl)ethoxy)methyl)-1H-tetrazol-5-yl)acetic acid.

A solution of ethyl 2-(1-((2-(trimethylsilyl)ethoxy)methyl)-1H-tetrazol-5-yl)acetate (0.71 g, 2.90 mmol) in THF (15 mL) and cooled to 0° C. A solution of LiOH (0.35 g, 14.5 mmol) in H$_2$O (15 mL) was then slowly added to the THF solution and the mixture was stirred at rt. for 3 h. THF was removed under reduced pressure and the aqueous layer was washed with EtOAc (2x). The combined organic layers were washed with NaHCO$_3$ and the extract was added to the original aqueous layers. The pH was the adjusted to 4 with a 1N KHSO$_4$ solution and back-extracted with EtOAc (3x). The organic layers were combined, dried over MgSO$_4$, filtered and concentrated to yield the title compound (0.60 g, 95% yield) which was used without further purification. $^1$H NMR (500 MHz, CDCl$_3$): δ –0.05 (s, 9 H), 0.85 (dd, J=8.18, 8.24 Hz, 2 H), 3.51 (dd, J=8.18, 8.24 Hz, 2 H), 4.16 (s, 2 H), 5.80 (s, 2 H), 13.06 (bs, 1 H). LRMS: 257 (M–H).

Step C. (S)-(3-(5-chloro-2-methoxyphenyl)-3-fluoro-2-oxo-6-(trifluoromethyl)indolin-1-yl)methyl 2-(1-((2-(trimethylsilyl)ethoxy)methyl)-1H-tetrazol-5-yl)acetate (XIII$^1$).

(S)-VII (0.26 g, 0.67 mmol) and 2-(1-((2-(trimethylsilyl)ethoxy)methyl)-1H-tetrazol-5-yl)acetic acid (0.19 g, 0.73 mmol) were added to a suspension of Cs$_2$CO$_3$ (0.26 g, 0.75 mmol) in CH$_3$CN (10 ml) according to general procedure (D). After work-up and purification, the title compound was isolated as a clear oil (0.28 g, 70% yield). $^1$H NMR (500 MHz, CDCl$_3$): δ –0.03 (s, 9 H), 0.87 (dd, J=7.63, 9.46 Hz, 2 H), 3.46 (s, 3 H), 3.55 (dd, J=7.63, 9.46 Hz, 2 H), 4.21 (s, 2 H), 5.79 (s, 2 H), 5.87 (d, J=10.96 Hz, 1 H), 5.90 (d, J=10.99 Hz, 1 H), 6.76 (d, J=8.55 Hz, 1 H), 7.27 (d, J=7.63 Hz, 1 H), 7.32 (s, 1 H), 7.35 (dd, J=2.44, 8,85 Hz, 1 H), 7.38 (d, J=7.93 Hz, 1 H) 7.79 (d, J=2.14 Hz). LRMS: 630 (M). HRMS Calculated 628.1406 (M+Na). found 628.1424.

Step D. (S)-(3-(5-chloro-2-methoxyphenyl)-3-fluoro-2-oxo-6-(trifluoromethyl)indolin-1-yl)methyl 2-(1H-tetrazol-5-yl)acetate (S)-(3-(5-chloro-2-methoxyphenyl)-3-fluoro-2-oxo-6-(trifluoromethyl)indolin-1-yl)methyl 2-(1-((2-(trimethylsilyl)ethoxy)methyl)-1H-tetrazol-5-yl)acetate (XIII$^1$; n=1) (0.24 g, 0.38 mmol) was dissolved in CH$_3$CN (20 mL), treated with aqueous HF (1 mL, 48% in H$_2$O), and stirred at rt. until the starting material was completely consumed (as judged by HPLC). The mixture was neutralized with aqueous NaHCO$_3$, and the CH3CN removed under reduced pressure. The aqueous layer was extracted with EtOAc, and the organic layer was then dried over MgSO$_4$, filtered and concentrated. The isolated white solid was lyophilized to afford the title compund (0.14 g, 71% yield). $^1$H NMR (500 MHz, DMSO): δ 3.45 (s, 3 H), 5.79 (s, 2 H), 5.87 (d, J=10.96 Hz, 1 H), 5.91 (s, 2 H), 7.07 (d, J=8.85 Hz, 1 H), 7.47 (s, 2 H), 7.52 (dd, J=2.44, 8.85 Hz, 1 H), 7.72 (s, 2 H). LRMS: 500 (M). HRMS Calculated 498.8000 (M–H) found 498.8003.

EXAMPLE 21

(S)-(3-(5-chloro-2-methoxyphenyl)-3-fluoro-2-oxo-6-(trifluoromethyl)indolin-1-yl)methyl 3-(1H-tetrazol-5-yl)propanoate (If$^2$)

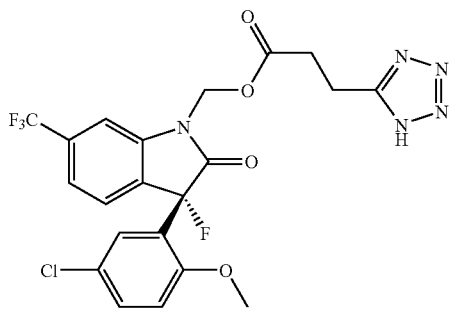

Step A. Methyl 3-(1H-tetrazol-5-yl)propanoate.

Bu$_3$SnO (0.71 g, 2.86 mmol) was added to a solution of 3-cyano-propionic acid methyl ester (3 mL, 28.6 mmol) and trimethylsilylazide (7.6 mL, 57.2 mmol) in toluene and the mixture was heated to 110° C. for 24 h. The brownish solution was concentrated under reduced pressure, the remaining residue redissolved in MeOH and concentrated again. The oily residue was pationed between EtOAc and aq. NaHCO₃, the organic phase was separated and washed with more aq. NaHCO₃. The aqueous extracts were the acidified to pH=2 with aq. 1 N HCl and re-extracted with EtOAc. The combined organic layer was dried (MgSO₄), filtered and concentrated. The remaining brown solid was purified by flash chromatography, eluting with EtOAc, giving 4.2 g (94%) of the title compound as a white solid. ¹H NMR (500 MHz, CDCl₃): δ 2.89 (m, 2 H), 3.33 (m, 2 H), 3.75(s, 3 H), 13.90 (bs, 1 H).

Step B. Methyl 3-(1-((2-(trimethylsilyl)ethoxy)methyl)-1H-tetrazol-5-yl)propanoate.

A 60% suspension of NaH in mineral oil (0.28 g, 7.05 mmol) was stirred with 5 mL of dry hexanes, decanted, the solvent was removed by syringe and the remaining residue was dried under vacuum. The solid was suspended in dry DMF (30 mL) and a solution of methyl 3-(1H-tetrazol-5-yl)propanoate (1.0 g, 6.4 mmol) in DMF (10 mL) was added at 0° C. The mixture was stirred for 30 min at 0° C. followed by slow addition of (2-chloromethoxy-ethyl)-trimethylsilane (SEM-Cl) (1.2 mL, 6.72 mmol). The resulting mixture was stirred at rt overnight, diluted with Et₂O, washed with H₂O and brine, dried (MgSO₄), filtered and concentrated under reduced pressure. Purification was done by flash chromatography, eluting with EtOAc/hexanes (20:80). Two regioisomers were isolated and their structures were assigned by comparison by similarity to known compounds and predictive software. The title compound eluted more slowly than the corresponding 2-substituted tetrazole ((3-[2-(2-Trimethylsilanyl-ethoxymethyl)-2H-tetrazol-5-yl]-propionic acid methyl ester). The title compound was obtained in 41% yield (0.64 g). ¹H NMR (500 MHz, CDCl₃): δ −0.04 (s, 9 H), 0.88 (dd, J=8.24, 8.55 Hz, 2 H), 2.95 (t, J=7.02 Hz, 2 H), 3.18 (t, J=7.02 Hz, 2 H), 3.57 (dd, J=8.24, 8.55 Hz, 2 H), 3.66 (s, 3 H), 5.72 (s, 2 H). ¹³C NMR (125 MHz, DMSO): δ −1.52, 17.65, 18.49, 30.83, 52.04, 67.81, 75.53, 154.65, 172.11. LRMS: 287 (M−H).

Step C. 3-(1-((2-(trimethylsilyl)ethoxy)methyl)-1H-tetrazol-5-yl)propanoic acid.

Methyl 3-(1-((2-(trimethylsilyl)ethoxy)methyl)-1H-tetrazol-5-yl)propanoate (0.72 g, 2.52 mmol) was dissolved in THF (15 mL) and cooled to 0° C. A solution of LiOH (91 mg, 3.78 mmol) in H₂O (15 mL) was then slowly added to the THF solution and the mixture was stirred at rt. for 3 h. THF was removed under reduced pressure and the aqueous layer was washed with EtOAc (2×). The combined organic layers were washed with NaHCO₃ and the extract was added to the original aqueous layers. The pH was the adjusted to 4 with a 1N KHSO₄ solution and back-extracted with EtOAc (3×). The organic layers were combined, dried over MgSO₄, filtered and concentrated to yield the title compound (0.60 g, 87% yield) which was used without further purification. ¹H NMR (500 MHz, DMSO): δ −0.05 (s, 9 H), 0.86 (dd, J=8.18, 8.24 Hz, 2 H), 2.79 (t, J=7.14 Hz, 2 H), 3.12 (t, J=7.14 Hz, 2 H), 3.56 (dd, J=8.18, 8.24 Hz, 2 H), 5.79 (s, 2 H), 12.35 (bs, 1 H). ¹³C NMR (125 MHz, CDCl₃): δ −1.55, 16.99, 17.95, 30.31, 66.42, 74.90, 155.12, 172.73. LRMS: 273 (M+H).

Step D. (S)-(3-(5-chloro-2-methoxyphenyl)-3-fluoro-2-oxo-6-(trifluoromethyl)indolin-1-yl)methyl 3-(1-((2-(trimethylsilyl)ethoxy)methyl)-1H-tetrazol-5-yl)propanoate (XIII²).

(S)-VII (0.28 g, 0.73 mmol) and 3-(1-((2-(trimethylsilyl)ethoxy)-methyl)-1H-tetrazol-5-yl)propanoic acid (0.21 g, 0.77 mmol) were added to a suspension of Cs₂CO₃ (0.27 g, 0.845 mmol) in CH₃CN (15 ml) according to general procedure (D). After work-up and purification, the title compound was obtained as a clear oil (0.35 g, 75% yield). ¹H NMR (500 MHz, CDCl₃): δ −0.07 (s, 9 H), 0.87 (dd, J=7.63, 8.54 Hz, 2 H), 3.01 (t, J=7.63, Hz, 2 H), 3.20 (t, J=7.63, Hz, 2 H), 3.44 (s, 3 H), 3.56 (dd, J=7.63, 9.46 Hz, 2 H), 4.21 (s, 2 H), 5.69 (s, 2 H), 5.79 (d, J=11.30 Hz, 1 H), 5.85 (d, J=11.30 Hz, 1 H), 6.72 (d, J=8.55 Hz, 1 H), 7.20 (dd, J=2.44, 8.55 Hz, 2 H), 7.31 (s, 1 H), 7.70 (s, 1 H). LRMS: 644 (M+Na).

Step E. (S)-(3-(5-chloro-2-methoxyphenyl)-3-fluoro-2-oxo-6-(trifluoromethyl)indolin-1-yl)methyl 3-(1H-tetrazol-5-yl)propanoate (If²).

(S)-(3-(5-chloro-2-methoxyphenyl)-3-fluoro-2-oxo-6-(trifluoromethyl)indolin-1-yl)methyl 3-(1-((2-(trimethylsilyl)ethoxy)methyl)-1H-tetrazol-5-yl)propanoate (XIII²) (0.30 g, 0.47 mmol) was dissolved in CH₃CN (30 mL) and treated with aqueous HF (3 mL, 48% in H₂O), and stirred at rt. until the starting material was completely consumed (as judged by HPLC). The mixture was neutralized with aqueous NaHCO₃, and the CH3CN removed under reduced pressure. The aqueous layer was extracted with EtOAc, and the organic layer was then dried over MgSO₄, filtered and concentrated. The isolated white solid was lyophilized to afford the title compound (0.21 g, 83% yield). ¹H NMR (500 MHz, DMSO): δ 2.93 (t, J=7.32, Hz, 2 H), 3.14 (t, J=7.32 Hz, 2 H), 3.50 (s, 3 H), 5.89 (d, J=10.99 Hz, 1 H), 5.91 (d, J=10.99 Hz, 1 H), 7.02 (d, J=8.55 Hz, 1 H), 7.48 (s, 2 H), 7.52 (dd, J=2.44, 8.55 Hz, 2 H), 7.70 (s, 1 H), 7.72 d, J=2.44 Hz, 1 H). LRMS: 514 (M+H). HRMS Calculated 512.8270 (M−H). found 512.8266.

EXAMPLE 22

Sodium (S)-2-(4-((3-(5-chloro-2-methoxyphenyl)-3-fluoro-2-oxo-6-(trifluoromethyl)indolin-1-yl)methoxy)-4-oxobutanamido)ethanesulfonate (Ig)

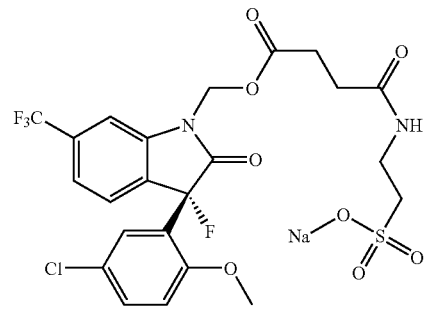

(S)-Ic³ (0.1 g, 0.2 mmol) and Et₃N (0.078 mL, 0.57 mmol) were dissolved in THF (10 mL) and the resulting solution was cooled to 0° C. i-Butylchloroformate was added slowly and the mixture was warmed up to rt. over 15 min. A solution of tetrabutylammonium taurine (0.146 g, 0.4 mmol) in THF (2 mL) was added to the mixture and stirred for 24 h at rt. The suspension was filtered, concentrated under reduced pressure and the remaining oil was purified by flash chromatography, eluting with MeOH/CH₂Cl₂ (1:33). The isolated oil was then dissolved in H₂O and passed through a DOWEX ion-exchange resin (Na⁺ form) column. The solvent was removed under vacuum and the title compound was obtained as a solid following recrystallization from CH$_2$Cl$_2$/hexanes (50 mg, 40% yield). 1H NMR (500 MHz, DMSO): δ 2.36 (t, J=6.72, Hz, 2 H), 2.53 (m, 2 H), 2.58 (t, J=6.72Hz, 2 H), 3.29 (m, 2 H), 3.51 (s, 3 H), 5.88 (s, 2 H), 7.06 (d, J=8.84 Hz, 1 H), 7.47 (s, 2 H), 7.52 (dd, J=2.44, 8.55 Hz, 2 H), 7.71 (s, 2 H), 7.79 (t, J=5.16 Hz, 1 H). LRMS: 595 (M−H), 614 (M+Na). HRMS Calculated 618.9181 (M−H). found 618.9178.

Preparation of Intermediate (S)-XIV (S)-(3-(5-chloro-2-methoxyphenyl)-3-fluoro-2-oxo-6-(trifluoromethyl)indolin-1-yl)methyl 4-(chloromethyl)benzoate ((S)-XIV)

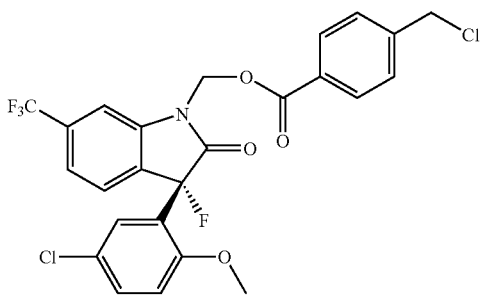

To a solution of 4-(chloromethyl)benzoyl chloride (1.867 g, 9.88 mmol) in methylene chloride (40 mL), pyridine (0.8 mL, 9.88 mmol) was added dropwise under nitrogen at 0° C. A solution of (S)-IV (3.5 g, 8.98 mmol) in methylene chloride (30 mL) was added at 0° C. The reaction mixture was warmed to rt. and stirred for 2 days. The reaction was quenched with water and the organic layer was separated. It was then washed with 1N HCl solution, sat'd NaHCO$_3$, water and brine, and dried with MgSO$_4$. The solvent was evaporated and ether was added. The filtrate was collected and evaporated to give the title compound as a white foam solid.(3.52 g, ≈80% pure by NMR) It was used in the next step without any further purification.

Preparation of Intermediate ((S)-XV (S)-(3-(5-chloro-2-methoxyphenyl)-3-fluoro-2-oxo-6-(trifluoromethyl)indolin-1-yl)methyl 3-(chloromethyl)benzoate ((S)-XV)

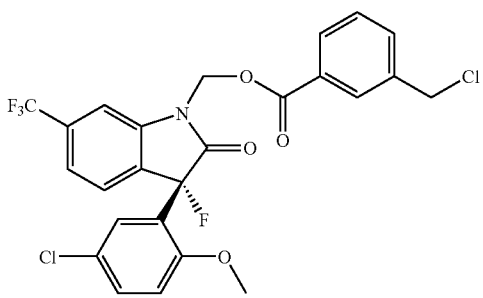

To a solution of 3-(chloromethyl)benzoyl chloride (1.867 g, 9.88 mmol) in methylene chloride (40 mL), pyridine (0.8 mL, 9.88 mmol) was added dropwise under nitrogen at 0° C. A solution of (S)-IV (3.5 g, 8.98 mmol) in methylene chloride (30 mL) was added at 0° C. The reaction mixture was warmed to rt. and stirred for 2 days. The reaction was quenched with water and the organic layer was separated. It was then washed with 1N HCl solution, sat'd NaHCO$_3$, water and brine, and dried with MgSO$_4$. The solvent was evaporated and ether was added. The filtrate was collected and evaporated to give a white foamy solid.(2.47 g, ≈70% pure by NMR) It was used in the next step without any further purification.

General Procedure (E) to Prepare (Aminomethyl)Benzoate Derivative of (S)-IV.

To a suspension of XIV or XV, K$_2$CO$_3$ and NaI in acetone, 1.1 eq. of amine was added at rt. The reaction mixture was stirred at rt. for 2 days. TLC indicated no starting material remained. Acetone was evaporated and the residue was extracted with ether. The filtrate was then washed with sat'd NaHCO$_3$, water, brine and dried with MgSO$_4$. Evaporation of solvent gave a light yellow solid. It was then dissolved in ether and 1.1 eq of 1N HCl in anhydrous ether was added. The reaction mixture was stirred at rt. for overnight. The precipitate was collected and purified by trituration with solvent or prep. HPLC to afford final product.

EXAMPLE 23

(S)-(3-(5-chloro-2-methoxyphenyl)-3-fluoro-2-oxo-6-(trifluoromethyl)indolin-1-yl)methyl 4-(morpholinomethyl)benzoate, hydrochloride (Ih$^1$)

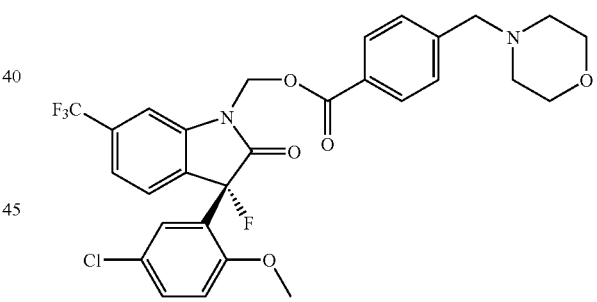

Following general procedure (E), to a suspension of (S)-XIV (0.35 g, 0.65 mmol), K$_2$CO$_3$ (0.098 g, 0.71 mmol) and NaI (25 mg) in acetone (15 mL), 1.1 eq. of morpholine (0.062 mL) was added. After HCl salt formation, the title compound was collected as a light yellow solid (90 mg, 22% yield). mp: 174–178° C. MS m/e: 593 (MH$^+$). Anal. Calcd. for C$_{29}$H$_{25}$ClF$_4$N$_2$O$_5$.HCl.0.5 H$_2$O: C, 54.56; H, 4.26; N, 4.39. Found: C, 54.43; H, 4.52; N, 4.22. $^1$H NMR (DMSO-d$^6$): δ 3.11–3.19 (m, br, 4H), 3.38 (s, 3H), 3.70–3.77 (m, br, 2H), 3.87–3.94 (m, br, 2H), 4.41(s, br, 2H), 6.14 (d, J=11.1 Hz, 1H), 6.21 (d, J=11.2 Hz, 1H), 7.05 (d, J=8.9 Hz, 1H), 7.50–7.55 (m, 3H), 7.72 (d, J=2.2 Hz, 1H), 7.77 (d, J=8.3 Hz, 2H), 7.9 (s, 1H), 8.06 (d, J=8.2 Hz, 2H), 11.05 (s, br, 1H).

EXAMPLE 24

(S)-(3-(5-chloro-2-methoxyphenyl)-3-fluoro-2-oxo-6-(trifluoromethyl)indolin-1-yl)methyl 3-(morpholinomethyl)benzoate, hydrochloride (Ih2)

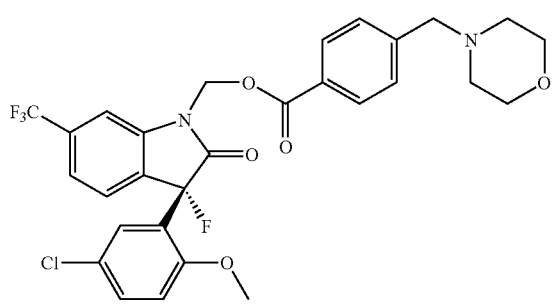

Following general procedure (E), to a suspension of (S)-XV (0.5 g, 0.92 mmol), $K_2CO_3$ (0.14 g. 1.01 mmol) and NaI (40 mg) in acetone (20 mL), 1.1 eq. of morpholine (0.112 mL) was added. After HCl salt formation, a light yellow solid was collected and purified by trituration with acetonitrile/ether to afford the title compound as a white solid (0.157, 27% yield). mp: 210–214° C. (dec.). MS m/e: 593 (MH$^+$). Anal. Calcd. for $C_{29}H_{25}ClF_4N_2O_5$·HCl: C, 55.34; H, 4.16; N, 4.45. Found: C, 55.02; H, 4.26; N, 4.36. $^1$H NMR (DMSO-d$^6$): δ 3.05–3.21 (m, br, 4H), 3.36 (s, 3H), 3.69 (t, br, J=1 1.5 Hz, 2H), 3.91 (d, br, J=11.7 Hz, 2H), 4.42 (d, br, J=4.6 Hz, 2H), 6.14 (d, J=11.4 Hz, 1H), 6.18 (d, J=11.4 Hz, 1H), 7.03 (dd, J=8.9 Hz, 1.1 Hz, 1H), 7.48–7.53 (m, 3H), 7.64 (t, J=7.8 Hz, 1H), 7.71 (d, J=1.8 Hz, 1H), 7.9–7.94 (m, 2H), 8.04 (d, J=7.9 Hz, 1H), 8.18 (s, 1H), 10.84 (s, br, 1H). IR (KBr, cm$^{-1}$): 3431, 2364, 1778, 1765, 1723, 1632, 1492, 1458, 1320, 1270, 1127.

EXAMPLE 25

(S)-(3-(5-chloro-2-methoxyphenyl)-3-fluoro-2-oxo-6-(trifluoromethyl)indolin-1-yl)methyl 4-(piperidin-1-ylmethyl)benzoate, hydrochloride (Ih3)

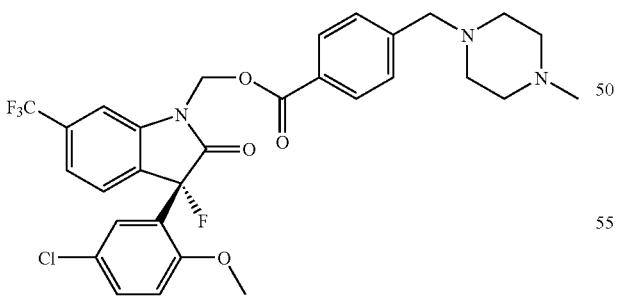

Following general procedure (E), to a suspension of (S)-XIV (0.5 g, 0.92 mmol), $K_2CO_3$ (0.14 g, 1.01 mmol) and NaI (40 mg) in acetone (20 mL), 1.1 eq. of 1-methylpiperazine (0.112 mL) was added. After HCl salt formation, a light yellow solid was collected and purified by trituration with acetonitrile/ether to afford the title compound as an off-white solid (0.17 g, 27% yield). mp: 265–269° C. (dec.). MS m/e: 606 (MH$^+$). Anal. Calcd. for $C_{30}H_{28}ClF_4N_3O_4$·2HCl·0.5 $H_2O$: C, 52.38; H, 4.54; N, 6.11. Found: C, 52.23; H, 4.79; N, 5.95. $^1$H NMR (DMSO-d$^6$): δ 2.76 (s, br, 3H), 3.12 (s, br, 4H), 3.35 (s, 3H), 3.86 (s, br, 6H), 6.11 (d, J=11.4 Hz, 1H), 6.18 (d, J=11.4 Hz, 1H), 7.03 (d, J=8.9 Hz, 1H), 7.48–7.53 (m, 3H), 7.61 (m, 2H), 7.70 (d, J=2.4 Hz, 1H), 7.89 (s, 1H), 7.98 (m, 2H).

EXAMPLE 26

(S)-(3-(5-chloro-2-methoxyphenyl)-3-fluoro-2-oxo-6-(trifluoromethyl)indolin-1-yl)methyl 3-(piperidin-1-ylmethyl)benzoate, hydrochloride (Ih$^4$)

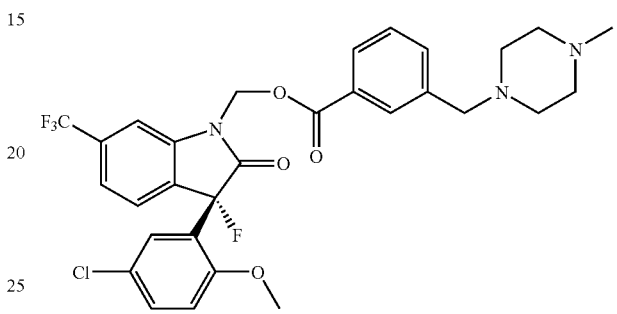

Following general procedure (E), to a suspension of (S)-XV (0.4 g, 0.74 mmol), $K_2CO_3$ (0.112 g, 0.81 mmol) and NaI (40 mg) in acetone (20 mL), 1.1 eq. of 1-methylpiperazine (0.090 mL) was added. After HCl salt formation, a light yellow precipitate was collected and purified by trituration with acetonitrile to afford the title compound as an off-white solid (0.145 g, 29% yield). mp: 190–193° C. (dec.). MS m/e: 606 (MH$^+$). Anal. Calcd. for $C_{30}H_{28}ClF_4N_3O_4$·2HCl·1.33 $H_2O$: C, 51.26; H, 4.68; N, 5.98. Found: C, 51.38; H, 4.81; N, 6.20. $^1$H NMR (DMSO-d$^6$): δ 2.78 (m, br, 3H), 3.2–3.8 (m, br, 10H), 3.38 (s, 3H), 6.17 (m, 2H), 7.04 (dd, J=7.8 Hz, 1.1 Hz, 1H), 7.51 (m, 3H), 7.61 (m, 1H), 7.72 (d, J=2.0 Hz, 1H), 7.90–7.92 (m, br, 2H), 8.00 (d, J=7.5 Hz, 1H), 8.15 (m, br, 1H). IR (KBr, cm$^{-1}$): 3432, 2956, 2441, 1764, 1728, 1632, 1490, 1458, 1319, 1269, 1193, 1129. Anal. Seq. # 98040124. Notebook# 43351-037.

EXAMPLE 27

(S)-(3-(5-chloro-2-methoxyphenyl)-3-fluoro-2-oxo-6-(trifluoromethyl)indolin-1-yl)methyl 4-((diethylamino)methyl)benzoate, trifluoroacetate (Ih$^5$)

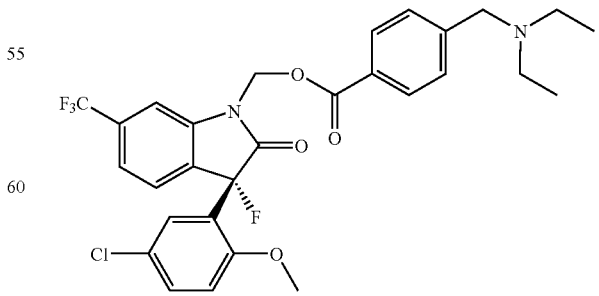

Following general procedure (E), to a suspension of (S)-XIV (0.5 g, 0.92 mmol), $K_2CO_3$ (0.14 g, 1.01 mmol) and NaI (40 mg) in acetone (20 mL), 1.1 eq. of diethylamine (0.105 mL) was added. After HCl salt formation, a light yellow solid was collected and purified by prep. HPLC to afford the title compound as a white solid as a TFA salt (0.17 g, 27% yield). mp: 75–80° C. MS m/e: 579 (MH$^+$). Anal. Calcd. for $C_{29}H_{27}ClF_4N_2O_4$.TFA.1.0 $H_2O$: C, 52.37; H, 4.25; N, 3.94. Found: C, 52.18; H, 3.90; N, 3.77. $^1$H NMR (DMSO-d$^6$): δ 1.22 (t, J=7.2 Hz, 6H), 3.09 (m, br, 4H), 3.39 (s, 3H), 4.41 (d, J=5.3 Hz, 2H), 6.16 (d, J=11.2 Hz, 1H), 6.22 (d, J=11.2 Hz, 1H), 7.07 (d, J=8.9 Hz, 1H), 7.5–7.56 (m, 3H), 7.71 (s, 1H), 7.74 (m, 2H), 7.93 (s, 1H), 8.09 (d, J=8.3 Hz, 2H), 9.48 (s, br, 1H). $^{19}$F NMR: δ −61ppm, −74 ppm, −157 ppm. IR (KBr, cm$^{-1}$): 3440, 2990, 1766, 1732, 1687, 1674, 1491, 1456, 1320, 1266, 1173, 1129.

EXAMPLE 28

(S)-(3-(5-chloro-2-methoxyphenyl)-3-fluoro-2-oxo-6-(trifluoromethyl)indolin-1-yl)methyl 3-((diethylamino)methyl)benzoate, hydrochloride (Ih$^6$)

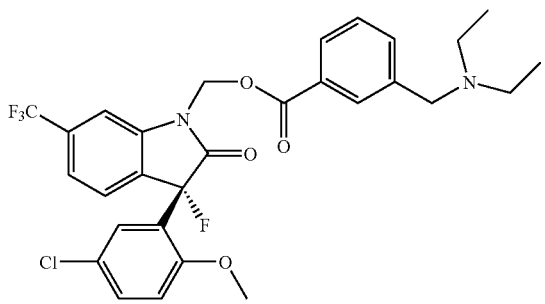

Following general procedure (E), to a suspension of (S)-XV (0.5 g, 0.92 mmol), $K_2CO_3$ (0.14 g. 1.01 mmol) and NaI (40 mg) in acetone (20 mL), 1.1 eq. of diethylamine (0.105 mL) was added. After HCl salt formation, a light yellow solid was collected and purified by recrystallization from acetonitrile/ether to afford the title compound as an off-white solid (0.188, 33% yield). mp: 195–198° C. (dec.). MS m/e: 579(MH$^+$). Anal. Calcd. for $C_{29}H_{27}ClF_4N_2O_4$.HCl: C, 56.60; H, 4.59; N, 4.55. Found: C, 56.5 1; H, 4.76; N, 4.50. $^1$H NMR (DMSO-d$^6$): δ 1.19 (t, J=7.1 Hz, 6H), 3.01 (m, 4H), 3.35 (s, 3H), 4.38 (d, J=5.5 Hz, 2H), 6.14 (d, J=11.3 Hz, 1H), 6.18 (d, J=11.3 Hz, 1H), 7.03 (dd, J=9.1 Hz, 1.4 Hz, 1H), 7.48–7.52 (m, 3H), 7.64 (t, J=7.8 Hz, 1H), 7.71 (dd, J=2.6 Hz, 0.8 Hz, 1H), 7.91 (s, 1H), 7.95 (d, J=7.8 Hz, 1H), 8.03 (d, J=7.9 Hz, 1H), 8.20 (s, 1H), 10.19 (s, br, 1H). IR (KBr, cm$^{-1}$): 3442, 2978, 2486, 1759, 1729, 1630, 1490, 1450, 1318, 1268, 1189, 1115.

EXAMPLE 29

(S)-(3-(5-chloro-2-methoxyphenyl)-3-fluoro-2-oxo-6-(trifluoromethyl)indolin-1-yl)methyl 4-(((2-(diethylamino)ethyl)(ethyl)amino)methyl)benzoate, hydrochloride (Ih$^7$)

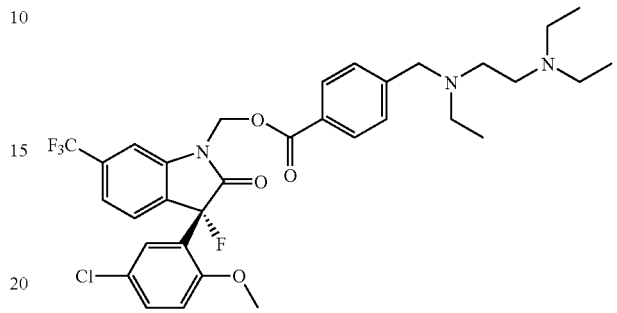

Following general procedure (E), a suspension of (S)-XIV (0.5 g, 0.92 mmol), $K_2CO_3$ (0.14 g, 1.01 mmol) and NaI (40 mg) in acetone (20 mL), 1.1 eq. of triethylethylenediamine (0.182 mL) was added. After HCl salt formation, the title compound as was collected as a light yellow solid (0.18 g, 28% yield). mp: 155–160° C. MS m/e: 650 (MH$^+$). Anal. Calcd. for $C_{33}H_{36}ClF_4N_3O_4$.2HCl.0.25 $H_2O$: C, 54.48 ; H, 5.33; N, 5.78. Found: C, 54.23; H, 5.68; N, 5.55. $^1$H NMR (DMSO-d$^6$): δ 1.19–1.24 (m, 9H), 3.14 (m, br, 8H), 3.39 (s, 3H), 3.82 (s, br, 2H), 4.45 (m, br, 1H), 4.56 (m, br, 1H), 6.14 (d, J=11.1 Hz, 1H), 6.21 (d, J=11.2 Hz, 1H), 7.04 (dd, J=9.0 Hz, 1.2 Hz, 1H), 7.5–7.55 (m, 3H), 7.72 (d, J=1.9 Hz, 1H), 7.85–7.9 (m, 3H), 8.05 (d, J=7.8 Hz, 2H), 10.9 (s, br, 1H), 11.5 (s, br, 1H). IR (KBr, cm$^{-1}$): 3432, 2979, 2620, 1763, 1729, 1632, 1490, 1456, 1319, 1265, 1171, 1131.

EXAMPLE 30

(S)-(3-(5-chloro-2-methoxyphenyl)-3-fluoro-2-oxo-6-(trifluoromethyl)indolin-1-yl)methyl 3-(((2-(diethylamino)ethyl)(ethyl)amino)methyl)benzoate, hydrochloride (Ih$^8$)

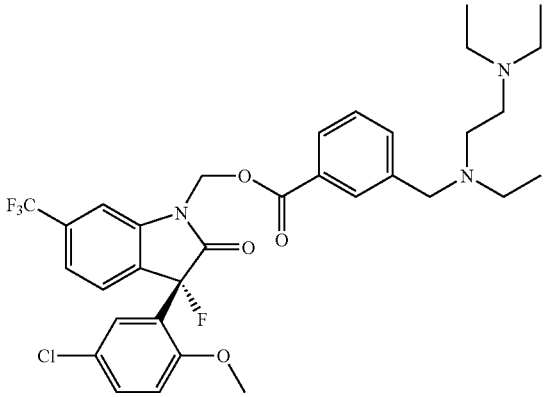

Following general procedure (E), to a suspension of (S)-XV (0.5 g, 0.92 mmol), $K_2CO_3$ (0.14 g. 1.01 mmol) and NaI (40 mg) in acetone (20 mL), 1.1 eq. of triethylethylenediamine (0.182 mL) was added. After HCl salt forma-

EXAMPLE 31

(S)-4-Piperidin-1-ylmethyl-benzoic acid 3-(5-chloro-2-methoxy-phenyl)-3-fluoro-2-oxo-6-trifluoromethyl-2,3-dihydro-indol-1-ylmethyl ester, trifluoroacetate (Ih⁹)

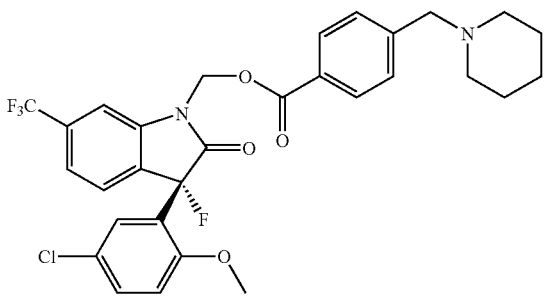

Following general procedure (E), a suspension of (S)-XIV (0.5 g, 0.92 mmol), K₂CO₃ (0.14 g, 1.01 mmol) and NaI (40 mg) in acetone (20 mL), 1.1 eq. of piperidine (0.10 mL) was added. After HCl salt formation, a light yellow solid was collected and purified by prep. HPLC to obtained a white solid as TFA salt (0.14 g, % yield). mp: 85–89° C. MS m/e: 591 (MH⁺). Anal. Calcd. for $C_{30}H_{27}ClF_4N_2O_4 \cdot TFA \cdot 1.5 H_2O$: C, 52.50; H, 4.27; N, 3.83. Found: C, 52.23; H, 3.83; N, 3.60. ¹H NMR (DMSO-d⁶): δ 1.37 (m, br, 1H), 1.5–1.7 (m. br, 3H), 1.79–1.83 (m, br, 2H), 2.87–2.91 (m, br, 2H), 3.30–3.33 (m, br, 2H), 3.40 (s, 3H), 4.38 (d, J=5.1 Hz, 2H), 6.16 (d, J=11.2 Hz, 1H), 6.22 (d, J=11.2 Hz, 1H), 7.07 (d, J=8.9 Hz, 1H), 7.50–7.56 (m, 3H), 7.69 (d, J=8.2 Hz, 2H), 7.73 (d, J=2.5 Hz, 1H), 7.9 (s, 1H), 8.09 (d, J=8.3 Hz, 2H), 9.47 (s, br, 1H). ¹⁹F NMR: δ −61 ppm, −74 ppm, −157 ppm. IR (KBr, cm⁻¹): 3450, 2564, 1766, 1732, 1673, 1457, 1320, 1266, 1173, 1131.

EXAMPLE 32

(S)-3-Piperidin-1-ylmethyl-benzoic acid 3-(5-chloro-2-methoxy-phenyl)-3-fluoro-2-oxo-6-trifluoromethyl-2,3-dihydro-indol-1-ylmethyl ester, hydrochloride (Ih¹⁰)

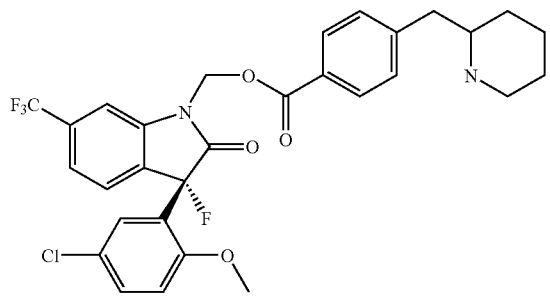

Following general procedure (E), a suspension of (S)-XV (0.44 g, 0.81 mmol), K₂CO₃ (0.123 g, 0.89 mmol) and NaI (40 mg) in acetone (20 mL), 1.1 eq. of piperidine (0.088 mL) was added. After HCl salt formation, a light yellow solid was collected and was Purified by trituration with acetonitrile/ether to afford the title compound as a white solid (0.183 g, 36% yield). mp: 222–226° C. (dec.). MS: 591(MH⁺). Anal. Calcd. for $C_{30}H_{27}ClF_4N_2O_4 \cdot HCl$: C, 57.43; H, 4.50; N, 4.46. Found: C, 57.25; H, 4.67; N, 4.42. ¹H NMR (DMSO-d⁶): δ 1.3 (m, br, 1H), 1.5–1.7 (m, br, 5H), 2.80–2.84 (m, br, 2H), 3.23 (d, br, J=11.6 Hz, 2H), 3.36 (s, 3H), 4.34 (d, J=5.2 Hz, 2H), 6.14 (d, J=11.4 Hz, 1H), 6.18 (d, J=11.3 Hz, 1H), 7.03 (dd, J=8.9 Hz, 1.2 Hz, 1H), 7.45–7.50 (m, 3H), 7.63 (t, J=7.8 Hz, 1H), 7.71 (dd, J=2.6 Hz, 0.8 Hz, 1H), 7.91–7.95 (m, 2H), 8.03 (d, J=7.9 Hz, 2H), 8.17 (s, 1H), 10.32 (s, br, 1H). IR (KBr, cm⁻¹): 3445, 2948, 2624, 2526, 1759, 1731, 1630, 1490, 1452, 1318, 1267, 1187, 1119, 1060.

EXAMPLE 33

(S)-(4-(((3-(5-chloro-2-methoxyphenyl)-3-fluoro-2-oxo-6-(trifluoromethyl)indolin-1-yl)methoxy)carbonyl)phenyl)-N,N,N-trimethylmethanaminium chloride (Ii¹)

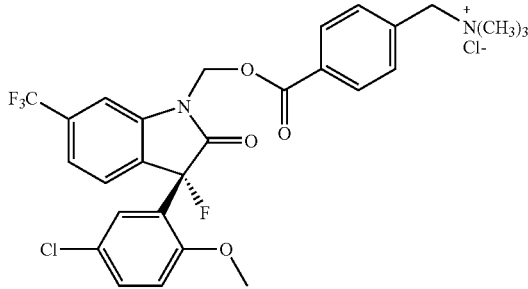

To a solution of XIV in ethyl acetate/ether mixture, anhydrous trimethylamine was bubbled into saturated the solution. The reaction mixture was stirred at rt. for 5 days. The solvents were evaporated and the residue was recrystallized from acetonitrile to afford the title compound as a white solid (0.13 g, 43% yield). mp: 204–207° C. (dec.).

MS: 565 (M+). Anal. Calcd. for $C_{28}H_{26}Cl_2F_4N_2O_4$: C, 55.92; H, 4.36; N, 4.66. Found: C, 54.86; H, 4.81; N, 5.40. $^1$H NMR (DMSO-d$^6$): δ 3.03 (s, 9H), 3.39 (s, 3H), 4.60 (m, br, 2H), 6.16 (d, J=11.2 Hz, 1H), 6.22 (d, J=11.2 Hz, 1H), 7.05 (d, J=8.9 Hz, 1H), 7.50–7.55 (m, 3H), 7.69–7.73 (m, 3 H), 7.92 (s, 1H), 8.10 (d, J=8.2 Hz, 2H). IR (KBr, cm$^{-1}$): 3409, 3011, 1762, 1751, 1709, 1633, 1490, 1461, 1317, 1256, 1135, 1073.

EXAMPLE 34

(S)-(3-(((3-(5-chloro-2-methoxyphenyl)-3-fluoro-2-oxo-6-trifluoromethyl)indolin-1-yl)methoxy)carbonyl)phenyl)-N,N,N-trimethylmethanaminium, methane sulfonate (Ii$^2$)

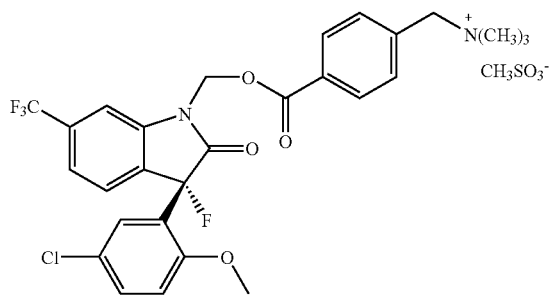

To a suspension of XV (0.5 g, 0.922 mmol), K$_2$CO$_3$ (0.14 g, 1.014 mmol) and NaI (0.05 g) in acetone (20 mL), 2.0 M solution of dimethylamine (0.5 mL, 1.01 mmol) in THF was added at rt. The reaction mixture was stirred at rt. for 2 days. TLC indicated no starting material remained. Acetone was evaporated and the residue was extracted with ether. The filtrate was then washed with sat'd NaHCO$_3$, water, brine and dried with MgSO$_4$. Evaporation of solvent gave a light yellow solid. It was then dissolved in ether and methyl methanesulfonate (0.112 mL, )was added. The reaction mixture was stirred at rt. for overnight. The precipitate was collected and purified by recrystallization in acetonitrile/ether mixture to afford the title compound (68 mg, 11% yield two steps) mp: 145–150° C. (dec.). MS: 565 (M+). Anal. Calcd. for $C_{28}H_{26}ClF_4N_2O_4\cdot CH_3SO_3\cdot 0.67H_2O$: C, 51.75; H, 4.54; N, 4.16. Found: C, 51.63; H, 4.90; N, 3.92. $^1$H NMR (DMSO-d$^6$): δ 2.29 (s, 3H), 3.02 (s, 9H), 3.38 (s, 3H), 4.62 (s, 2H), 6.19 (m, 2H), 7.05 (d, J=7.8 Hz, 1H), 7.50–7.55 (m, 3H), 7.71–7.74 (m, 2H), 7.84 (d, J=8.7 Hz, 1 H), 7.92 (s, 1H), 8.13 (d, J=7.8 Hz, 1H), 8.18 (s, 1H). IR (KBr, cm$^{-1}$): 3436, 1764, 1727, 1633, 1490, 1456, 1319, 1270, 1195, 1133.

General Procedure (F) for Preparing T-Butylester Protected Urea Derivatives of (S)-VI To a cold (0° C.) solution of (S)-IV (0.5 g, 1.39 mmol) and triethylamine (0.232 mL, 1.67 mmol) in methylene chloride (15 mL), p-nitrophenyl chloroformate (0.31 g, 1.53 mmol) in methylene chloride (10 mL) solution was added dropwise. The reaction mixture turned slightly yellow and was allowed to warm to rt. for 2 hr. TLC showed that no (S)-IV remained. The amino acid t-butylester and triethylamine were added and the yellow solution was stirred at rt. for overnight. The reaction mixture was washed with 1N HCl, sat'd NaHCO$_3$, water, brine and dried with MgSO$_4$. The solvent was evaporated and the residue was purified by flash column chromatography (silica gel, 3:1 hexanes:ethyl acetate) to give a white foamy solid.

General Procedure (G) for Hydrolysis of t-Butyl Esters

To a solution of t-butyl ester in methylene chloride, trifluoroacetic acid (TFA) was added. The reaction mixture was stirred at rt. for overnight. The solvent and TFA were evaporated and the crude product was purified by prep. HPLC or recrystallization.

EXAMPLE 35

(S)-2-((S)-3-(5-chloro-2-methoxyphenyl)-3-fluoro-2-oxo-6-(trifluoromethyl)-indoline-1-carboxamido) propanoic acid (Ij$^1$)

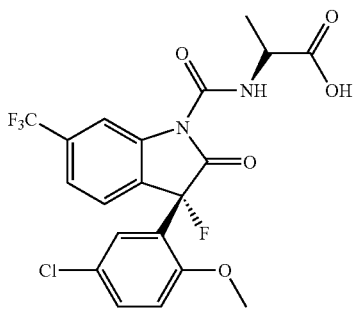

Step A. (S)-tert-butyl 2-((S)-3-(5-chloro-2-methoxyphenyl)-3-fluoro-2-oxo-6-(trifluoromethyl)indoline-1-carboxamido)propanoate (XVIII$^1$): Following general procedure (F), after forming the intermediate, (L)-Alanine-t-butyl ester hydrochloride (0.252 g, 1.39 mmol) and triethylamine (0.39 mL, 2.78 mmol) were added. After work-up and purification, 0.38 g of the title compound was obtained as a white foam solid (52% yield). mp: 62–64° C. MS: 531 (MH+). Anal. Calcd. for $C_{24}H_{23}ClF_4N_2O_5$: C, 54.30; H, 4.37; N, 5.28. Found: C, 54.37; H, 4.38; N, 5.16. $^1$H NMR (CDCl$_3$): δ 1.51 (s, 9H), 1.56 (d, J=6.9 Hz, 3H), 3.54 (s, 3H), 4.52 (m, 1H), 6.77 (dd, J=8.8 Hz, 1.4 Hz, 1H), 7.25 (m, 1H), 7.36 (dd, J=8.7 Hz, 2.6 Hz, 1H), 7.43 (d, J=7.9 Hz, 1H), 7.80 (dd, J=2.5 Hz, 0.9 Hz, 1H), 8.6 (m, 1H), 8.76 (d, J=6.8 Hz, 1H). IR (KBr, cm$^{-1}$): 3338, 2983, 1765, 1737, 1716, 1520, 1490, 1439, 1319, 1262, 1172, 1130.

Step B. (S)-2-((S)-3-(5-chloro-2-methoxyphenyl)-3-fluoro-2-oxo-6-(trifluoromethyl)indoline-1-carboxamido) propanoic acid (Ij$^1$): Following general procedure (G), to a solution of XVIII$^1$ (0.3 g, 0.565 mmol) in methylene chloride (5 mL), TFA (0.44 mL, 5.65 mmol) was added. After purification by prep. HPLC, the title compound as was obtained as a white foam solid (180 mg, 67% yield). mp: 103–107° C. MS: 475 (MH+). Anal. Calcd. for $C_{20}H_{15}ClF_4N_2O_5$: C, 50.59; H, 3.18; N, 5.90. Found: C, 50.24; H, 3.27; N, 5.77. $^1$H NMR (CDCl$_3$): δ 1.63 (d, J=7.2 Hz, 3H), 3.54 (s, 3H), 4.67 (m, 1H), 6.78 (dd, J=8.7 Hz, 1.1 Hz, 1H), 7.28 (m, 1H), 7.37 (dd, J=8.8 Hz, 2.6 Hz, 1H), 7.44 (d, J=7.9 Hz, 1H), 7.80 (dd, J=2.5 Hz, 0.8 Hz, 1H), 8.60 (s, 1H), 8.72 (d, J=6.7 Hz, 1H). IR (KBr, cm$^{-1}$): 3338, 1764, 1716, 1531, 1490, 1439, 1367, 1319, 1265, 1175, 1131, 1061.

EXAMPLE 36

(S)-2-(3-((S)-3-(5-chloro-2-methoxyphenyl)-3-fluoro-2-oxo-6-(trifluoromethyl)indolin-1-yl)ureido)succinic acid (Ij²)

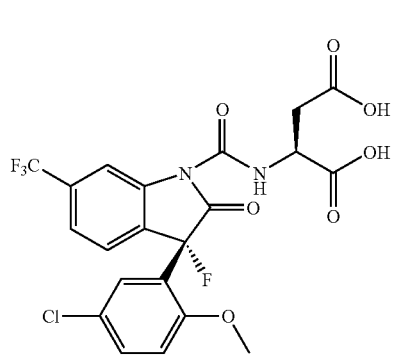

Step A. (S)-di-tert-butyl 2-((S)-3-(5-chloro-2-methoxyphenyl)-3-fluoro-2-oxo-6-(trifluoromethyl)indoline-1-carboxamido)succinate (XVIII²): Following general procedure (F), after forming the intermediate, (L)-Aspartic acid di-t-butyl ester hydrochloride (0.391 g, 1.39 mmol) and triethylamine (0.39 mL, 2.78 mmol) were added. After work-up and purification, 0.44 g of the title compound as white foam solid was obtained (50% yield). mp: 63–66° C. MS: 631 (MH⁺). Anal. Calcd. for $C_{29}H_{31}ClF_4N_2O_7$: C, 55.20; H, 4.95; N, 4.44. Found: C, 55.07; H, 4.63; N, 4.27. ¹H NMR (CDCl₃): δ 1.44 (s, 9H), 1.51 (s, 9H), 2.87 (dd, J=16.8 Hz, 4.8 Hz, 1H), 3.01 (dd, J=16.8 Hz, 4.8 Hz, 1H), 3.52 (s, 3H), 4.78 (dt, J=7.8 Hz, 4.7 Hz, 1H), 6.75 (dd, J=8.8 Hz, 1.2 Hz, 1H), 7.25 (m, 1H), 7.35 (dd, J=8.7 Hz, 2.6 Hz, 1H), 7.42 (d, J=7.9 Hz, 1H), 7.80 (dd, J=2.6 Hz, 0.9 Hz, 1H), 8.6 (s, 1H), 9.02 (d, J=7.7 Hz, 1H). IR (KBr, cm⁻¹): 3338, 2982, 2942, 1766, 1733, 1520, 1491, 1440, 1319, 1262, 1170, 1132.

Step B. (S)-2-(3-((S)-3-(5-chloro-2-methoxyphenyl)-3-fluoro-2-oxo-6-(trifluoromethyl)indolin-1-yl)ureido)succinic acid (Ij²): Following general procedure (G), to a solution of XVIII² (0.377 g, 0.597 mmol) in methylene chloride (5 mL), TFA (0.92 mL, 11.94 mmol) was added. After purification by recrystallization from ether/hexanes, the title compound was obtained as a white solid (178 mg, 57% yield). mp: 199–202° C. MS: 519 (MH⁺). Anal. Calcd. for $C_{21}H_{15}ClF_4N_2O_7$: C, 48.62; H, 2.91; N, 5.40. Found: C, 48.51; H, 2.99; N, 5.24. ¹H NMR (DMSO-d⁶): δ 2.93 (m, J=5.1 Hz, 2H), 3.52 (s, 3H), 4.76 (m, 1H), 7.12 (dd, J=9.5 Hz, 1.2 Hz, 1H), 7.55 (dd, J=8.8 Hz, 2.6 Hz, 1H), 7.62 (m, 2H), 7.79 (d, J=1.7 Hz, 1H), 8.43 (s, 1H), 8.92 (d, J=7.8 Hz, 1H). IR (KBr, cm⁻¹): 3370, 2945, 1767, 1711, 1518, 1490, 1440, 1321, 1266, 1178, 1128.

EXAMPLE 37

(S)-2-((S)-3-(5-chloro-2-methoxyphenyl)-3-fluoro-2-oxo-6-(trifluoromethyl)-indoline-1-carboxamido)pentanedioic acid (Ij³)

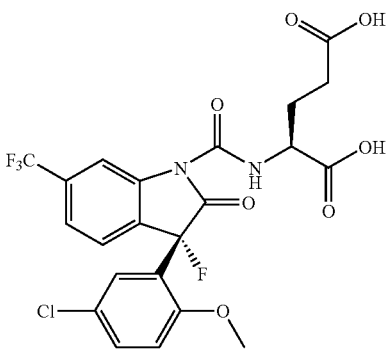

Step A. (S)-di-tert-butyl 2-((S)-3-(5-chloro-2-methoxyphenyl)-3-fluoro-2-oxo-6-(trifluoromethyl)indoline-1-carboxamido)pentanedioate (XVIII³)

Following general procedure (F), after forming the intermediate, (L)-Glutamic acid di-t-butyl ester hydrochloride (0.411 g, 1.39 mmol) and triethylamine (0.39 mL, 2.78 mmol) were added. After work-up and purification, 0.30 g of the title compound as a white foam solid was obtained (33% yield). mp: 54–57° C. MS: 645 (MH⁺). Anal. Calcd. for $C_{30}H_{33}ClF_4N_2O_7$: C, 55.86; H, 5.16; N, 4.34. Found: C, 55.89; H, 5.20; N, 4.30. ¹H NMR (CDCl₃): δ 1.44 (s, 9H), 1.52 (s, 9H), 2.0–2.1 (m, 1H), 2.2–2.4 (m, 3H), 3.56 (s, 3H), 4.60 (dt, J=7.7 Hz, 5.2 Hz, 1H), 6.78 (dd, J=8.8 Hz, 1.3 Hz, 1H), 7.26 (m, 1H), 7.37 (dd, J=8.7 Hz, 2.6 Hz, 1H), 7.43 (d, J=7.9 Hz, 1H), 7.80 (dd, J=2.6 Hz, 0.8 Hz, 1H), 8.59 (s, 1H), 8.72 (d, J=7.5 Hz, 1H). IR (KBr, cm⁻¹): 3337, 2981, 2943, 1764, 1733, 1718, 1522, 1491, 1440, 1319, 1261, 1156.

Step B. (S)-2-((S)-3-(5-chloro-2-methoxyphenyl)-3-fluoro-2-oxo-6-(trifluoromethyl)-indoline-1-carboxamido)pentanedioic acid (Ij³): Following general procedure (G), to a solution of XVIII³ (0.17 g, 0.419 mmol) in methylene chloride (5 mL), TFA (0.64 mL, 8.37 mmol) was added. After evaporation of solvent, the title compound was obtained as a white foam solid (118 mg, 53% yield). mp: 90–94° C. MS: 531 (M–H⁻). Anal. Calcd. for $C_{22}H_{17}ClF_4N_2O_7$: C, 49.59; H, 3.22; N, 5.26. Found: C, 49.56; H, 3.22; N, 4.63. ¹H NMR (CDCl₃): δ 2.3–2.6 (m, 4H), 3.55 (s, 3H), 4.70 (m, 1H), 6.79 (dd, J=8.9 Hz, 1.3 Hz, 1H), 7.29 (m, 1H), 7.38 (dd, J=8.8 Hz, 2.6 Hz, 1H), 7.45 (d, J=7.8 Hz, 1H), 7.81 (dd, J=2.4 Hz, 0.8 Hz, 1H), 8.57 (s, 1H), 8.89 (d, J=6.5 Hz, 1H). IR (KBr, cm⁻¹): 3326, 1762, 1713, 1530, 1490, 1440, 1319, 1265, 1172, 1129, 1061.

EXAMPLE 38

(S)-2-(3-(5-chloro-2-methoxyphenyl)-3-fluoro-2-oxo-6-(trifluoromethyl)-indoline-1-carboxamido)-2-methylpropanoic acid (Ij[4])

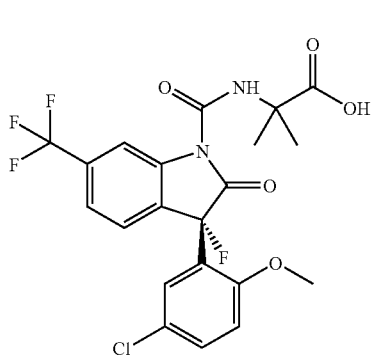

Step A. (S)-tert-butyl 2-(3-(5-chloro-2-methoxyphenyl)-3-fluoro-2-oxo-6-(trifluoromethyl)indoline-1-carboxamido)-2-methylpropanoate (XVIII[4]): Following general procedure (F), after forming the intermediate, H-α-Me-Ala-To-Bu (0.221 g, 1.39 mmol) and triethylamine (0.213 mL, 1.53 mmol) were added. After work-up and purification, 0.28 g of the title compound as a white foam solid was obtained (37% yield). mp: 57–60° C. MS: 489 (no molecular ion). Anal. Calcd. for $C_{25}H_{25}ClF_4N_2O_5$: C, 55.10; H, 4.62; N, 5.14. Found: C, 55.37; H, 4.82; N, 5.01. $^1$H NMR (CDCl$_3$): δ 1.50 (s, 9H), 1.65 (s, 3H), 1.67 (s, 3H), 3.56 (s, 3H), 6.77 (dd, J=8.8 Hz, 1.3 Hz, 1H), 7.25 (m, 1H), 7.36 (dd, J=8.7 Hz, 2.6 Hz, 1H), 7.42 (d, J=7.8 Hz, 1H), 7.80 (dd, J=2.6 Hz, 1.0 Hz, 1H), 8.6 (s, 1H), 8.87 (s, 1H). IR (KBr, cm$^{-1}$): 3338, 2984, 1762, 1735, 1716, 1531, 1491, 1439, 1319, 1264, 1173, 1132, 1061.

Step B. (S)-tert-butyl 2-(3-(5-chloro-2-methoxyphenyl)-3-fluoro-2-oxo-6-(trifluoromethyl)indoline-1-carboxamido)-2-methylpropanoate (Ij[4]): Following general procedure (G), to a solution of XVIII[4] (0.24 g, 0.44 mmol) in methylene chloride (5 mL), TFA (0.34 mL, 4.4 mmol) was added. After purification by Prep. HPLC, the title compound was obtained as a white foam solid (140 mg, 65% yield). mp: 107–110° C. MS: 487 (M–H$^-$) (very weak). Anal. Calcd. for $C_{21}H_{17}ClF_4N_2O_5$: C, 51.60; H, 3.51; N, 5.73. Found: C, 51.29; H, 3.68; N, 5.49. $^1$H NMR (CDCl$_3$): δ 1.70 (s, 3H), 1.74 (s, 3H), 3.56 (s, 3H), 6.76 (dd, J=8.8 Hz, 1.3 Hz, 1H), 7.27 (m, 1H), 7.36 (dd, J=8.7 Hz, 2.6 Hz, 1H), 7.44 (d, J=7.9 Hz, 1H), 7.79 (dd, J=2.5 Hz, 0.9 Hz, 1H), 8.59 (s, 1H), 8.78 (s, 1H). IR (KBr, cm$^{-1}$): 3500, 3337, 1762, 1717, 1532, 1491, 1439, 1320, 1265, 1173, 1132, 1062.

EXAMPLE 39

(S)-2-((S)-3-(5-chloro-2-methoxyphenyl)-3-fluoro-2-oxo-6-(trifluoromethyl)-indoline-1-carboxamido)-3-methylbutanoic acid (Ij[5])

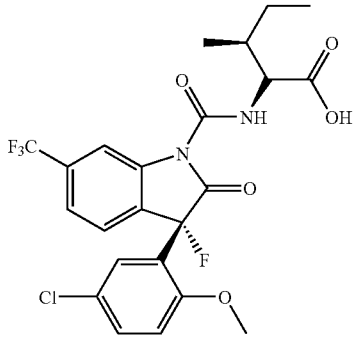

Step A. (S)-tert-butyl 2-((S)-3-(5-chloro-2-methoxyphenyl)-3-fluoro-2-oxo-6-(trifluoromethyl)indoline-1-carboxamido)-3-methylbutanoate (XVIII[5]): Following general procedure (F), after forming the intermediate, L-valine t-butyl ester hydrochloride (0.321 g, 1.53 mmol) and triethylamine (0.41 mL, 2.92 mmol) were added. After work-up and purification, 0.40 g of the title compound as a white foam solid was obtained (52% yield). mp: 56–60° C. MS: 489 (no mother ion). Anal. Calcd. for $C_{26}H_{27}ClF_4N_2O_5$: C, 55.87; H, 4.87; N, 5.01. Found: C, 55.95; H, 4.89; N, 4.89. $^1$H NMR (CDCl$_3$): δ 0.99 (d, J=6.9 Hz, 3H), 1.04 (d, J=6.8 Hz, 3H), 1.51 (s, 9H), 2.33 (m, 1H), 3.55 (s, 3H), 4.50 (dd, J=8.5 Hz, 4.5 Hz, 1H), 6.78 (dd, J=8.8 Hz, 1.2 Hz, 1H), 7.27 (m, 1H), 7.37 (dd, J=8.7 Hz, 2.6 Hz, 1H), 7.43 (d, J=7.9 Hz, 1H), 7.81 (dd, J=2.6 Hz, 0.9 Hz, 1H), 8.6 (s, 1H), 8.70 (d, J=8.4 Hz, 1H). IR (KBr, cm$^{-1}$): 3338, 2972, 1761, 1735, 1717, 1531, 1491, 1439, 1319, 1261, 1173, 1132, 1061.

Step B. (S)-2-((S)-3-(5-chloro-2-methoxyphenyl)-3-fluoro-2-oxo-6-(trifluoromethyl)-indoline-1-carboxamido)-3-methylbutanoic acid (Ij[5]): Following general procedure (G), to a solution of XVIII[5] (0.36 g, 0.644 mmol) in methylene chloride (5 mL), TFA (0.5 mL, 6.44 mmol) was added. After purification by Prep. HPLC, the title compound was obtained as a white foam solid (195 mg, 60% yield). mp: 100–104° C. MS: 501 (M–H$^-$). Anal. Calcd. for $C_{22}H_{19}ClF_4N_2O_5 \cdot 0.25\ H_2O$: C, 52.08; H, 3.87; N, 5.52. Found: C, 51.94; H, 3.90; N, 5.45. $^1$H NMR (CDCl$_3$): δ 1.05 (d, J=6.9 Hz, 3H), 1.09 (d, J=6.8 Hz, 3H), 2.44 (m, 1H), 3.55 (s, 3H), 4.63 (dd, J=8.1 Hz, 4.6 Hz, 1H), 6.78 (dd, J=8.8 Hz, 1.1 Hz, 1H), 7.27 (m, 1H), 7.38 (dd, J=8.7 Hz, 2.6 Hz, 1H), 7.44 (d, J=7.9 Hz, 1H), 7.81 (dd, J=2.5 Hz, 0.9 Hz, 1H), 8.60 (s, 1H), 8.73 (d, J=8.1 Hz, 1H). IR (KBr, cm$^{-1}$): 3335, 2970, 1761, 1717, 1539, 1490, 1439, 1319, 1264, 1174, 1132.

EXAMPLE 40

(2S,3S)-2-((S)-3-(5-chloro-2-methoxyphenyl)-3-fluoro-2-oxo-6-(trifluoromethyl)indoline-1-carboxamido)-3-methylpentanoic acid (Ij⁶)

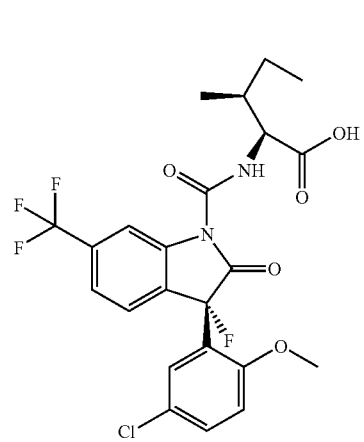

Step A. (2S,3S)-tert-butyl 2-((S)-3-(5-chloro-2-methoxyphenyl)-3-fluoro-2-oxo-6-(trifluoromethyl)indoline-1-carboxamido)-3-methylpentanoate (XVIII⁶): Following general procedure (F), after forming the intermediate, L-isoleucine t-butyl ester hydrochloride (0.342 g, 1.53 mmol) and triethylamine (0.41 mL, 2.92 mmol) were added. After work-up and purification, 0.362 g of the title compound as a white foam solid was obtained (45% yield). mp: 56–60° C. MS: 573 (MH⁺). Anal. Calcd. for $C_{27}H_{29}ClF_4N_2O_5$: C, 56.60; H, 5.10; N, 4.89. Found: C, 56.53; H, 5.02; N, 4.80. $^1$H NMR (CDCl₃): δ 0.95–1.02 (m, 6H), 1.26 (m, 1H), 1.51 (s, 9H), 1.55 (m, 1H), 2.05 (m, 1H), 3.55 (s, 3H), 4.54 (dd, J=8.3 Hz, 4.5 Hz, 1H), 6.78 (dd, J=8.8 Hz, 1.3 Hz, 1H), 7.25 (m, 1H), 7.37 (dd, J=8.7 Hz, 2.6 Hz, 1H), 7.43 (d, J=7.8 Hz, 1H), 7.81 (dd, J=2.6 Hz, 1.0 Hz, 1H), 8.60 (s, 1H), 8.73 (d, J=8.1 Hz, 1H). IR (KBr, cm⁻¹): 3338, 2973, 1761, 1736, 1716, 1530, 1491, 1439, 1319, 1261, 1176, 1132, 1061.

Step B. (2S,3S)-2-((S)-3-(5-chloro-2-methoxyphenyl)-3-fluoro-2-oxo-6-(trifluoromethyl)indoline-1-carboxamido)-3-methylpentanoic acid (Ij⁶): Following general procedure (G), to a solution of XVIII⁶ (0.335 g, 0.585 mmol) in methylene chloride (10 mL), TFA (0.45 mL, 5.85 mmol) was added. After purification by Prep. HPLC, the title compound was obtained as a white foam solid (118 mg, 39% yield). mp: 88–92° C. MS: 517 (MH⁺). Anal. Calcd. for $C_{23}H_{21}ClF_4N_2O_5 \cdot 0.5 H_2O$: C, 52.53; H, 4.22; N, 5.33. Found: C, 52.28; H, 4.14; N, 5.19. $^1$H NMR (CDCl₃): δ 0.99 (t, J=7.3 Hz, 3H), 1.06 (d, J=6.9 Hz, 3H), 1.32 (m, 1H), 1.57 (m, 1H), 2.16 (m, 1H), 3.55 (s, 3H), 4.67 (dd, J=8.0 Hz, 4.6 Hz, 1H), 6.78 (dd, J=8.9 Hz, 1.2 Hz, 1H), 7.28 (m, 1H), 7.38 (dd, J=8.8 Hz, 2.5 Hz, 1H), 7.44 (d, J=7.9 Hz, 1H), 7.80 (m, 1H), 8.60 (s, 1H), 8.74 (d, J=8.0 Hz, 1H). IR (KBr, cm⁻¹): 3333, 2970, 1761, 1717, 1537, 1491, 1440, 1319, 1264, 1175, 1132, 1062.

EXAMPLE 41

(S)-2-((S)-3-(5-chloro-2-methoxyphenyl)-3-fluoro-2-oxo-6-(trifluoromethyl)-indoline-1-carboxamido)-3-phenylpropanoic acid (Ij⁷)

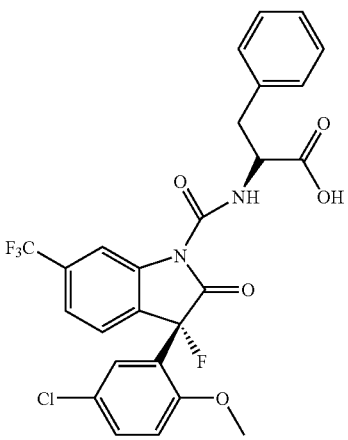

Step A. (S)-tert-butyl 2-((S)-3-(5-chloro-2-methoxyphenyl)-3-fluoro-2-oxo-6-(trifluoromethyl)indoline-1-carboxamido)-3-phenylpropanoate (XVIII⁷): Following general procedure (F), after forming the intermediate, L-phenylalanine t-butyl ester hydrochloride (0.394 g, 1.53 mmol) and triethylamine (0.41 mL, 2.92 mmol) were added. After work-up and purification, 0.343 g of the title compound as a white foam solid was obtained (42% yield). mp: 62–66° C. MS: 607 (MH⁺). Anal. Calcd. for $C_{29}H_{25}ClF_4N_2O_5 \cdot 0.5H_2O$: C, 58.49; H, 4.58; N, 4.55. Found: C, 58.47; H, 4.57; N, 4.28. $^1$H NMR (CDCl₃): δ 1.46 (s, 9H), 3.13 (dd, J=14.0 Hz, 7.6 Hz, 1H), 3.30 (dd, J=14.0 Hz, 5.6 Hz, 1H), 3.34 (s, 3H), 4.80 (m, 1H), 6.74 (dd, J=8.8 Hz, 1.3 Hz, 1H), 7.20–7.27 (m, 6H), 7.36 (dd, J=8.7 Hz, 2.6 Hz, 1H), 7.41 (d, J=7.9 Hz, 1H), 7.78 (dd, J=2.5 Hz, 0.8 Hz, 1H), 8.57 (s, 1H), 8.68 (d, J=7.4 Hz, 1H). IR (KBr, cm⁻¹): 3332, 2980, 1763, 1737, 1716, 1521, 1491, 1439, 1367, 1319, 1262, 1171, 1131, 1061.

Step B. (S)-2-((S)-3-(5-chloro-2-methoxyphenyl)-3-fluoro-2-oxo-6-(trifluoromethyl)indoline-1-carboxamido)-3-phenylpropanoic acid (Ij⁷): Following general procedure (G), to a solution of XVIII⁷ (0.275 g, 0.453 mmol) in methylene chloride (5 mL), TFA (0.36 mL, 4.64 mmol) was added. After purification by Prep. HPLC, the title compound was obtained as a white foam solid (142 mg, 57% yield) mp: 98–102° C. MS: 549 (M−H). Anal. Calcd. for $C_{26}H_{19}ClF_4N_2O_5$: C, 56.69; H, 3.48; N, 5.09. Found: C, 56.39; H, 3.46; N, 4.99. $^1$H NMR (CDCl₃): δ 3.16 (dd, J=14.2 Hz, 8.7 Hz, 1H), 3.29 (s, 3H), 3.43 (dd, J=14.3 Hz, 4.9 Hz, 1H), 4.92 (m, 1H), 6.74 (d, J=8.9 Hz, 1H), 7.23–7.29 (m, 6H), 7.36 (dd, J=8.7 Hz, 2.6 Hz, 1H), 7.42 (d, J=7.9 Hz, 1H), 7.77 (d, J=1.7 Hz, 1H), 8.56 (s, 1H), 8.66 (d, J=6.9 Hz, 1H). IR (KBr, cm⁻¹): 3435, 3326, 1762, 1716, 1531, 1490, 1439, 1319, 1264, 1173, 1130.

EXAMPLE 42

(S)-3-(3-(5-chloro-2-methoxyphenyl)-3-fluoro-2-oxo-6-(trifluoromethyl)-indoline-1-carboxamido) propanoic acid (Ij$^8$)

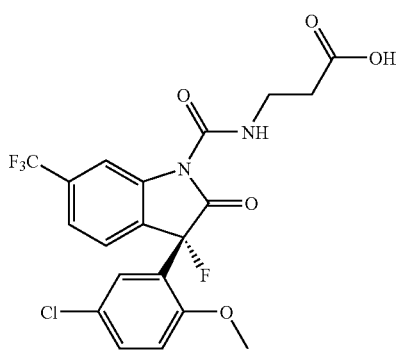

Step A. (S)-tert-butyl 3-(3-(5-chloro-2-methoxyphenyl)-3-fluoro-2-oxo-6-(trifluoromethyl)indoline-1-carboxamido) propanoate (XVIII$^8$): Following general procedure (F), after forming the intermediate, β-alanine t-butyl ester hydrochloride (0.278 g, 1.53 mmol) and triethylamine (0.41 mL, 2.92 mmol) were added. After work-up and purification, 0.48 g of the title compound as a white foam solid was obtained (65% yield). mp: 50–53° C. MS: 531 (MH$^+$). Anal. Calcd. for $C_{24}H_{23}ClF_4N_2O_5$: C, 54.30; H, 4.37; N, 5.28. Found: C, 54.21; H, 4.44; N, 5.25. $^1$H NMR (CDCl$_3$): δ 1.46 (s, 9H), 2.60 (t, J=6.2, 2H), 3.53 (s, 3H), 3.70 (m, 2H), 6.77 (d, J=8.7 Hz, 1H), 7.25 (m, 1H), 7.36 (dd, J=8.8 Hz, 2.6 Hz, 1H), 7.42 (d, J=7.8 Hz, 1H), 7.79 (d, J=2.2 Hz, 1H), 8.56 (t, J=5.6 Hz, 1H), 8.63 (s, 1H). IR (KBr, cm$^{-1}$): 3351, 2981, 1762, 1721, 1531, 1491, 1439, 1319, 1261, 1171, 1130, 1060.

Step B. (S)-3-(3-(5-chloro-2-methoxyphenyl)-3-fluoro-2-oxo-6-(trifluoromethyl)-indoline-1-carboxamido)propanoic acid (Ij8): Following general procedure (G), to a solution of XVIII$^8$ (0.415 g, 0.782 mmol) in methylene chloride (10 mL), TFA (0.60 mL, 7.82 mmol) was added. After purification by Prep. HPLC, the title compound was obtained as a white foam solid (225 mg, 61% yield). mp: 72–76° C. MS: 475 (MH$^+$). Anal. Calcd. for $C_{20}H_{15}ClF_4N_2O_5$: C, 50.59; H, 3.18; N, 5.90. Found: C, 50.36; H, 3.29; N, 5.68. $^1$H NMR (CDCl$_3$): δ 2.75 (t, J=6.2 Hz, 2H), 3.52 (s, 3H), 3.67–3.80 (m, 2H), 6.77 (dd, J=8.7 Hz, 1.1 Hz, 1H), 7.25 (m, 1H), 7.35 (dd, J=8.7 Hz, 2.6 Hz, 1H), 7.43 (d, J=7.8 Hz, 1H), 7.78 (d, J=1.8 Hz, 1H), 8.57–8.61 (m, 2H). IR (KBr, cm$^{-1}$): 3347, 2948, 1761, 1716, 1535, 1491, 1440, 1319, 1264, 1175, 1130, 1061.

What is claimed is:

1. A compound having the general Formula I

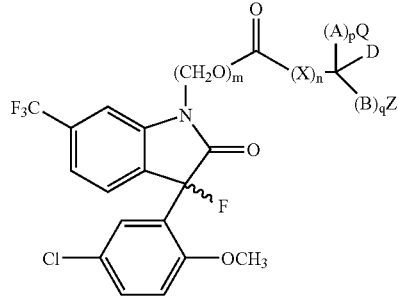

wherein the wavy bond (⁓⁓⁓)

represents the racemate, the (R)-enantiomer or the (S)-enantiomer;

A and B are independently $C_{1-4}$ alkyl or a direct bond;
D is H or CH$_3$;
X is O, CH$_2$, phenyl or (NR$_1$)$_r$;
Q and Z are each independently H, SO$_3$H, NR$_1$R$_2$, NR$_1$—CH$_2$CH$_2$—NR$_1$R$_2$, $\overset{\oplus}{NR_1R_2R_3}$, —C(O)OH, OH, OCH$_2$C(O)OH, C(O)OCH$_2$CO(O)H, C(O)NR$_1$CH$_2$CH$_2$SO$_3$H, phenyl, piperdinyl, piperizinyl, methylpiperizinyl, morpholinyl, or tetrazol-5-yl;
m, n, p, q, r are each independently an integer of 0 or 1; and
R$_1$, R$_2$, and R$_3$ are each independently H or C$_{1-4}$ alkyl;

or a nontoxic pharmaceutically acceptable salt or solvate thereof.

2. The compound of claim 1 having the general Formula I'

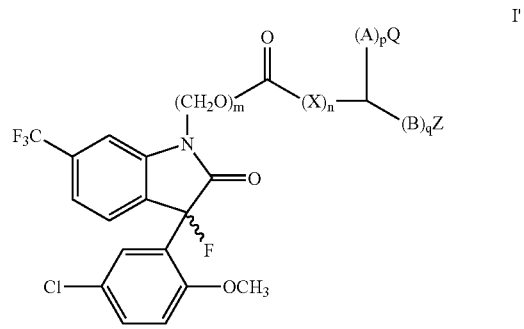

wherein the wavy bond (⁓⁓⁓) represents the racemate, the (R)-enantiomer or the (S)-enantiomer;
A and B are independently $C_{1-4}$ alkyl or a direct bond;
X is O, CH$_2$, phenyl or (NR$_1$)$_r$;

Q and Z are each independently H, NR$_1$R$_2$, NR$_1$—CH$_2$CH$_2$—NR$_1$R$_2$, $\overset{\oplus}{N}R_1R_2R_3$, —C(O)OH, OH, OCH$_2$C(O)OH, C(O)OCH$_2$CO(O)H, phenyl,
piperdinyl, piperizinyl, methylpiperizinyl, morpholinyl or tetrazol-5-yl;
m, n, p, q, r are each independently an integer of 0 or 1; and
R$_1$, R$_2$, and R$_3$ are each independently H or C$_{1-4}$ alkyl;
or a nontoxic pharmaceutically acceptable salt or solvate thereof.

3. The compound of claim 2 wherein the wavy bond (∿∿∿)

represents the racemate, the (R)-enantiomer or the (S)-enantiomer;
A and B are independently C$_{1-4}$ alkyl or a direct bond;
X is O, CH$_2$ or (NR$_1$)$_r$;
Q and Z are each independently H, NR$_1$R$_2$, NR$_1$—CH$_2$CH$_2$—NR$_1$R$_2$, $\overset{\oplus}{N}R_1R_2R_3$, —C(O)OH, OH, OCH$_2$C(O)OH, C(O)OCH$_2$CO(O)H or phenyl;
m, n, p, q, r are each independently an integer of 0 or 1; and
R$_1$, R$_2$, and R$_3$ are each independently H or C$_{1-4}$ alkyl;
or a nontoxic pharmaceutically acceptable salt or solvate thereof.

4. The compound of claim 2 wherein the wavy bond (∿∿∿)

represents the (S)-enantiomer.

5. The compound of claim 4 which is
(S)-4-(((S)-3-(5-chloro-2-methoxyphenyl)-3-fluoro-2-oxo-6-(trifluoromethyl)indolin-1-yl)methoxy)-2-hydroxy-4-oxobutanoic acid; or
(S)-4-((3-(5-chloro-2-methoxyphenyl)-3-fluoro-2-oxo-6-(trifluoromethyl)indoline-1-carbonyloxy)methoxy)-4-oxobutanoic acid;
or a nontoxic pharmaceutically acceptable salt or solvate thereof.

6. A pharmaceutical composition comprising a therapeutically effective amount of a compound as defined in claim 1 in association with a pharmaceutically acceptable carrier or diluent.

7. A method for the treatment of disorders responsive to opening of the large conductance calcium-activated potassium channels in a mammal in need thereof, wherein the disorder is ischemia, stroke, convulsions, epilepsy, asthma, irritable bowel syndrome, migraine, traumatic brain injury, elevated intracranial pressure, spinal cord injury, carbon monoxide poisoning, sexual dysfunction and urinary incontinence, which comprises administering to said mammal a therapeutically effective amount of a compound as defined in claim 1.

8. The method of claim 7 wherein the disorder is stroke.

9. The method of claim 7 wherein the disorder is traumatic brain injury.

10. The method of claim 7 wherein the disorder is elevated intracranial pressure.

\* \* \* \* \*